(12) United States Patent
Jacobson et al.

(10) Patent No.: US 6,790,845 B2
(45) Date of Patent: Sep. 14, 2004

(54) FUSED HETEROCYCLIC INHIBITORS OF FACTOR XA

(75) Inventors: Irina C. Jacobson, Sammamish, VA (US); Mimi L. Quan, Newark, DE (US); Ruth R. Wexler, Chadds Ford, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 87 days.

(21) Appl. No.: 10/118,102

(22) Filed: Apr. 8, 2002

(65) Prior Publication Data

US 2003/0087909 A1 May 8, 2003

Related U.S. Application Data

(60) Provisional application No. 60/282,438, filed on Apr. 9, 2001.

(51) Int. Cl.$^7$ ................ A61K 31/33; A61K 31/435; C07D 211/56; C07D 211/36; C07D 211/94
(52) U.S. Cl. .............. 514/183; 514/277; 514/345; 546/216; 546/223; 546/242; 546/244
(58) Field of Search ................ 514/183, 277, 514/345; 546/216, 223, 242, 244

(56) References Cited

FOREIGN PATENT DOCUMENTS

| CH | CH583226 | | 12/1976 |
|----|----------|---|---------|
| WO | 9824766 | * | 6/1998 |
| WO | WO 9950257 A | | 10/1999 |
| WO | WO 9962904 A | | 12/1999 |
| WO | 9962904 | * | 12/1999 |
| WO | WO 00/47563 A | | 8/2000 |

OTHER PUBLICATIONS

PubMed Abstract 11060682, also cited as Expert Opin Investing Drugs, 9/2,355–69(2000).*
PubMed ASbstract 8578525, also cited as Thromb Haemost. 74/1,565–71(1995).*
CAPLUS DN 129:67702, also cited as WO9824766.*

* cited by examiner

Primary Examiner—Richard L. Raymond
Assistant Examiner—Sudhaker B. Patel
(74) Attorney, Agent, or Firm—Jing S. Belfield; David H. Vance

(57) ABSTRACT

This invention relates generally to a novel class of fused heterocyclic compounds of the Formula (I) or Formula (II):

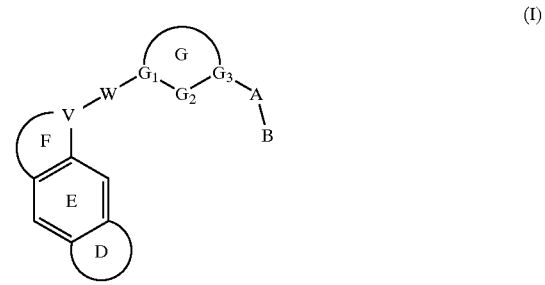

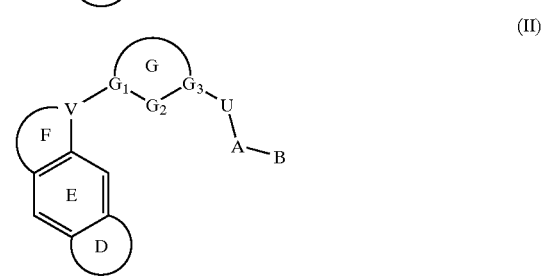

or pharmaceutically acceptable salt forms thereof, which are inhibitors of trypsin-like serine protease enzymes, especially factor Xa, pharmaceutical compositions containing the same, and methods of using the same as anticoagulant agents for treatment and prevention of thromboembolic disorders.

37 Claims, No Drawings

US 6,790,845 B2

FUSED HETEROCYCLIC INHIBITORS OF FACTOR XA

CROSS-REFERENCE TO RELATED APPLICATIONS

This application claims the priority benefit of U.S. Provisional Application No. 60/282,438, filed Apr. 9, 2001, which is expressly incorporated fully herein by reference.

FIELD OF THE INVENTION

This invention relates generally to a novel class of fused heterocycles, which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

WO99/62904 illustrates Factor Xa inhibitors that incorporate a five-membered ring heterocycle such as the example shown below.

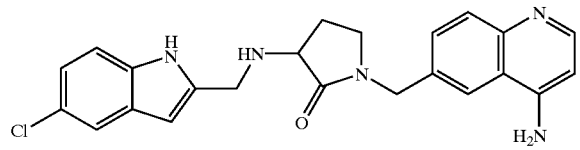

WO00/475631 describes Factor Xa inhibitors that are seven-membered ring lactams of the general structure shown below.

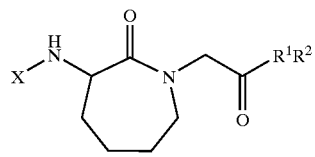

WO99/50257 provides compounds of the general formula shown below as inhibitors of Factor Xa.

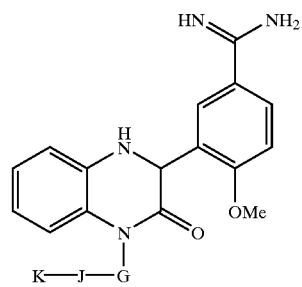

None of the above references teaches or suggests the compounds of the present invention that are described in detail below.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S, Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel fused heterocycles that are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide a novel method of treating a patient in need of thromboembolic disorder treatment, comprising: administering a compound of the present invention or a pharmaceutically acceptable salt form thereof in an amount effective to treat a thromboembolic disorder.

It is another object of the present invention to provide a novel method, comprising: administering a compound of the present invention or a pharmaceutically acceptable salt form thereof in an amount effective to treat a thromboembolic disorder.

It is another object of the present invention to provide novel fused heterocycles for use in therapy.

It is another object of the present invention to provide the use of novel fused heterocycles for the manufacture of a medicament for the treatment of a thromboembolic disorder.

These and other objects, which will become apparent during the following detailed description, have been achieved by the inventors' discovery that the presently claimed fused heterocyclic compounds, or pharmaceutically acceptable salt or prodrug forms thereof, are effective factor Xa inhibitors.

DETAILED DESCRIPTION OF PREFERRED EMBODIMENTS

[1] Thus, in an embodiment, the present invention provides a novel compound of Formula (I) or Formula (II):

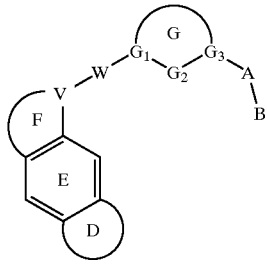

(I)

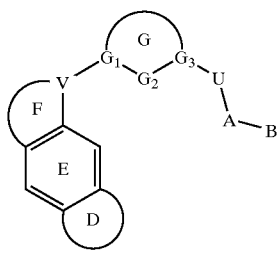

(II)

or a stereoisomer or pharmaceutically acceptable salt form thereof, wherein:

ring D, including the two atoms of ring E to which it is attached, is a 5–6 membered non-aromatic ring consisting of carbon atoms, 0–1 double bonds, and 0–2 heteroatoms selected from the group consisting of N, O, and $S(O)_p$, and ring D is substituted with 0–2 $R^1$, provided that when ring D is unsubstituted, it consists of at least one heteroatom;

alternatively, ring D, including the two atoms of ring E to which it is attached, is a 5–6 membered aromatic system consisting of carbon atoms and 0–2 heteroatoms selected from the group consisting of N, O, and $S(O)_p$, and ring D is substituted with 0–2 $R^1$, provided that when ring D is unsubstituted, it consists of at least one heteroatom;

E is selected from phenyl, pyridyl, pyrimidyl, pyrazinyl, and pyridazinyl, and is substituted with 0–1 $R^1$;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, thiazolyl, thienyl and trizaolyl, and ring E is substituted with 0–2 $R^a$;

$R^a$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $C(O)NR^7R^8$, $(CR^8R^9)_rNR^7R^8$, SH, $SCH_3$, $SCH_2CH_3$, $SCH(CH_3)_2$, $SCH_2CH_2CH_3$, $S(O)R^{3b}$, $S(O)_2R^{3a}$, $S(O)_2NR^2R^{2a}$, and $OCF_3$;

alternatively, two $R^a$s combine to form methylenedioxy or ethylenedioxy;

alternatively, ring D is absent and ring E is selected from phenyl, pyridyl, pyrimidyl, pyrazinyl, pyridazinyl, and thienyl, and ring E is substituted with 1 R and with a 5–6 membered aromatic heterocycle consisting of: carbon atoms and 1–4 heteroatoms selected from the group consisting of N, O, and $S(O)_p$ substituted with 0–1 carbonyl groups and 0–2 $R^1$;

ring F completes a 5–7 membered heterocycle consisting of carbon atoms, 1–3 heteroatoms selected from the group consisting of N, NH, O, and —$S(O)_p$—, 0–2 additional double bonds, and 0–2 carbonyl groups, provided that other than a O—O, O—S, or S—S bond is present in the ring and ring F is substituted with 0–1 $R^{4c}$;

ring G completes a 5–7 membered non-aromatic heterocycle consisting of carbon atoms, 1–3 heteroatoms selected from the group consisting of N, NZ, O, and $S(O)_p$, 0–2 double bonds, and 0–3 carbonyl groups, and ring G is substituted with 0–2 $R^{1a}$, provided that other than a O—O, O—S, or S—S bond is present in ring G;

Z is selected from H, $S(O)_2NHR^3$, $C(O)R^3$, $C(O)NHR^3$, $C(O)OR^{3f}$, $S(O)R^{3f}$, $S(O)_2R^{3f}$,
$C_{1-6}$ alkyl substituted with 0–2 $R^{1a}$;
$C_{2-6}$ alkenyl substituted with 0–2 $R^{1a}$;
$C_{2-6}$ alkynyl substituted with 0–2 $R^{1a}$;
—($C_{0-4}$ alkyl)-$C_{3-10}$-carbocycle substituted with 0–3 $R^{1a}$;
—($C_{0-4}$ alkyl)-5–12 membered-heterocycle substituted with 0–3 $R^{1a}$;

$G_1$ is selected from C, CH, and N;
$G_2$ is selected from CH, $CH_2$, C(O), O, $S(O)_p$, N, and NH;
$G_3$ is selected from C, CH, and N;

A is selected from:
$C_{3-10}$ carbocycle substituted with 0–2 $R^4$, and
5–12 membered heterocycle consisting of carbon atoms and from 1–4 heteroatoms selected from the group consisting of N, O, and S and substituted with 0–2 $R^4$;

B is selected from: Y, X—Y, $(CH_2)_{0-2}C(O)NR^2R^{2a}$, $(CH_2)_{0-2}NR^2R^{2a}$, $C(=NR^2)NR^2R^{2a}$, and $NR^2C(=NR^2)NR^2R^{2a}$, provided that $G_3$ and B are attached to different atoms on A;

X is selected from —$(CR^2R^{2a})_{1-4}$—, —$CR^2(CR^2R^{2b})(CH_2)_t$—, —C(O)—, —$C(=NR^{1c})$—, —$CR^2(NR^2R^{2a})$—, —$CR^2(OR^2)$—, —$CR^2(SR^2)$—, —$C(O)CR^2R^{2a}$—, —$CR^2R^{2a}C(O)$, —S—, —S(O)—, —$S(O)_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
—$(CH_2)_rNR^2R^{2a}$;
$C_{3-10}$ carbocycle substituted with 0–2 $R^{4a}$; and
5–10 membered heterocycle consisting of carbon atoms and from 1–4 heteroatoms selected from the group consisting of N, O, and S and substituted with 0–2 $R^{4a}$;

provided that X—Y do not form a N—N, O—N, or S—N bond;

V is selected from C, CH, and N;
U is a bond or is selected from $CHR^{3b}$, C(O), O, $S(O)_p$, $NR^{3b}$, $C(O)NR^3$, $NR^3C(O)$, $C(O)CH_2$, $CH_2C(O)$, $S(O)_pNR^3$, $NR^3S(O)_p$, $OCH_2$, $CH_2O$, $NR^{3b}CH_2$, and $CH_2NR^{3b}$;

provided that when ring D is absent, U is other than a bond;

W is a bond or is selected from $CHR^{3b}$, C(O), O, $S(O)_p$, $NR^{3b}$, $C(O)NR^3$, $NR^3C(O)$, $C(O)CH_2$, $CH_2C(O)$, $S(O)_pNR^3$, $NR^3S(O)_p$, $OCH_2$, $CH_2O$, $NR^{3b}CH_2$, and $CH_2NR^{3b}$;

provided that when ring D is absent, W is a bond;

$R^1$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_tNR^7R^8$, $(CR^8R^9)_tC(O)NR^7R^8$, $(CR^8R^9)_tOR^{3a}$, $(CR^8R^9)_tNR^7C(O)R^7$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^{3c}$, $(CR^8R^9)_tS(O)_2R^{3c}$, and $OCF_3$;

$R^{1a}$ is selected from H, —$(CH_2)_r$—$R^{1b}$, —CH=CH—$R^{1b}$, $NCH_2R^{1c}$, $NR^2R^{2a}$, $OCH_2R^{1c}$, $SCH_2R^{1c}$, $NH(CH_2)_2$ $(CH_2)_rR^{1b}$, $O(CH_2)_2(CH_2)_rR^{1b}$, $S(CH_2)_2(CH_2)_rR^{1b}$, $S(O)_p(CH_2)_rR^{1d}$, $O(CH_2)_rR^{1d}$, $NR^3(CH_2)_rR^{1d}$, $OC(O)$ $NR^3(CH_2)_rR^{1d}$, $NR^3C(O)NR^3(CH_2)_rR^{1d}$, $NR^3C(O)O$ $(CH_2)_rR^{1d}$, and $NR^3C(O)(CH_2)_rR^{1d}$, provided that $R^{1a}$ forms other than an N-halo, N—N, N—S, N—O, or N—CN bond;

alternatively, when two $R^{1a}$s are attached to adjacent atoms, together with the atoms to which they are attached they form a 5–7 membered ring consisting of: carbon atoms and 0–2 heteroatoms selected from the group consisting of N, O, and $S(O)_p$, this ring being substituted with 0–2 $R^{4b}$ and 0–1 Z, and comprising: 0–3 double bonds;

$R^{1b}$ is selected from H, $C_{1-13}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2$ $(CH_2)_rOR^2$, $SO_2NR^2R^{2a}$, $NR^2SO_2R^{2b}$, $C_{3-10}$ carbocycle substituted with 0–2 $R^{4a}$, and 5–10 membered heterocycle consisting of carbon atoms and from 1–4 heteroatoms selected from the group consisting of N, O, and $S(O)_p$, substituted with 0–2 $R^{4a}$, provided that $R^{1b}$ forms other than an N-halo, N—N, N—S, N—O, or N—CN bond with the group to which it is attached;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^{1d}$ is selected from $C_{3-6}$ carbocycle substituted with 0–2 $R^{4a}$, and 5–10 membered heterocycle consisting of carbon atoms and from 1–4 heteroatoms selected from the group consisting of N, O, and $S(O)_p$, and substituted with 0–2 $R^{4a}$, provided that $R^{1d}$ forms other than an N—N, N—S, or N—O bond;

$R^2$ and $R^{2a}$, at each occurrence, are independently selected from H, $CF_3$, $C_{1-6}$ alkyl, benzyl;

—$(CH_2)_r$—$C_{3-10}$ carbocycle substituted with 0–2 $R^{4b}$; and

—$(CH_2)_r$-5–6 membered heterocycle consisting of carbon atoms and from 1–4 heteroatoms selected from the group consisting of N, O, and $S(O)_p$, and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$ and $R^{2c}$, at each occurrence, are independent selected from $CF_3$, OH, $C_{1-4}$ alkoxy, $C_{1-6}$ alkyl, benzyl;

—$(CH_2)_r$—$C_{3-10}$ carbocycle substituted with 0–2 $R^{4b}$; and

—$(CH_2)_r$-5–6 membered heterocycle consisting of carbon atoms and from 1–4 heteroatoms selected from the group consisting of N, O, and $S(O)_p$, and substituted with 0–2 $R^{4b}$;

$R^3$ and $R^{3a}$, at each occurrence, is independently selected from H, $C_{1-4}$ alkyl, benzyl and phenyl;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-cycloalkyl substituted with 0–3 $R^{1a}$, —$(C_{0-4}$ alkyl)-heterocycle substituted with 0–3 $R^{1a}$, —$(C_{0-4}$ alkyl)-aryl substituted with 0–3 $R^{1a}$, and —$(C_{0-4}$ alkyl)-heteroaryl substituted with 0–3 $R^{1a}$;

$R^{3c}$, at each occurrence, is selected from $C_{1-4}$ alkyl, benzyl, and phenyl;

$R^{3d}$, at each occurrence, is selected from H, $C_{1-4}$ alkyl, $C_{1-4}$ alkyl-phenyl, and $C(=O)R^{3c}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)$ $NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1c}$, $OCH_2R^{1c}$, $SCH_2R^{1c}$, $N(CH_2)_2(CH_2)_rR^{1b}$, $O(CH_2)_2(CH_2)_rR^{1b}$, and $S(CH_2)_2(CH_2)_rR^{1b}$;

alternatively, one $R^4$ is a $(CR^3R^{3a})_r$-5–6 membered aromatic heterocycle consisting of: carbon atoms and 1–4 heteroatoms selected from the group consisting of N, O, and $S(O)_p$;

$R^{4a}$, at each occurrence, is selected from H, =O, $(CR^3R^{3a})_rOR^2$, $(CR^3R^{3a})_rF$, $(CR^3R^{3a})_rBr$, $(CR^3R^{3a})_rCl$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NH(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rC(O)NHSO_2$—$C_{1-4}$ alkyl, $(CR^3R^{3a})_rNR^2SO_2R^5$, $(CR^3R^{3a})_rS(O)_pR^5$, $(CR^3R^{3a})_r(CF_2)_rCF_3$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$, and substituted with 0–1 $R^5$;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_r$—$C(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_rCF_3$;

$R^{4c}$ is selected from H, $C_{1-4}$ alkyl, —$(CH_2)_uOR^{3b}$, —$(CH_2)_uNR^{3b}R^{3b}$, —$CH_2)_uC(O)R^{3b}$, —$(CH_2)_uCO_2R^{3b}$, —$(CH_2)_uNR^{3b}R^{3b}$, —$(CH_2)_uSO_2NR^{3b}R^{3b}$, —$(CH_2)_uNHSO_2R^{3b}$, and $(CR^3R^{3a})_r$-5–6 membered carbocycle substituted with 0–1 $R^5$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $(CF_2)_rCF_3$, phenyl substituted with 0–2 $R^6$, naphthyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl, and —$(CH_2)_n$-phenyl;

alternatively, $R^7$ and $R^8$, when attached to the same nitrogen, combine to form a 5 or 6 membered saturated ring consisting of carbon atoms and 0–2 additional heteroatoms selected from the group consisting of N, O, and $S(O)_p$;

$R^9$, at each occurrence, is selected from H, $C_{1-6}$ alkyl, and —$(CH_2)_n$-phenyl;

n, at each occurrence, is selected from 0, 1, 2, and 3;
p, at each occurrence, is selected from 0, 1, and 2;
r, at each occurrence, is selected from 0, 1, 2, and 3;
t, at each occurrence, is selected from 0, 1, 2, and 3; and,
u, at each occurrence, is selected from 1, 2, and 3.

[2] In another embodiment, the present invention provides a novel compound, wherein:

rings D-E are selected from:

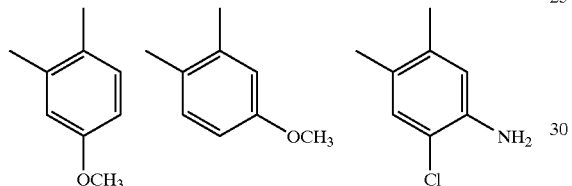
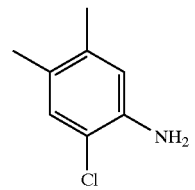
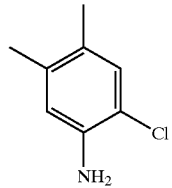
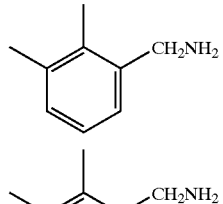
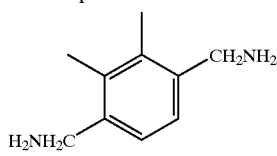
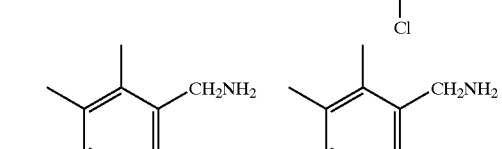

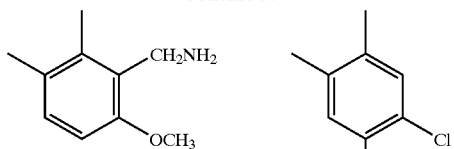
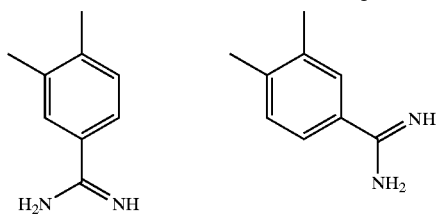
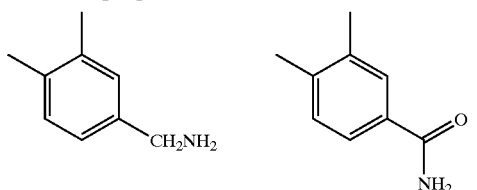
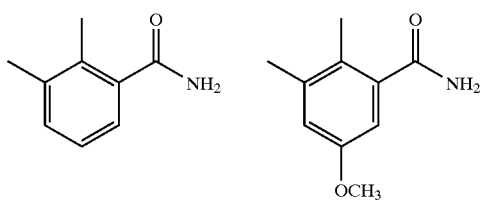
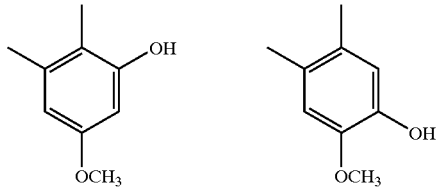
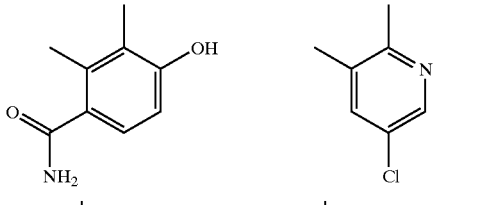
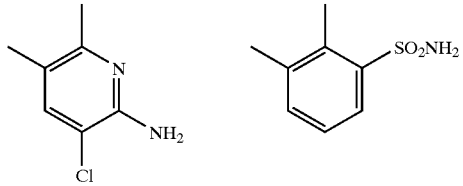
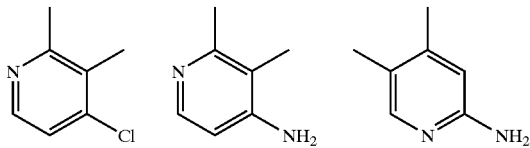

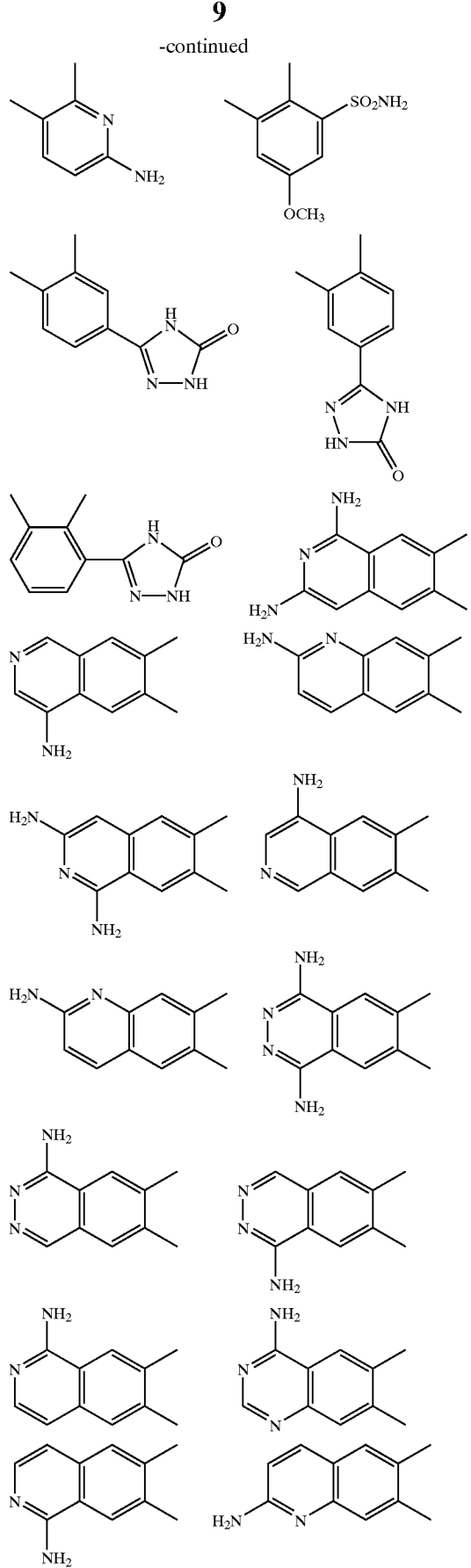
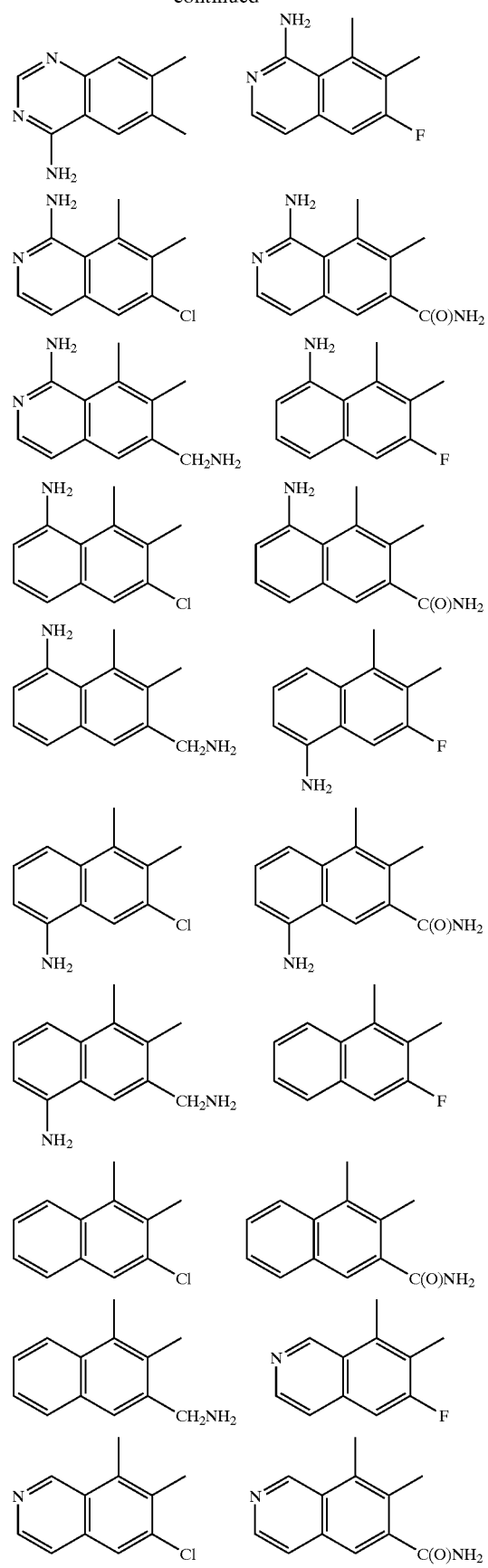

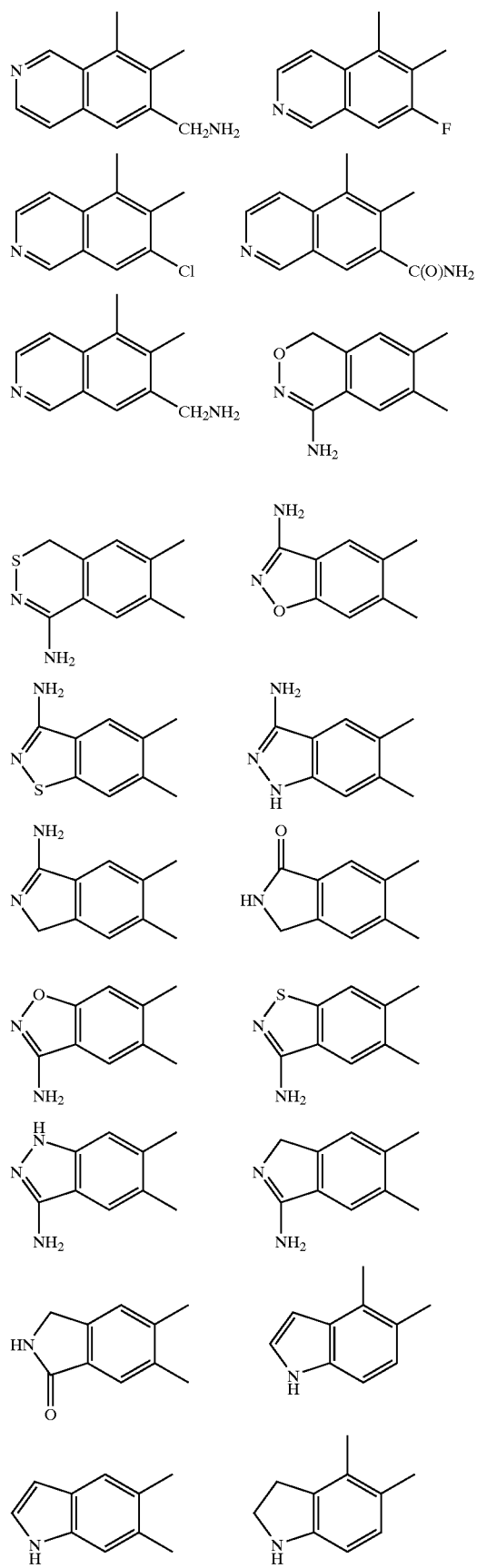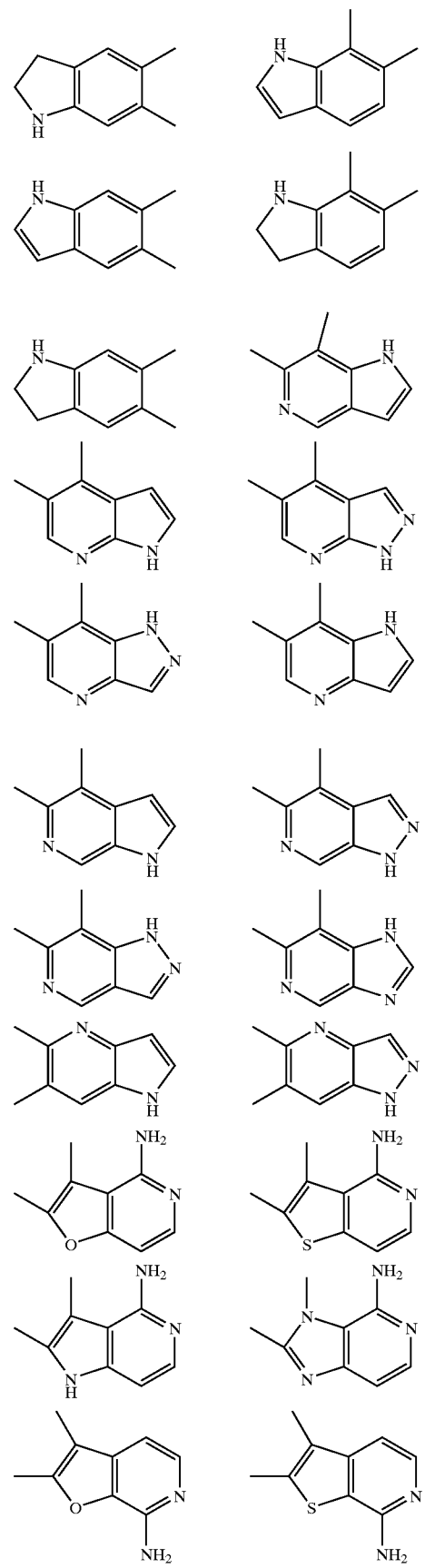

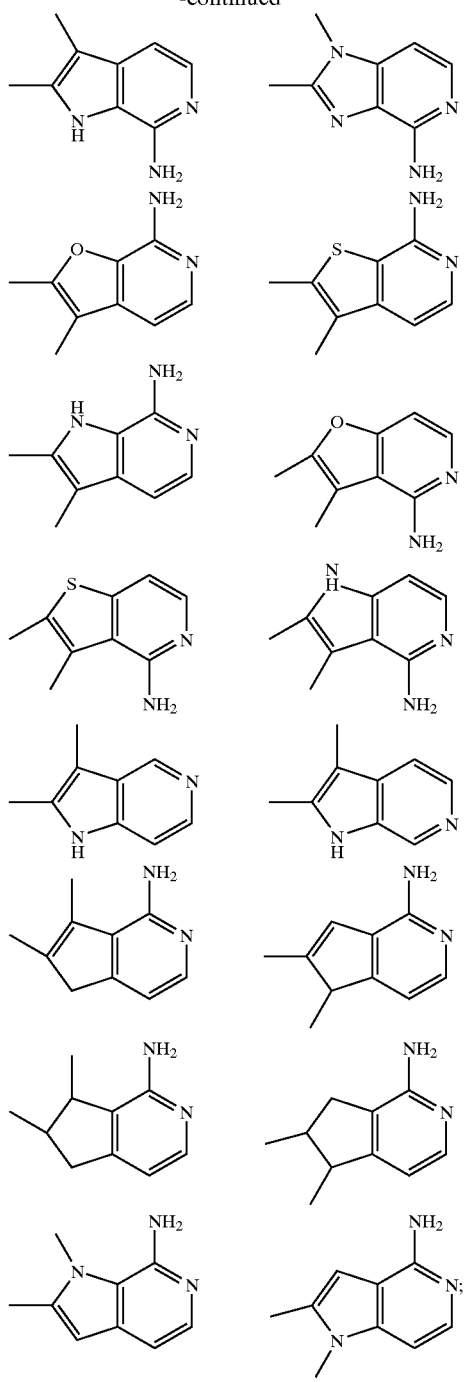
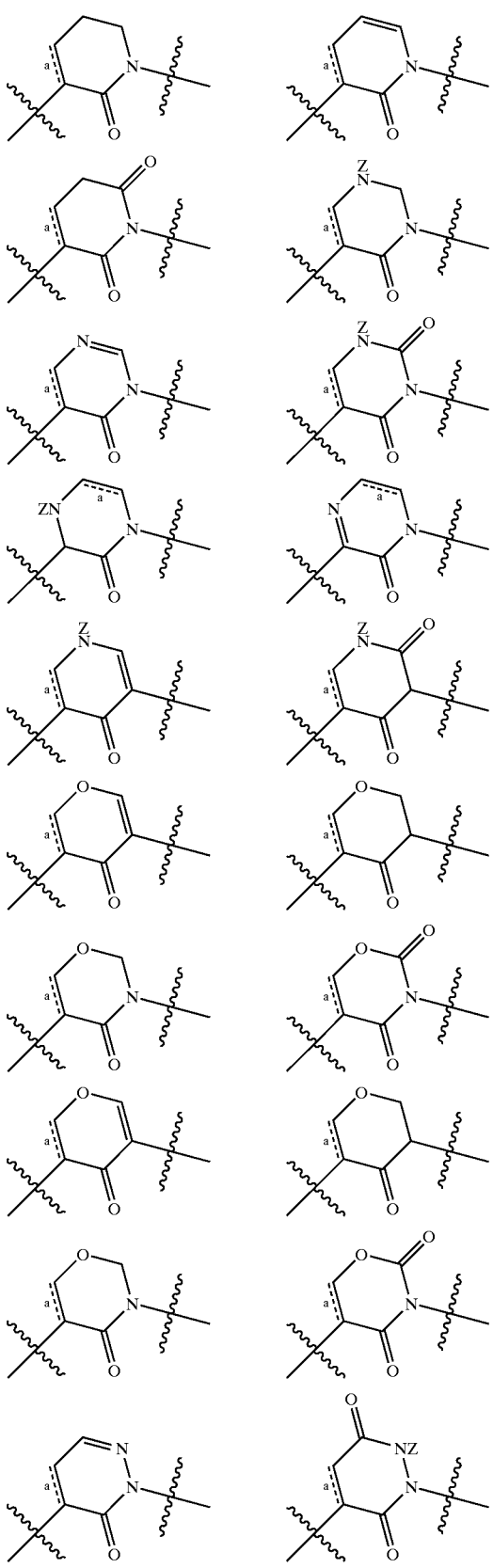

the bridging portion of ring F completes a 5–7 membered heterocycle consisting of carbon atoms, 1–3 heteroatoms selected from the group consisting of N, NH, O, and S, 0–2 additional double bonds, and 0–2 carbonyl groups, provided that other than a O—O, O—S, or S—S bond is present in the ring and the bridging portion of ring F is substituted with 0–1 $R^{4c}$;

ring G is substituted with 0–2 $R^{1a}$ and is selected from the group:

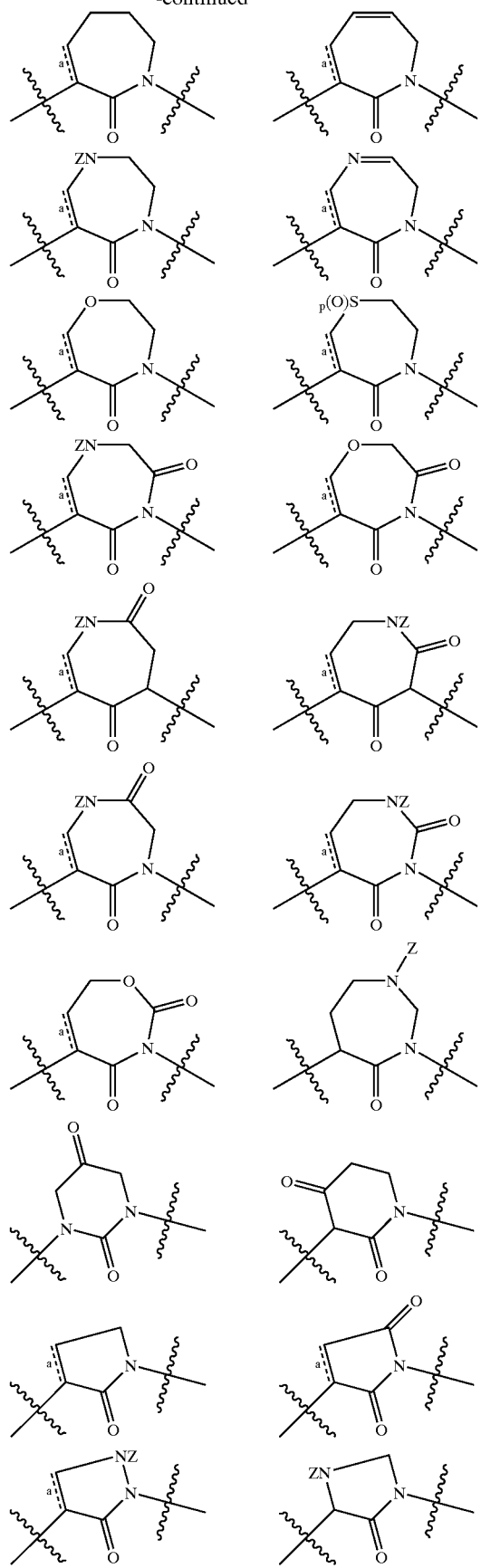
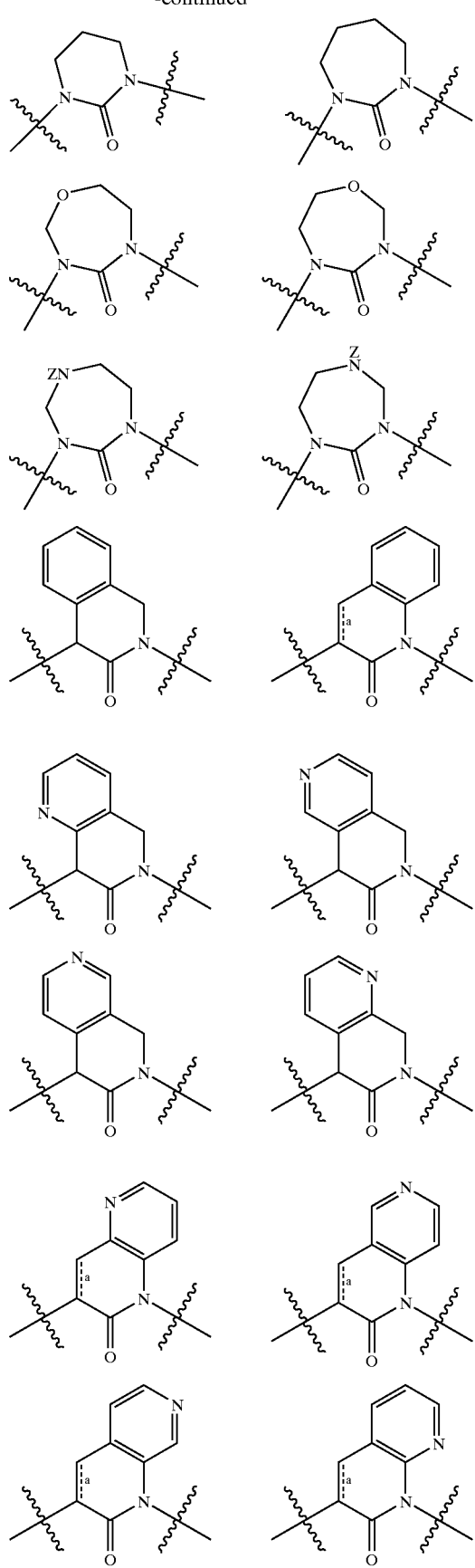

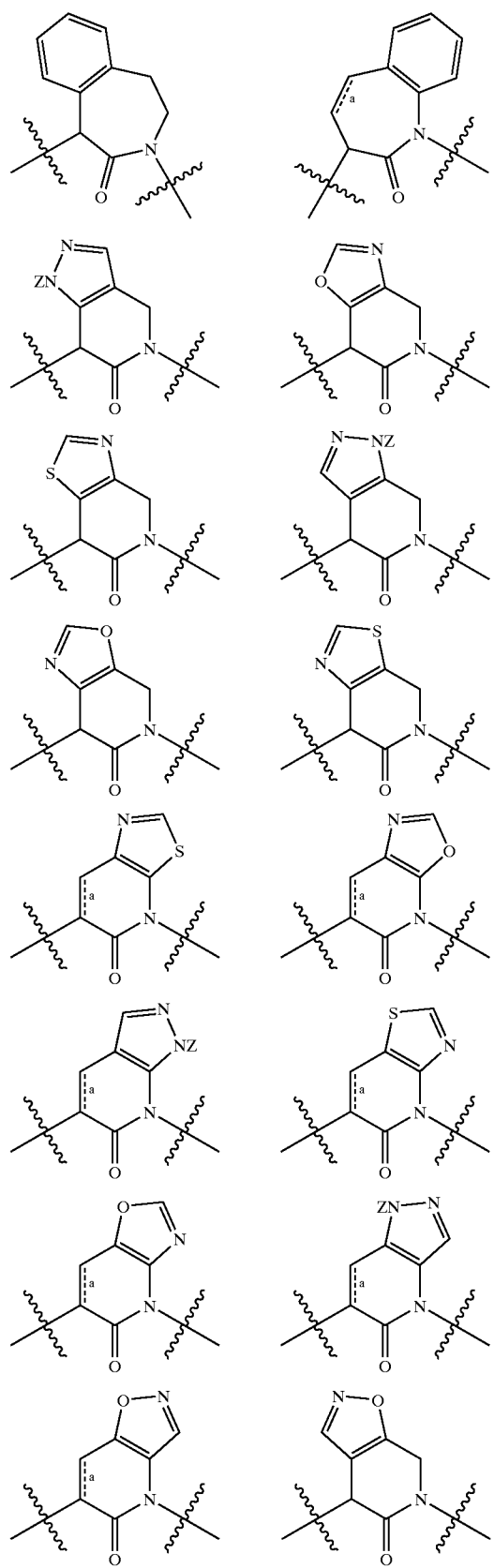
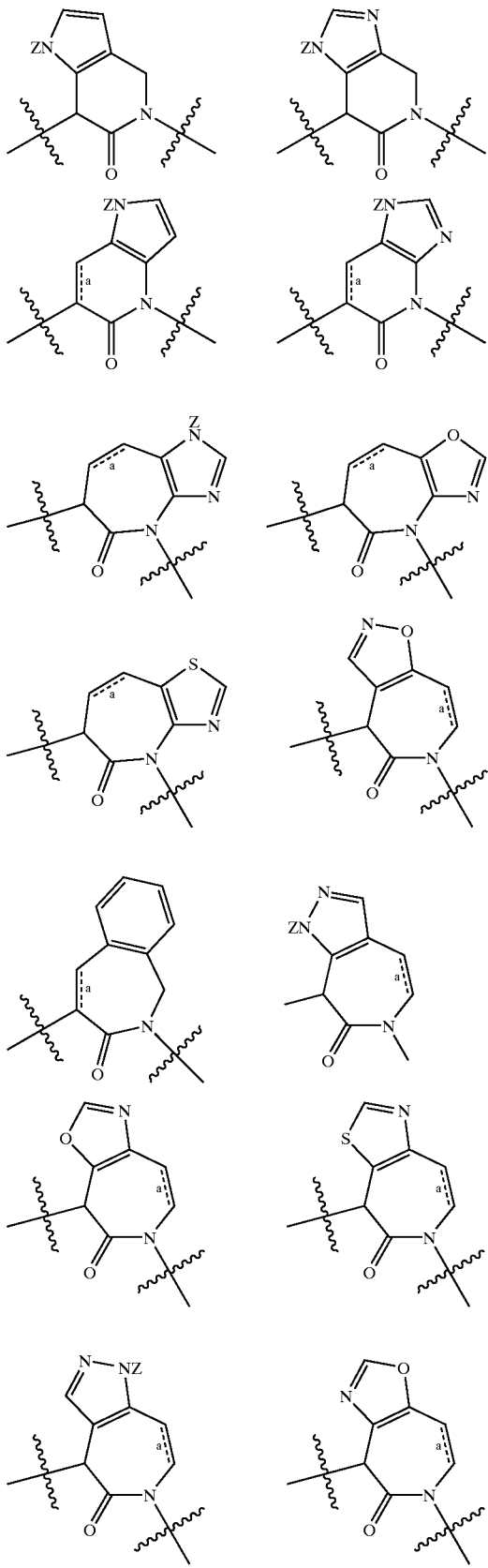

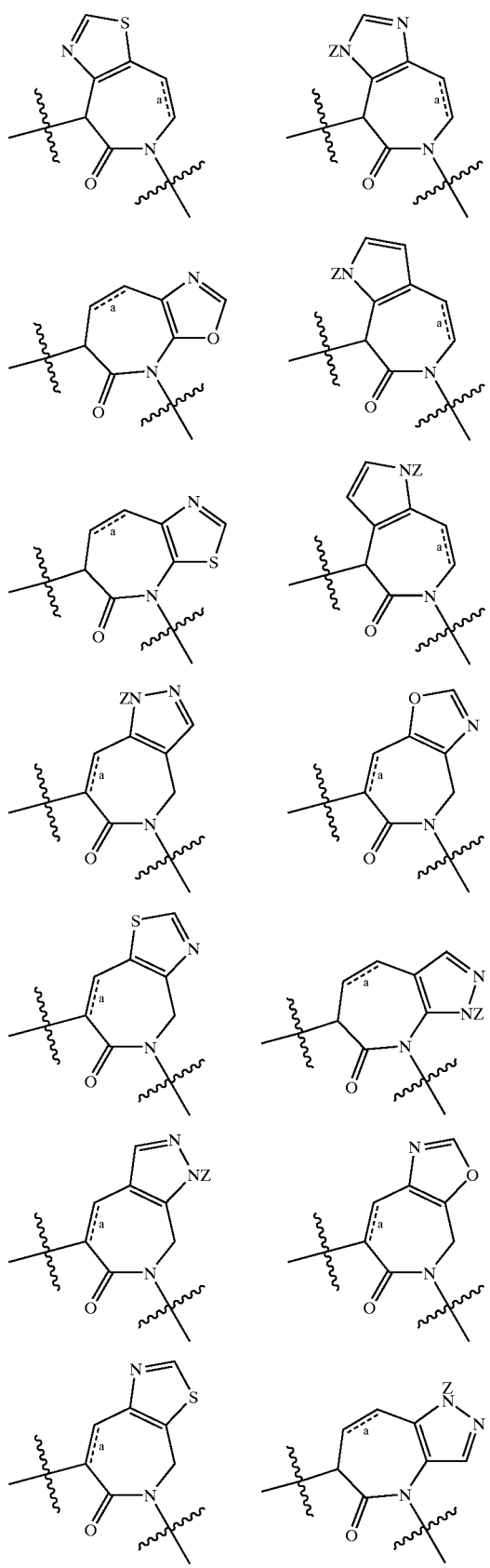
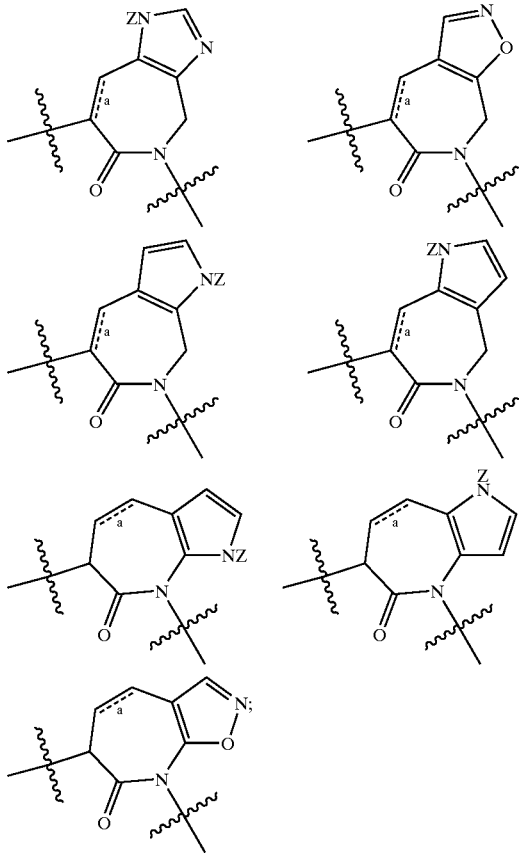

"a" is a single or double bond;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is X—Y or is selected from one of the following carbocyclic and heterocyclic systems which are substituted with 1–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=NR$^{1c}$)—, —CR$^2$(NR$^2$R$^{2a}$)—, —C(O)CR$^2$R$^{2a}$—, —CR$^2$R$^{2a}$C(O), —C(O)NR$^2$—, —NR$^2$C(O)—, —C(O) NR$^2$CR$^2$R$^{2a}$—, —NR$^2$C(O)CR$^2$R$^{2a}$—, —CR$^2$R$^{2a}$C(O) NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is NR$^2$R$^{2a}$, provided that X—Y do not form a N—N or O—N bond;

alternatively, Y is selected from one of the following carbocyclic and heterocycles which are substituted with 0–2 R$^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

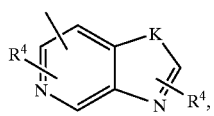 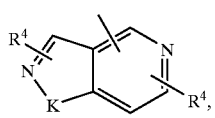

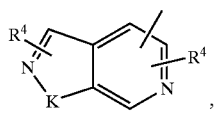 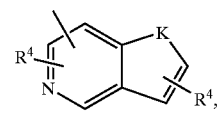

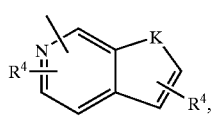 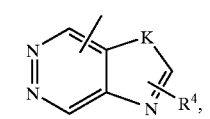

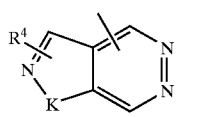 and 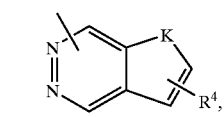

K is selected from O, S, NH, and N;
V is selected from C, CH, and N;
U is a bond or is selected from CH$_2$, C(O), O, S, NH, C(O)NH, NHC(O), C(O)CH$_2$, CH$_2$C(O), S(O)$_p$NH, NHS(O)$_p$, OCH$_2$, CH$_2$O, NHCH$_2$, and CH$_2$NH;
provided that when ring D is absent, U is other than a bond; and
W is a bond or is selected from CHR$^{3b}$, C(O)O, S(O)$_p$, NR$^{3b}$, C(O)NR$^3$, NR$^3$C(O), C(O)CH$_2$, CH$_2$C(O), S(O)$_p$NR$^3$, NR$^3$S(O)$_p$, OCH$_2$, CH$_2$O, NR$^{3b}$CH$_2$, and CH$_2$NR$^{3b}$;
provided that when ring D is absent, W is a bond.

[3] In another embodiment, the present invention provides a novel compound of Formula (Ia) or (IIa):

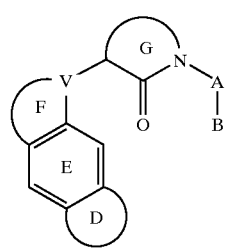 (Ia)

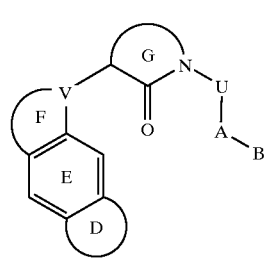 (IIa)

or a stereoisomer or pharmaceutically acceptable salt form thereof, wherein:

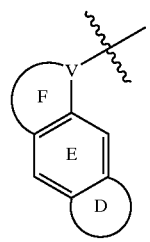 is selected from:

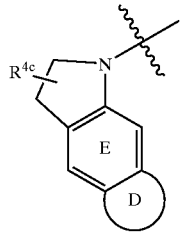 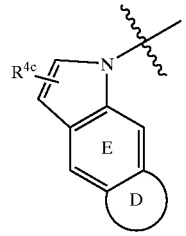

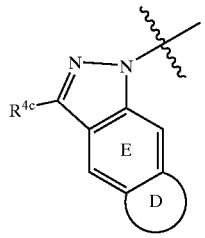 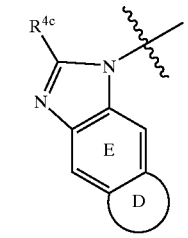

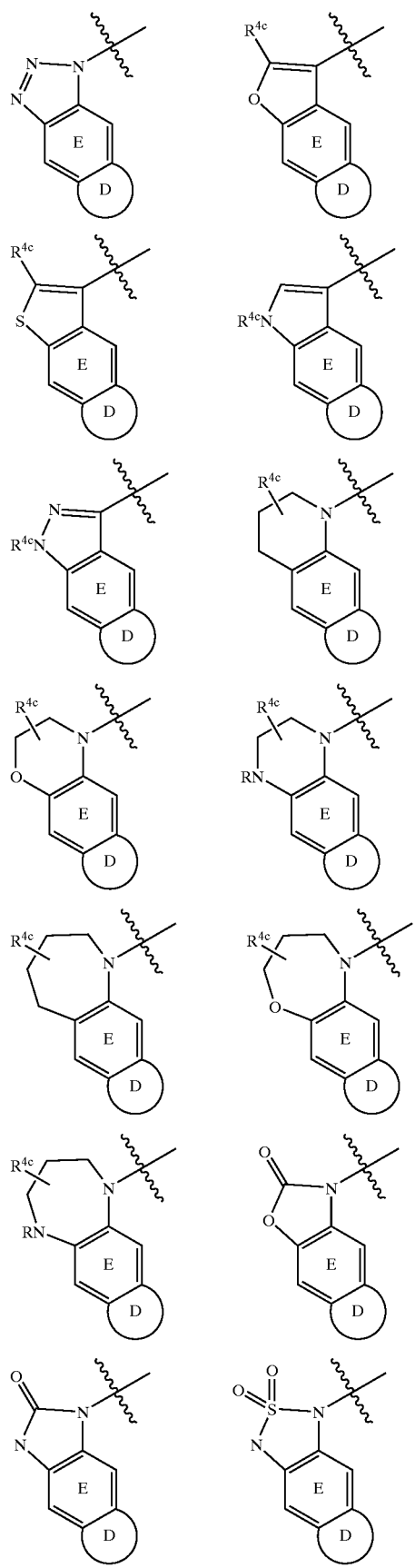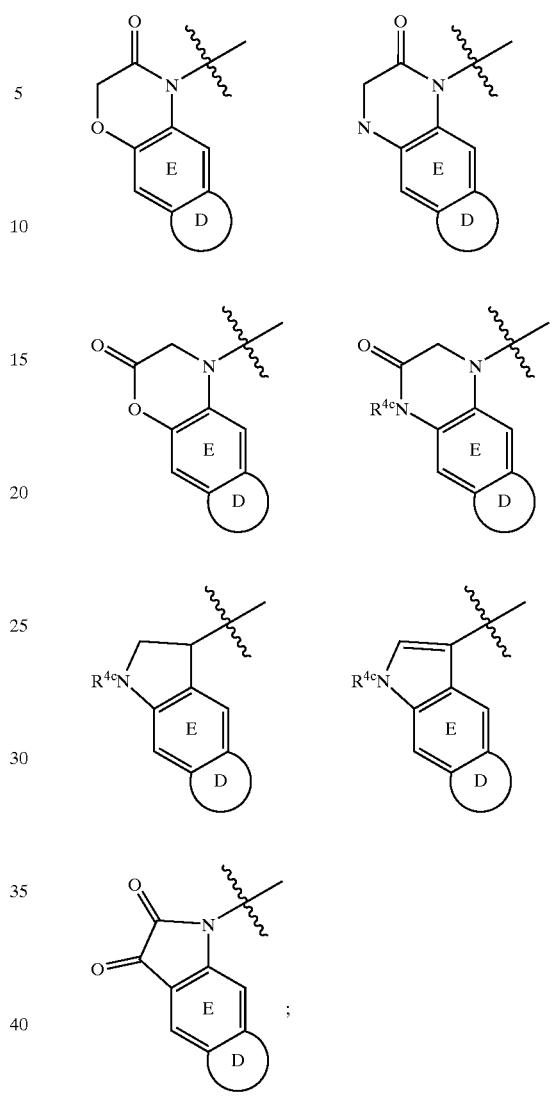
rings D-E are selected from:
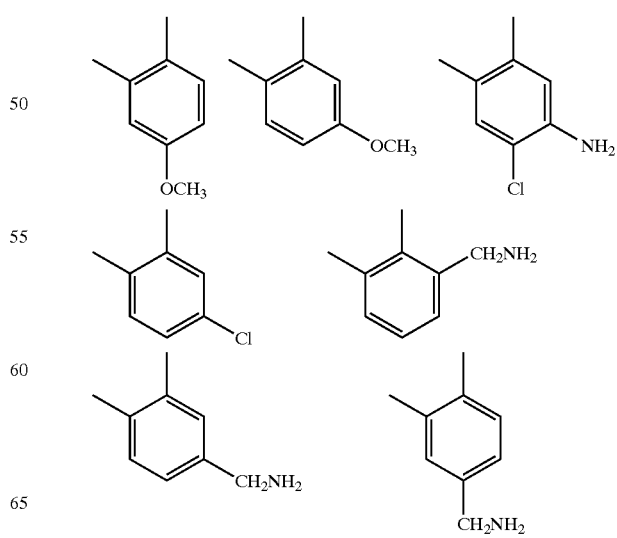

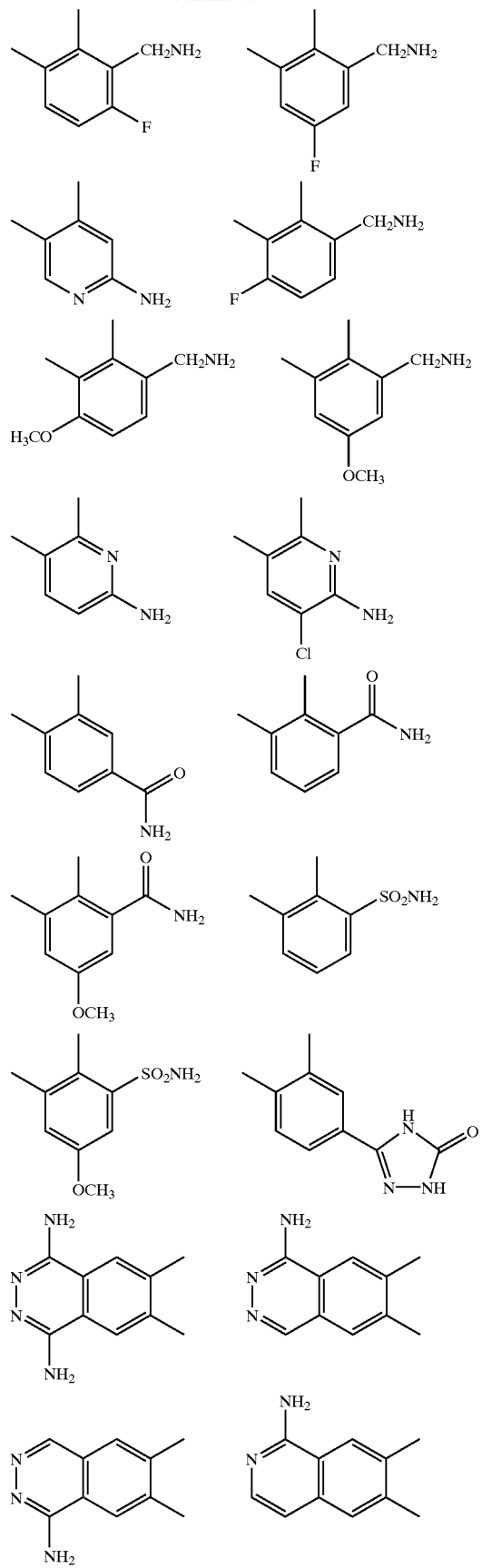
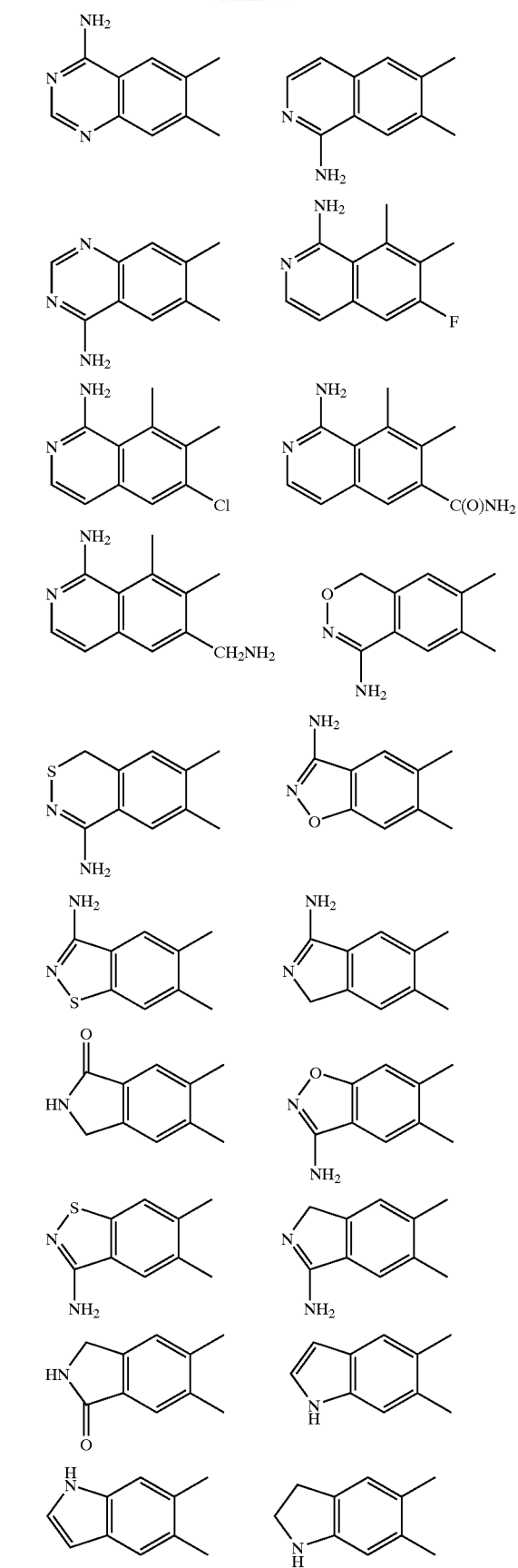

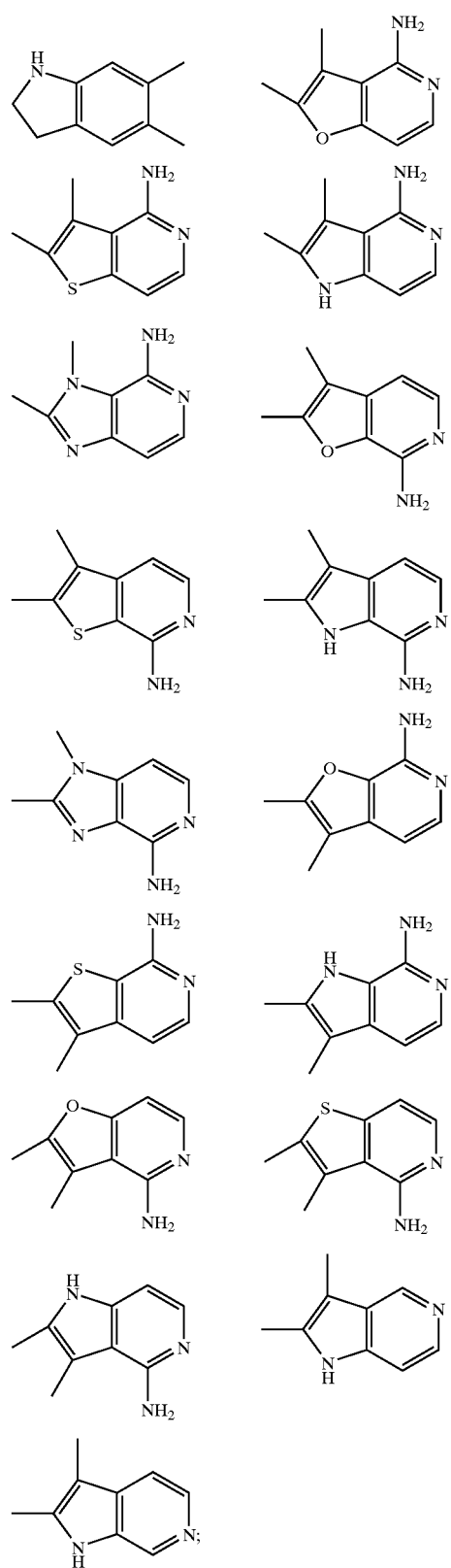
ring G is substituted with 0–2 R[1a] and is selected from the group:
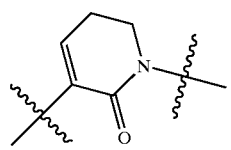 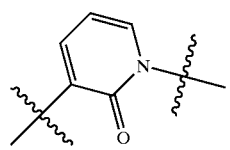
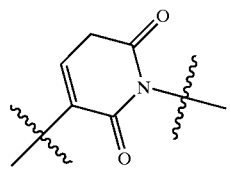 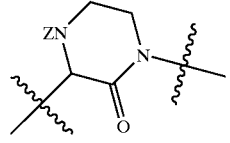
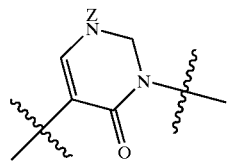 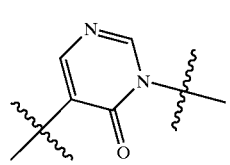
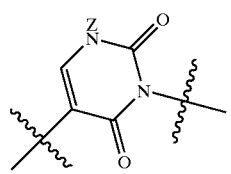 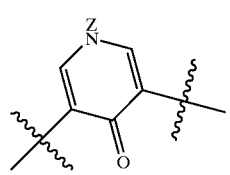
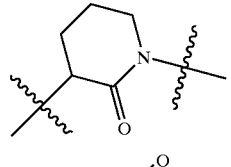 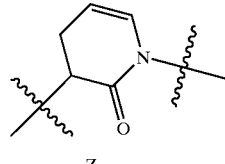
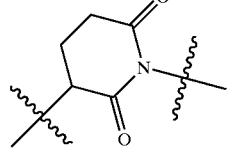 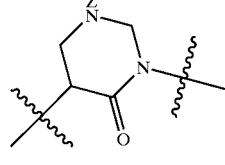
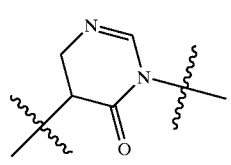 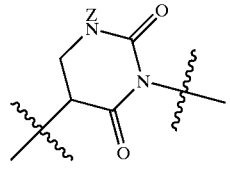
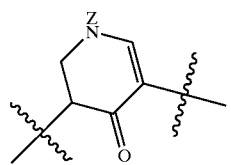 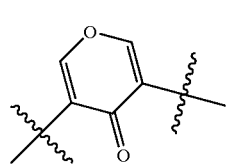
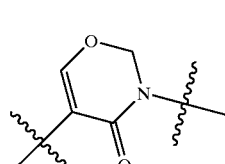 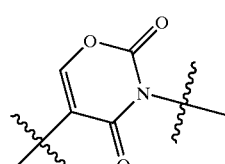
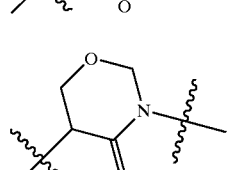 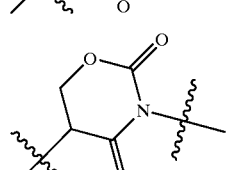
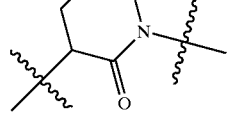 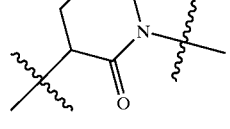

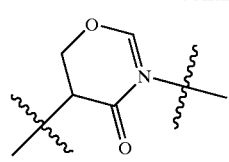
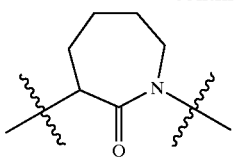
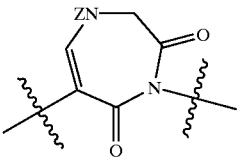
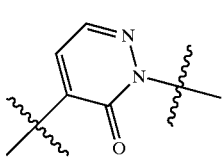
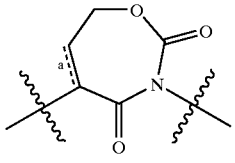
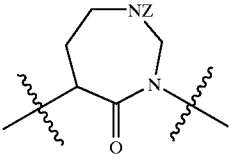
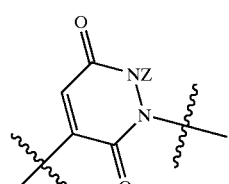
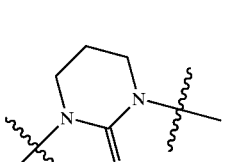
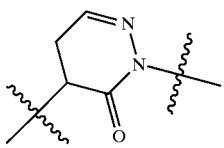
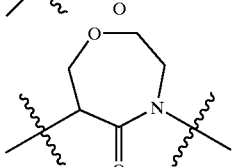
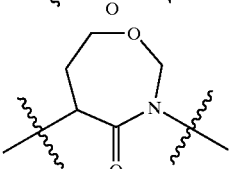
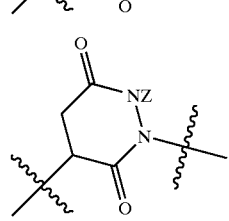
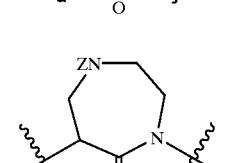
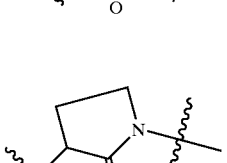
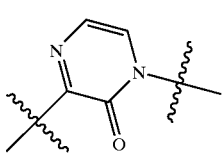
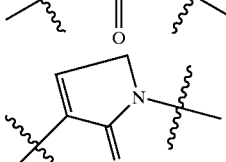
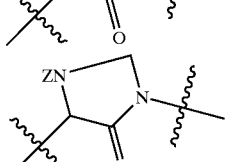
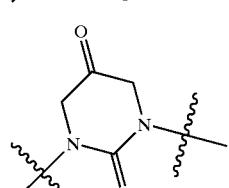
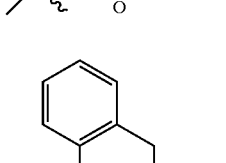
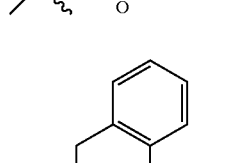
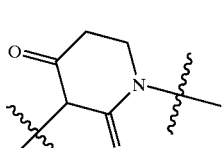
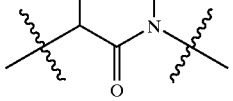
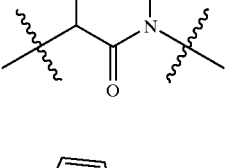
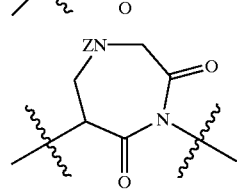
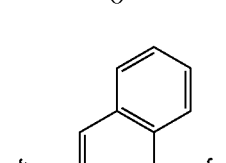
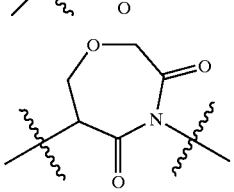
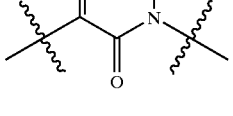
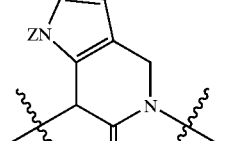
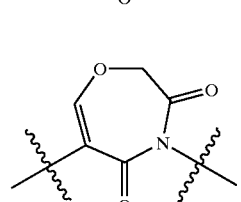
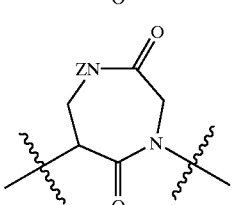
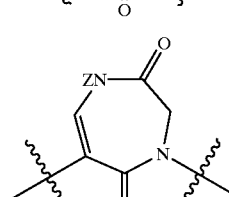
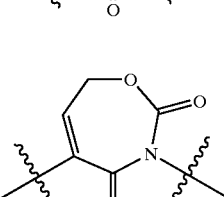
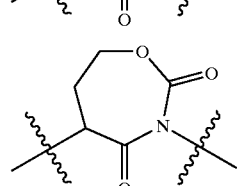
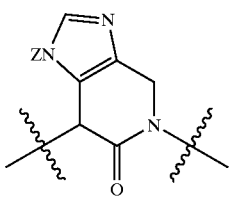
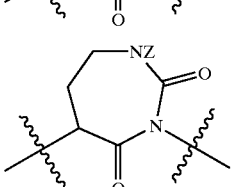
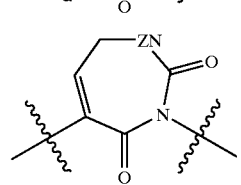
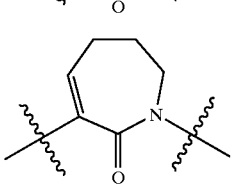
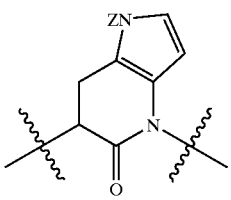

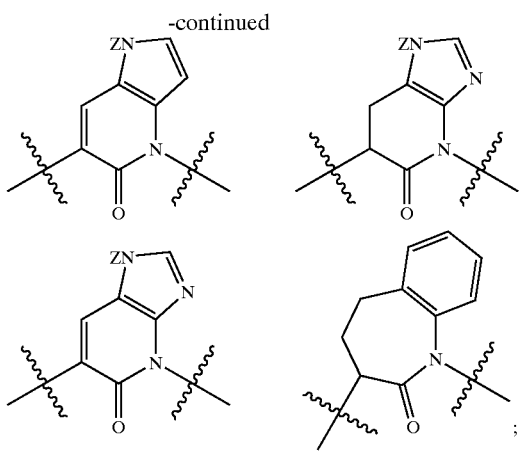

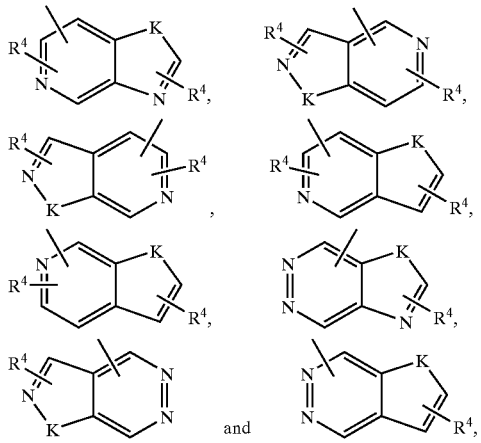

A is selected from one of the following carbocyclic and heterocyclic systems which are substituted with 0–2 $R^4$;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is X—Y or is selected from one of the following carbocyclic and heterocycles which are substituted with 1–2 $R^{4a}$;
  cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=NR$^{1c}$)—, —CR$^2$(NR$^2$R$^{2a}$)—, —C(O)CR$^2$R$^{2a}$—, —CR$^2$R$^{2a}$C(O)—, —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is $(CH_2)_r NR^2 R^{2a}$, provided that X—Y do not form a N—N or O—N bond;

alternatively, Y is selected from one of the following carbocyclic and heterocycles which are substituted with 0–2 $R^{4a}$;
  cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

K is selected from O, S, NH, and N;

V is selected from C, CH, and N; and

U is a bond or is selected from $CH_2$, C(O), O, S, NH, C(O)NH, NHC(O), C(O)CH$_2$, CH$_2$C(O), S(O)$_p$NH, NHS(O)$_p$, OCH$_2$, CH$_2$O, NHCH$_2$, and CH$_2$NH;

provided that when ring D is absent, U is other than a bond.

In another embodiment, the present invention provides a novel compound, wherein:

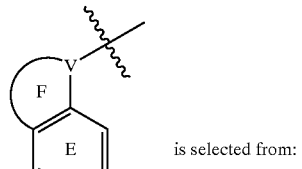 is selected from:

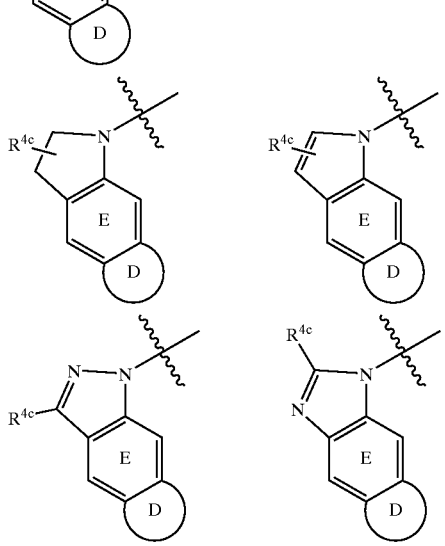

-continued
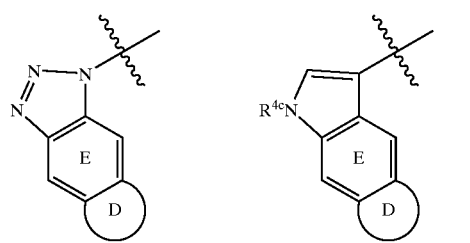
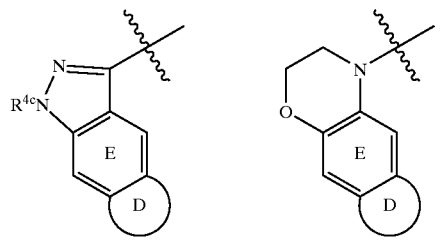
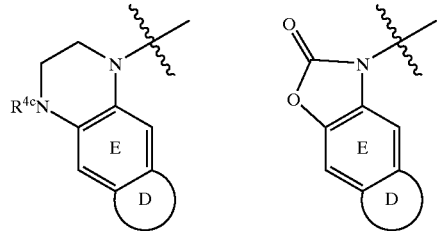
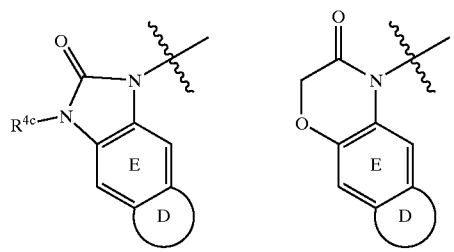
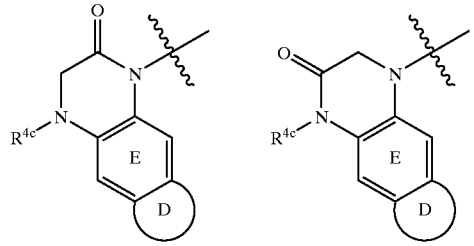
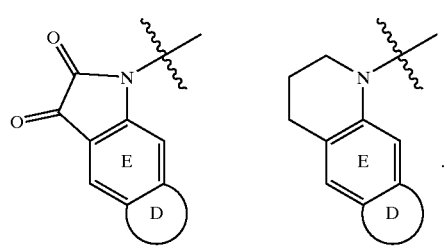
In another embodiment, the present invention provides a novel compound, wherein:
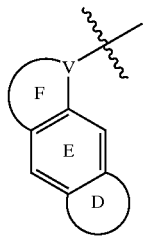 is selected from:
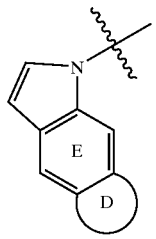 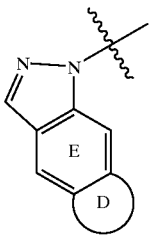
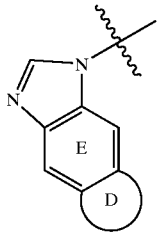 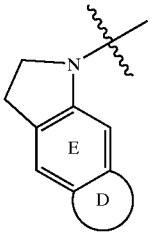
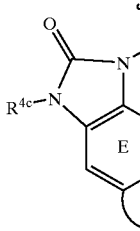 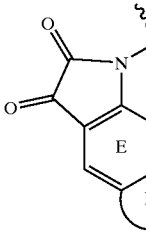
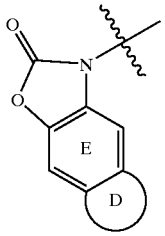 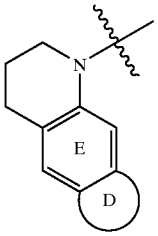
[4] In another embodiment, the present invention provides a novel compound, wherein:
rings D-E are selected from:
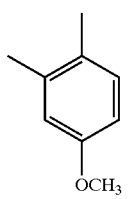 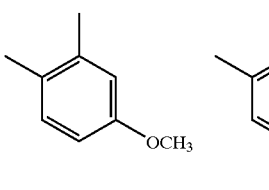 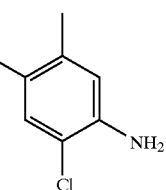

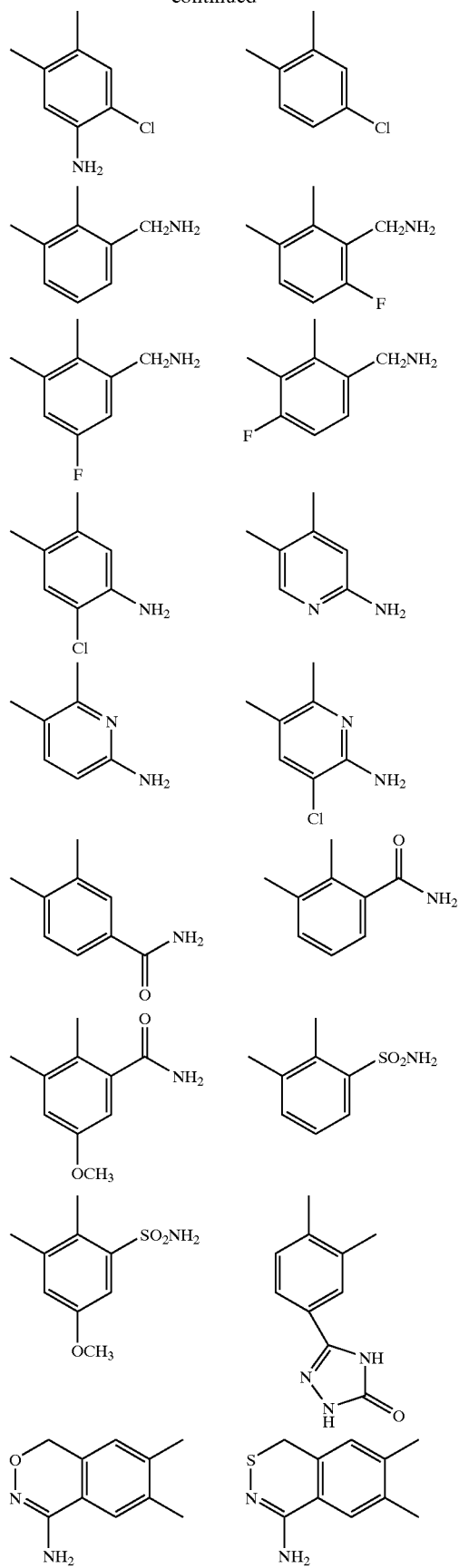
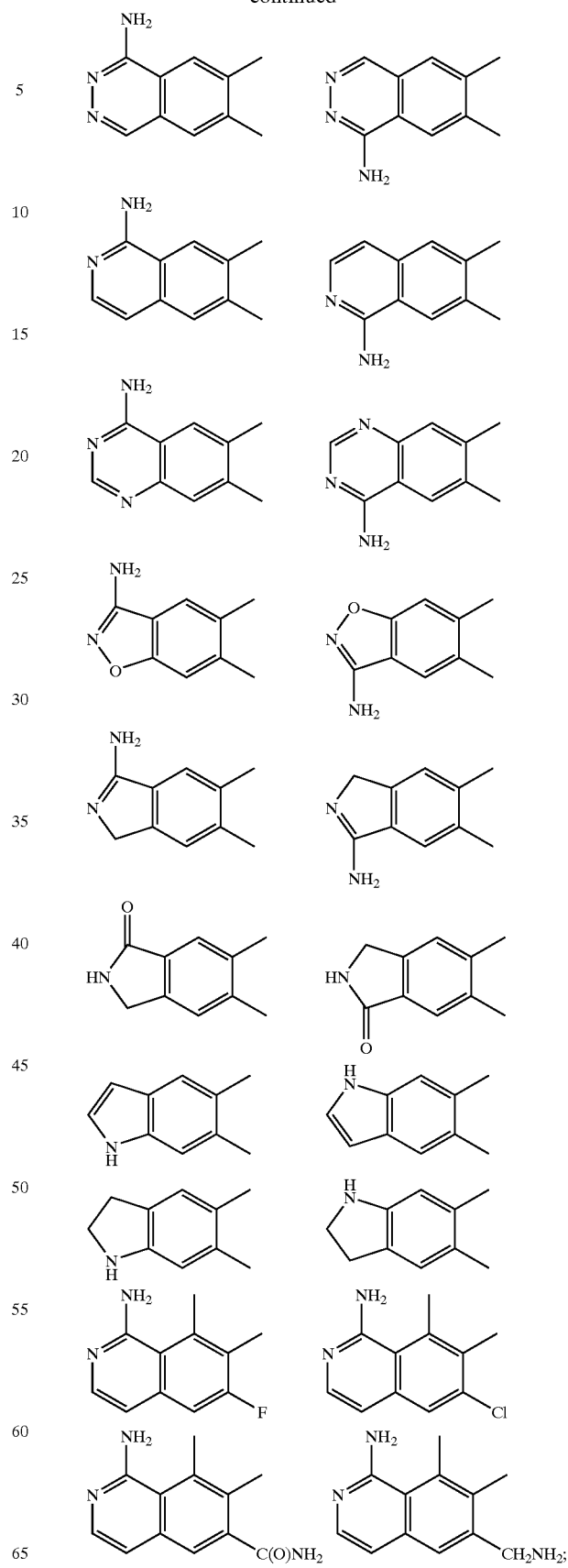

ring G is substituted with 0–1 $R^{1a}$ and is selected from the group:

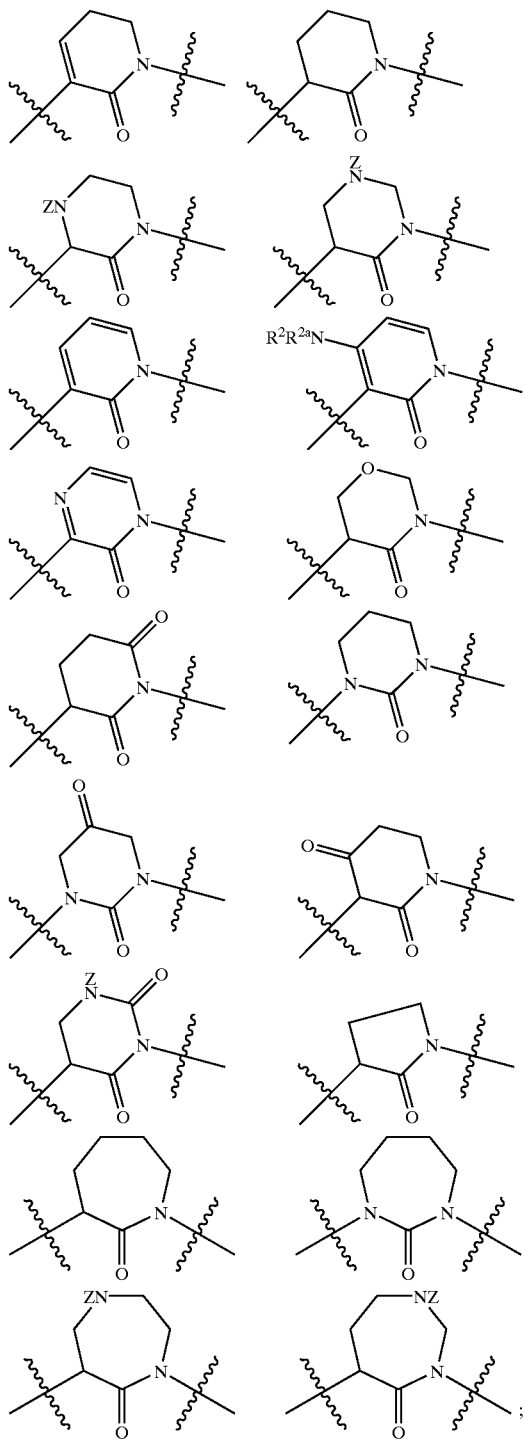

A is selected from one of the following carbocyclic and heterocycles which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is X—Y or is selected from one of the following carbocyclic and heterocycles which are substituted with 1–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=$NR^{1c}$)—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is $(CH_2)_rNR^2R^{2a}$, provided that X—Y do not form a N—N or O—N bond;

alternatively, Y is selected from one of the following carbocyclic and heterocycles which are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl; and alternatively, Y is selected from the following bicyclic heteroaryl ring systems:

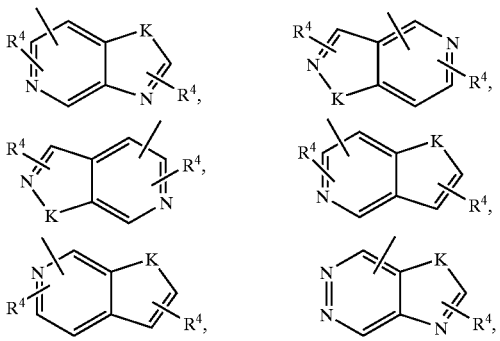

-continued

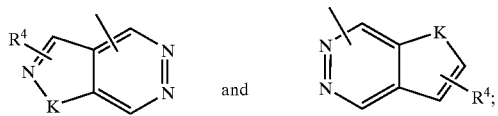

K is selected from O, S, NH, and N.

In another embodiment, the present invention provides a novel compound, wherein:

ring G is substituted with 0–1 $R^{1a}$ and is selected from the group:

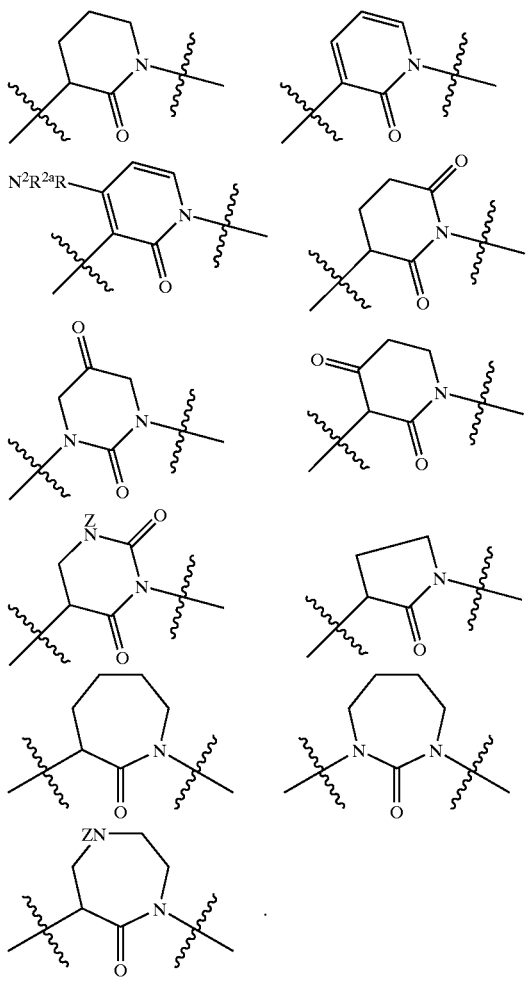

In another embodiment, the present invention provides a novel compound, wherein:

ring G is substituted with 0–1 $R^{1a}$ and is selected from the group:

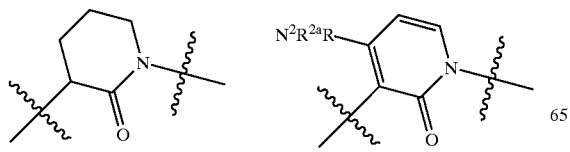

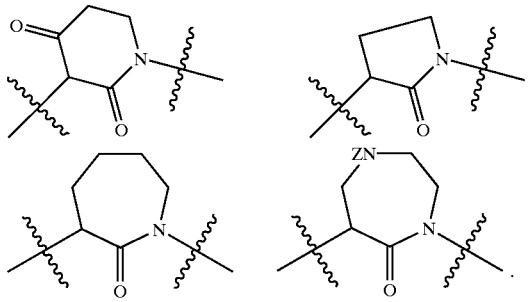

[5] In another embodiment, the present invention provides a novel compound, wherein:

rings D-E are selected from:

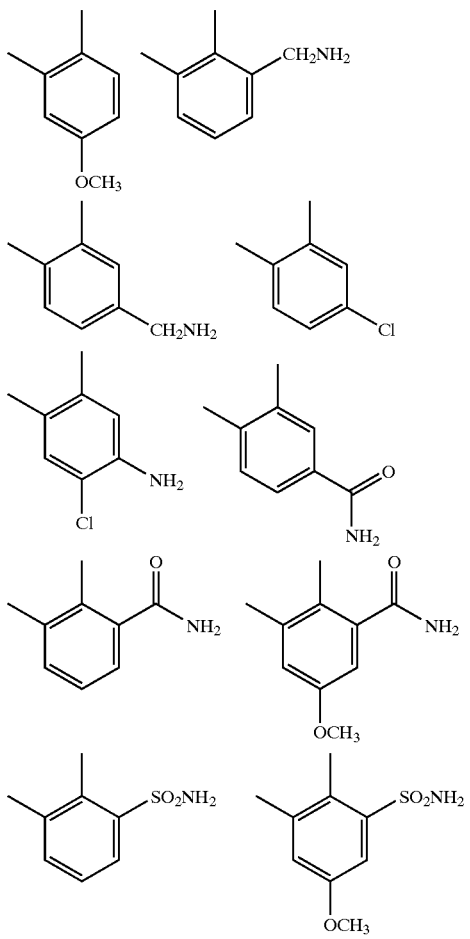

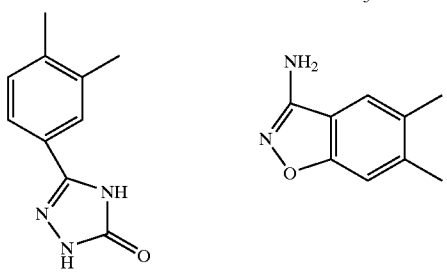

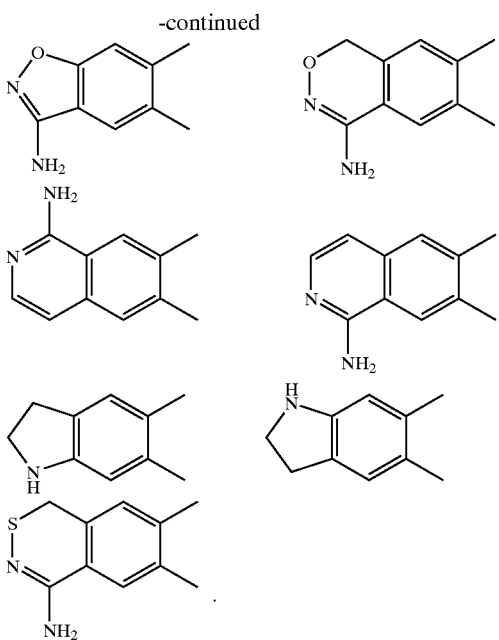

[6] In another embodiment, the present invention provides a novel compound, wherein:

A is selected from phenyl, pyridyl, and pyrimidyl, and is substituted with 0–2 $R^4$; and,
B is selected from X—Y, phenyl, pyrrolidino, morpholino, 1,2,3-triazolyl, imidazolyl, and benzimidazolyl, and is substituted with 0–1 $R^{4a}$;
X is $CH_2$ or $C(O)$;
Y is selected from pyrrolidino and morpholino;
$R^2$, at each occurrence, is selected from H, $CH_3$, $CH_2CH_3$, cyclopropylmethyl, cyclobutyl, and cyclopentyl;
$R^{2a}$, at each occurrence, is H or $CH_3$;
alternatively, $R^2$ and $R^{2a}$, together with the atom to which they are attached, combine to form pyrrolidine substituted with 0–2 $R^{4b}$;
$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;
$R^{4a}$ is selected from $C_{1-4}$ alkyl, $CF_3$, $(CH_2)_rOR^2$, $(CH_2)_rNR^2R^{2a}$, $S(O)_pR^5$, $SO_2NR^2R^{2a}$, and 1-$CF_3$-tetrazol-2-yl;
$R^{4b}$, at each occurrence, is selected from H, $CH_3$, and OH;
$R^{4c}$ is selected from $CO_2CH_3$ and $C(O)NH_2$;
$R^5$, at each occurrence, is selected from $CF_3$, $C_{1-6}$ alkyl, phenyl, and benzyl;
p, at each occurrence, is selected from 0, 1, and 2; and
r, at each occurrence, is selected from 0, 1, and 2.

[7] In another embodiment, the present invention provides a novel compound, wherein:

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and,
B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N,N-diethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(N,N-dimethylaminomethyl)-1-imidazolyl, 2-(N-methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)aminomethyl)phenyl, 2-(N-(4-hydroxypiperidinyl)methyl)phenyl, 2-(N-(3-hydroxypyrrolidinyl)methyl)phenyl, and 2-(N-(2-hydroxyethyl)methylamino)-methyl)phenyl.

[8] In another embodiment, the present invention provides a novel compound or a pharmaceutically acceptable salt form thereof, selected from:
1-{1-[3-fluoro-2'-methylsulfonyl)[1,1'-biphenyl]-4-yl]-2-oxo-3-piperidinyl}-1H-indole-6-carbonitrile;
1-(1-{2'-[(dimethylamino)methyl]-3-fluoro[1,1'-biphenyl]-4-yl}-2-oxo-3-piperidinyl)-6-indoline carbonitrile;
1-{1-[3-fluoro-2'-methylsulfonyl)[1,1'-biphenyl]-4-yl]-2-oxo-3-piperidinyl}-1H-indole-6-carboximidamide;
1-(1-{2'-[(dimethylamino)methyl]-3-fluoro[1,1'-biphenyl]-4-yl}-2-oxo-3-piperidinyl)-6-indoline carboximidamide;
ethyl-1-{1-[3-fluoro-2'-(methylsulfonyl)[1,1'-biphenyl]-4-yl]-2-oxo-3-piperidinyl}-5-methoxy-1H-indole-2-carboxylate;
1-[3-fluoro-2'-(methylsulfonyl)[1,1'-biphenyl]-4-yl]-3-(5-methoxy-1H-indol-1-yl)-2-piperidinone;
N-[3-fluoro-2'-(methylsulfonyl)[1,1'-biphenyl]-4-yl]-3-(6-methoxy-2-oxo-1,3-benzoxazol-3(2H)-yl)-2-oxocyclohexanecarboxamide;
3-{1-[3-fluoro-2'-(methanesulfonyl)-[1,1'-biphenyl]-4-yl]-2-oxo-piperidin-3-yl}-6-methoxy-3H-benzoxazol-2-one;
1-{1-[3-fluoro-2'-(methylsulfonyl)[1,1'-biphenyl]-4-yl]-2-oxo-3-piperidinyl}-1H-indazole-6-carboximidamide;
1-{1-[3-fluoro-2'-(methylsulfonyl)[1,1'-biphenyl]-4-yl]-2-oxo-3-piperidinyl}-3H-benzimidazole-5-carboximidamide;
1-{1-[(3-fluoro-2'-methylsulfonyl)[1,1'-biphenyl]-4-yl]-2-oxo-3-piperidinyl}-1H-benzimidazole-5-carboximidamide;
1-{1-[3-fluoro-2'-(methylsulfonyl)[1,1'-biphenyl]-4-yl]-2-oxo-piperidin-3-yl}-5-methoxy-1H-indole-2,3-dione;
1-[(3-fluoro-2'-methylsulfanyl)[1,1'-biphenyl]-4-yl]-3-(6-methoxy-3,4-dihydro-2H-quinolin-1-yl)piperidin-2-one;
1-[(3-fluoro-2'-methanesulfinyl)[1,1'-biphenyl]-4-yl]-3-(6-methoxy-3,4-dihydro-2H-quinolin-1-yl)piperidin-2-one;
1-{1-[3-fluoro-2'-(methylsulfonyl)[1,1'-biphenyl]-4-yl]-2-oxo-piperidin-3-yl}-5-methoxy-1,3-dihydrobenzimidazol-2-one;
1-1-[3-fluoro-2'-methylsulfonyl-[1,1'-biphenyl]-4-yl]-2-oxo-piperidin-3-yl]-3-isopropyl-5-methoxy-1,3-dihydrobenzimidazol-2-one;
1-[1-[2'-tert-butylsulfamoyl-3-fluoro-[1,1'-biphenyl]-4-yl]-2-oxo-pyrrolidin-3-yl]-1H-indole-6-carboximidamide; and
1-[1-[3-fluoro-2'-sulfamoyl-[1,1'-biphenyl]-4-yl]-2-oxo-pyrrolidin-3-yl]-1H-indole-6-carboximidamide.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another embodiment, the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a novel method, comprising: administering a compound of the present invention or a pharmaceutically acceptable salt form thereof in an amount effective to treat a thromboembolic disorder.

In another embodiment, the present invention provides novel compounds as described above for use in therapy.

In another embodiment, the present invention provides the use of novel compounds as described above for the manufacture of a medicament for the treatment of a thromboembolic disorder.

This invention also encompasses all combinations of preferred aspects of the invention noted herein. It is understood that any and all embodiments of the present invention may be taken in conjunction with any other embodiment to describe additional even more preferred embodiments of the present invention. It is also understood that each and every element of any embodiment is intended to be a separate specific embodiment. Furthermore, any elements of an embodiment are meant to be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. Tautomers of compounds shown or described herein are considered to be part of the present invention.

Preferably, the molecular weight of compounds of the present invention is less than about 500, 550, 600, 650, 700, 750, 800, 850, and 900 grams per mole. More preferably, the molecular weight is less than about 850 grams per mole. Even more preferably, the molecular weight is less than about 750 grams per mole. Still more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e, =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g, $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with MCPBA and or hydrogen peroxides to afford other compounds of this invention. Thus, all shown amines are considered to cover both the shown amine and its N-oxide (N→O) derivative.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]-tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2, 3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Also included are fused ring and Spiro compounds containin g, for example, the above heterocycles.

The term "independently selected from", "independently, at each occurrence" or similar language, means that the labeled R substitution group may appear more than once and that each appearance may be a different atom or molecule found in the definition of that labeled R substitution group. Thus if the labeled $R^6$ substitution group appear four times in a given permutation of Formula (I), then each of those labeled $R^6$ substitution groups may be a different group falling in the definition of $R^6$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed, Mack Publishing Company, Easton, Pa., 1985, p. 1418, the disclosure of which is hereby incorporated by reference.

Since prodrugs are known to enhance numerous desirable qualities of pharmaceuticals (e.g, solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e, =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention or an amount of the combination of compounds claimed effective to inhibit factor Xa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Preparation of the compounds of this invention wherein ring G is a six-membered lactam can be accomplished as illustrated in Scheme 1 by the treatment of the appropriately substituted amine $NH_2$-A-B (for prep. see WO97/23212, WO97/30971, WO97/23212, WO97/38984, WO98/01428, WO98/06694, WO98/28269, WO98/28282, WO98/57934, WO98/57937 and WO98/57951) with 5-bromovaleryl chloride (BVC) to afford 1. Bromination of 1 can be achieved by treatment with $CuBr_2$ in a suitable solvent such as benzene according to the procedure by Fort et. al. (*J. Org. Chem.* 1962, 2937) or by deprotonation with a strong base such as s-BuLi followed by treatment of the resulting enolate with bromine at low temperature as described by Micouin et al. (*Tetrahedron*, 1996, 52 7719) to afford 2. Alternately, compounds of formula 2 can be prepared via the corresponding hydroxylactams by treatment with either carbon tetrabromide in the presence of triphenylphosphine or with phosphorus tribromide to give the bromides. Displacement of the resulting bromide by an SN2 type of reaction in a solvent like tetrahydrofuran, acetonitrile, benzene, or methylene chloride in a presence of a suitable base affords compounds of type 3–6. In some cases, further elaboration of functional groups and/or introduction of additional substituents using methods known to one skilled in the art of organic synthesis may be necessary to provide the various compounds described above in the scope of the invention. Details of the synthesis of illustrative examples of this invention may be found in the Examples section below.

Scheme 1

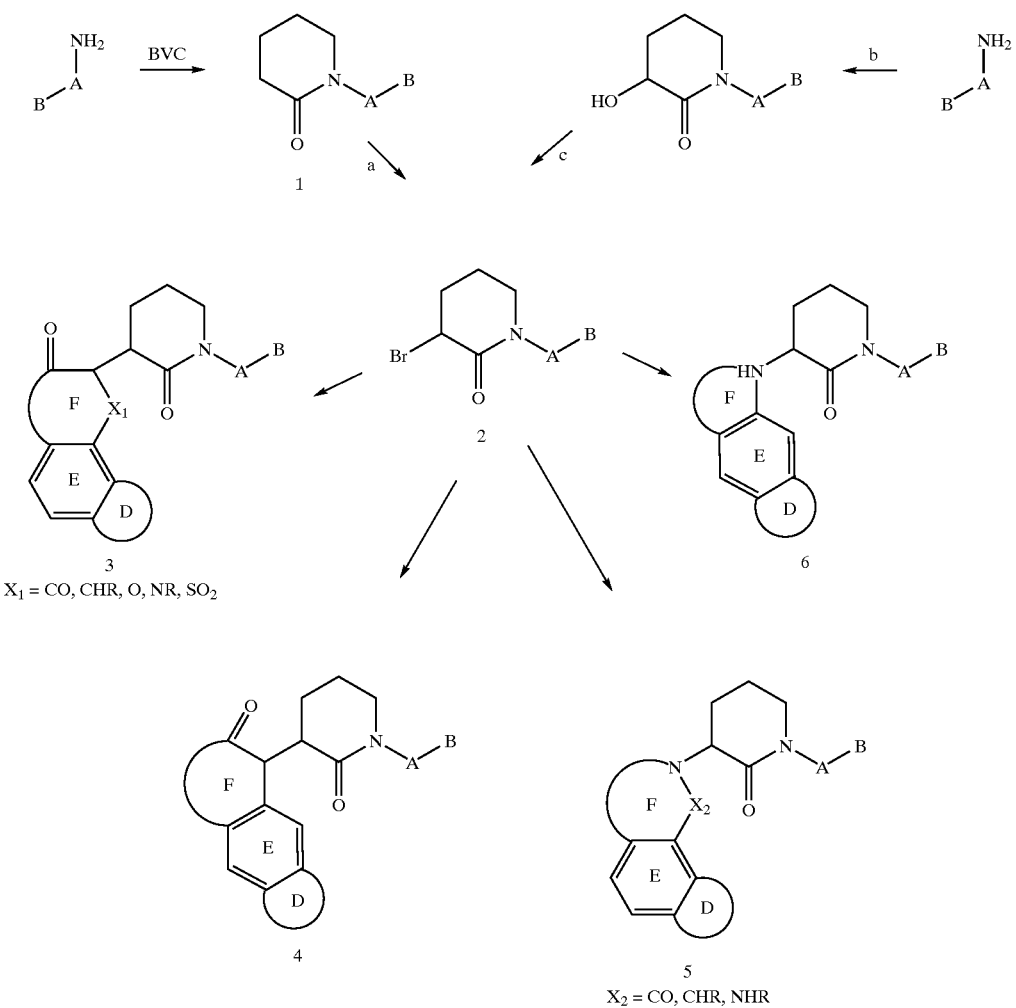

3
$X_1$ = CO, CHR, O, NR, $SO_2$

5
$X_2$ = CO, CHR, NHR a. $CuBr_2$ or sec-BuLi/$Br_2$, -78° C.
b. 1) tetrahydrofuroyl chloride, $CH_2Cl_2$, DMAP;
  2) $BBr_3$, $CH_2Cl_2$;
  3) $Ac_2O$, heptane, reflux;
  4) diisopropyl amine, DMA, reflux
  5) $K_2CO_3$, MeOH
c. $CBr_4$/$Ph_3P$ or $PBr_3$/$CH_2Cl_2$ Other heterocycles and carbocycles useful for the synthesis of compounds of this invention where Ring G is other than the six-membered ring lactam shown in Scheme 1 can be prepared as described in U.S. patent application Ser. No. 10/0003125 filed Oct. 29, 2001, which is incorporated herein by reference.

Various five and six-membered heterocyclic aromatic compounds useful in the synthesis of compounds of this invention are either commercially available or can be prepared according to the methods described by J. A. Joule, *Heterocyclic Chemistry*, 1995. For example, when rings D-E-F are comprised of a substituted indole, indoline, indazole, triazole or benzimidazole, or other nitrogen linked heterocyclic systems, treatment of such a nitrogen heterocycle with a suitable base such as sodium hydride or potassium carbonate in an appropriate solvent, such as THF or DMF, followed by addition of 2 leads to the compounds of this invention of formula 7.

Scheme 2

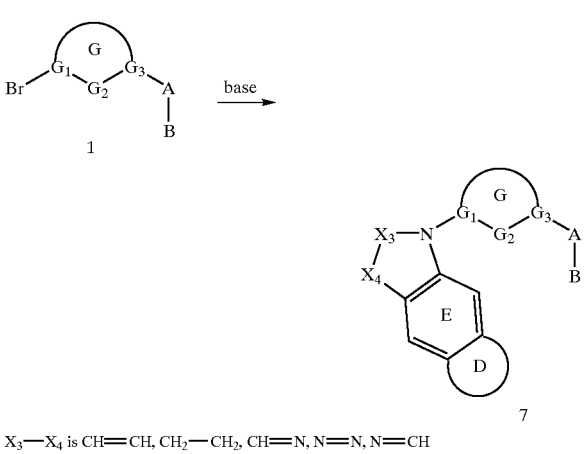

$X_3$—$X_4$ is CH═CH, $CH_2$—$CH_2$, CH═N, N═N, N═CH

Scheme 3 depicts the preparation of starting D-E-F rings such as lactams of formula 8 via Friedel-Crafts type of cyclization (see P. Chovin, *Bull. Soc. Chim. Fr.*, 1945, 12).

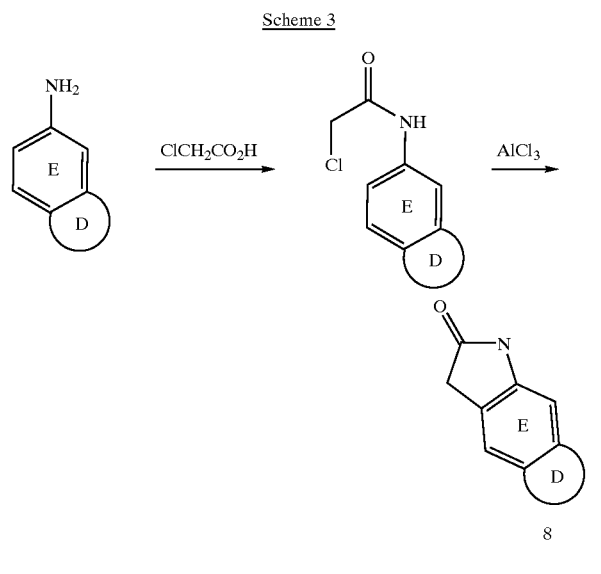

Similarly, synthesis of ureas, carbamates or sultams containing D-E-F rings of formulas 9 and 10 is depicted in Scheme 4. An appropriately substituted aniline can be reacted with the appropriate reagents as outlined in the scheme according to the methods known to those in the art to give the desired products.

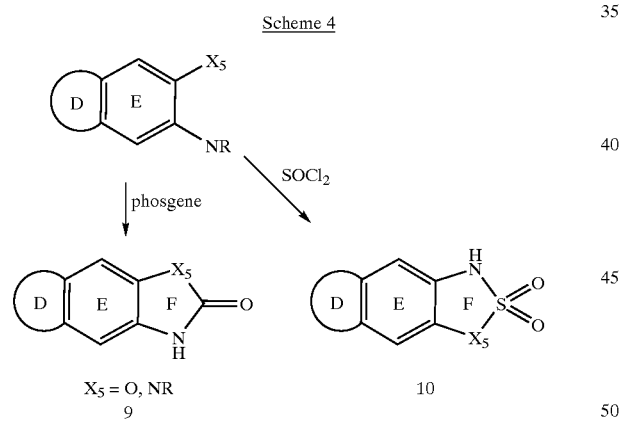

In Scheme 5, an appropriately substituted p-carboethoxy fluorobenzene can react with hydrazine in ethanol to affect cyclization to the give benzazalactam 11 which can be used in Scheme 1 above to prepare additional compounds of the invention.

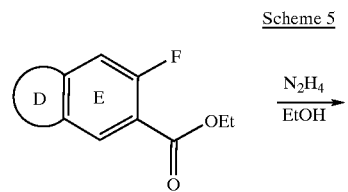

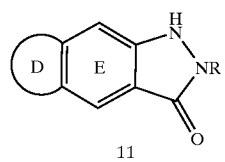

Synthesis of compounds of this invention wherein ring F is connected to Ring G via a carbon atom can be achieved by treatment of an indole compound of formula 12 with a compound of formula 2 (See Scheme 1) in the presence of a suitable Lewis acid in an appropriate solvent such as methylene chloride to leads to the compounds of formula 12 as outlined in Scheme 6 below.

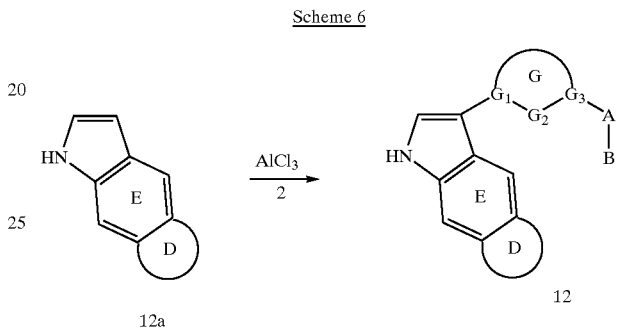

Additional heterocycles useful for incorporation into compounds of this invention as Ring D-E-F groups can be prepared as shown in Schemes 7–24. Treatment of anilines of formula 13a with acrylic acid in a presence of HF and BF3 under pressure leads to compounds of formula 14, that upon reduction with LAH in methylene chloride affords 15 as illustrated in Scheme 7.

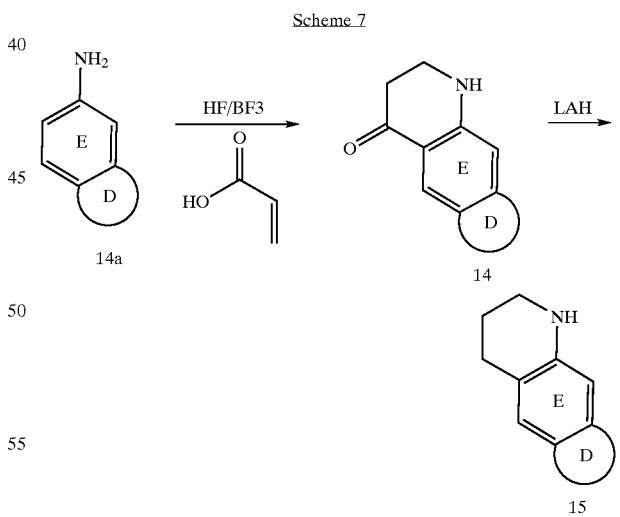

Scheme 8 outlines the preparation of compounds of formula 16 via treatment of an appropriately substituted aniline with chloroacetyl chloride in a presence of the mild base in chloroform (as described by X. Huang et. al. *Synthesis*, 1984, 851). The regioselectivity of the addition is dependent upon the choice of the protecting groups. Reduction with LAH of either regioisomer produces the desired final compounds.

Scheme 8

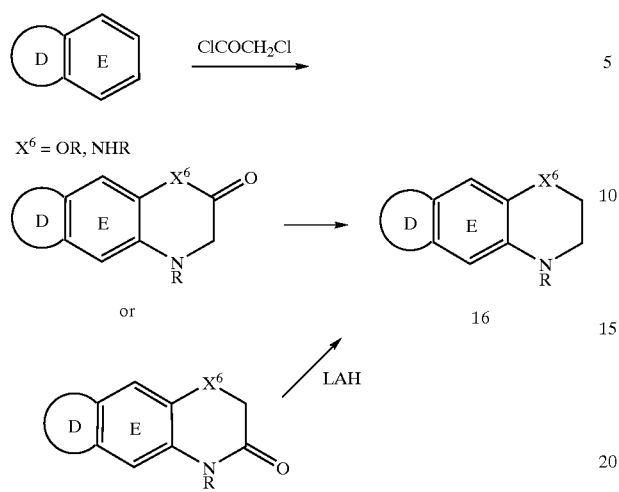

Scheme 11

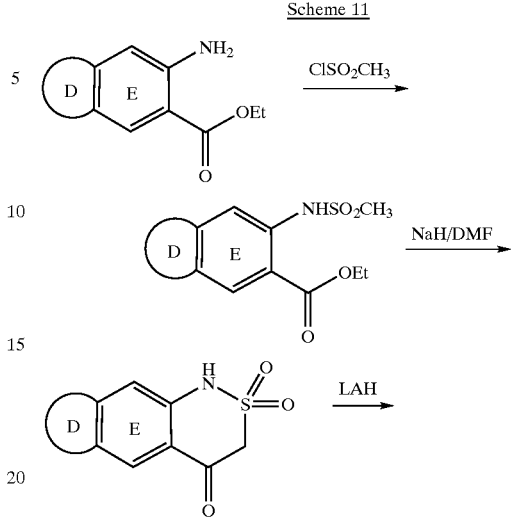

Various 6-membered ring fused heterocycles such as 17–21 shown in Schemes 9 and 10 can be prepared using methods known to those skilled in the art of organic synthesis.

Scheme 9

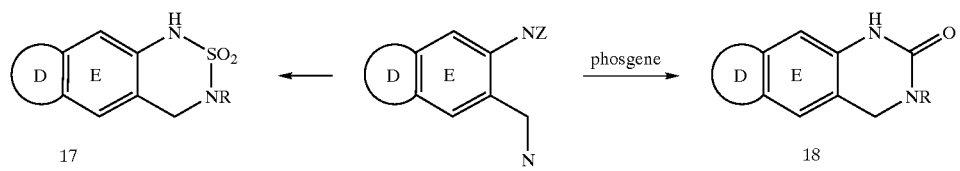

Scheme 10

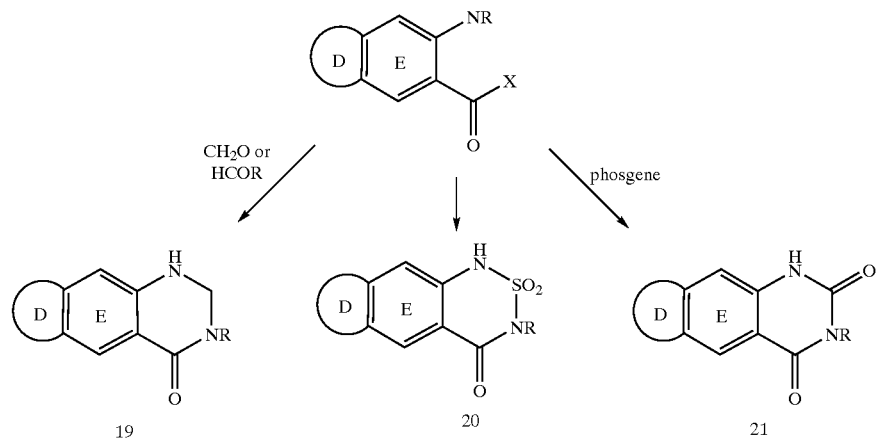

The compounds in scheme 11 can be obtained following the protocol described by Lombardino et al. (*J. Heterocycl. Chem.*, 1979, 9). Treatment of an intermediate sulfonamide, obtained by the conventional methods, with sodium hydride in DMF affects the ring closure. Subsequent reduction with LAH produces the compounds of formula 22.

-continued

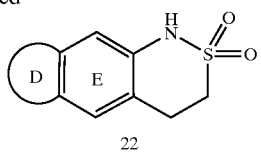

The compounds in scheme 12 can be obtained by the methodology of M. Rai et.al. (*Chem Ind.*, London, 1979, 26) by the treatment of an intermediate substituted imine, obtained by methods known in the art, with methylsulfonyl chloride in THF to afford the compounds of formula 23.

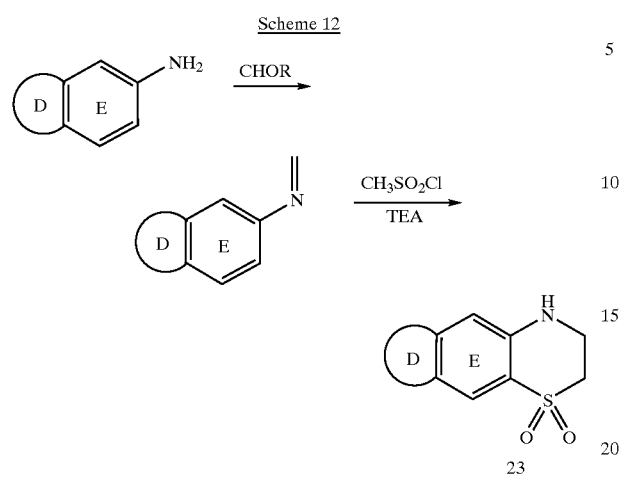

The compounds in Scheme 13 can be prepared by Schmidt rearrangement of 6-hydroxy-tetralone. Treatment of 6-hydroxy-tetralone with sodium azide-trichloroacetic acid affords hydroxybenzazepine 24, which can be reduced by LiAlH4 to benzazepine 25 (Valderrama et al., *Syn. Comm.* 1992, 22(4), 629–639.)

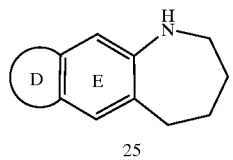

Compounds of formula 26 can be prepared as shown in Scheme 14 from 2-amino-phenols, which can be prepared from the methods either by Makosza et al., *J. Org. Chem.*, 1998, 63(13), 4199–4208, or by Hanzlik et al., *J. Org. Chem.*, 1990, 55(9), 2763–2742.

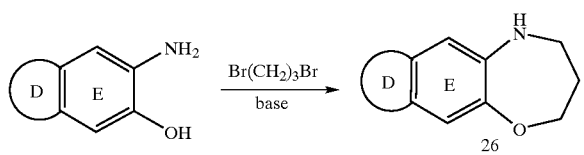

The compounds of formula 27 and 28 can be prepared from 2-amino-benzoic acids as shown in Scheme 15.

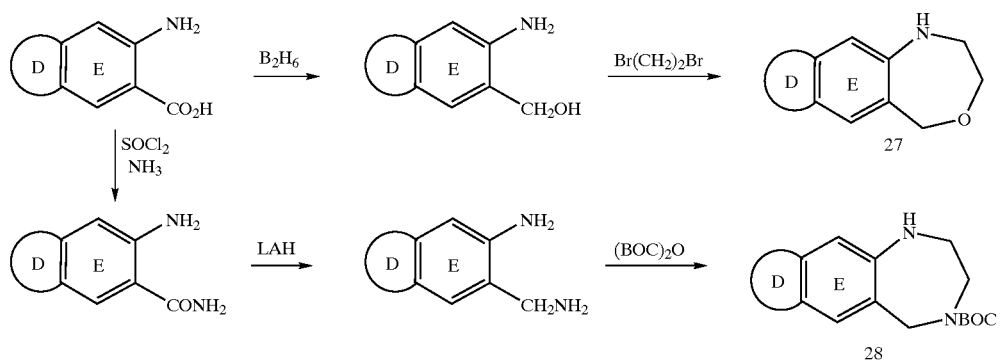

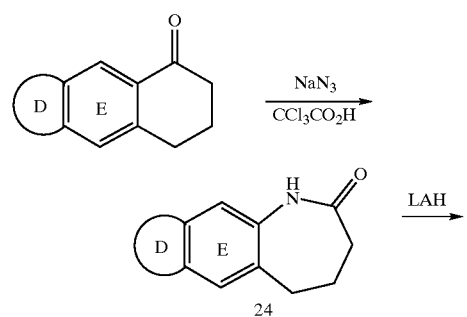

The compounds of formula 29 can be prepared from anilines as shown in Scheme 16 by the methods known to those in the art.

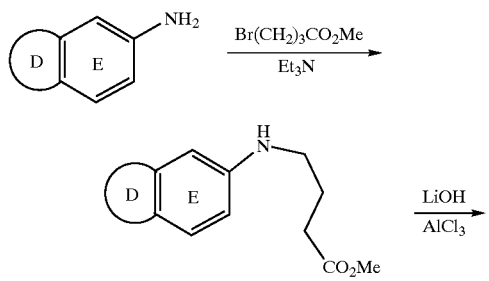

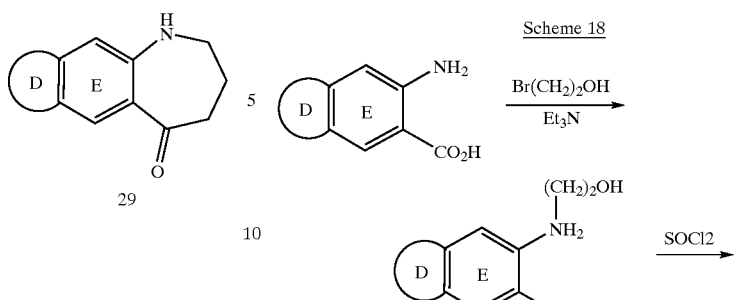
The compounds of formula 30 can be prepared from hydroxyanilines as shown in Scheme 17.
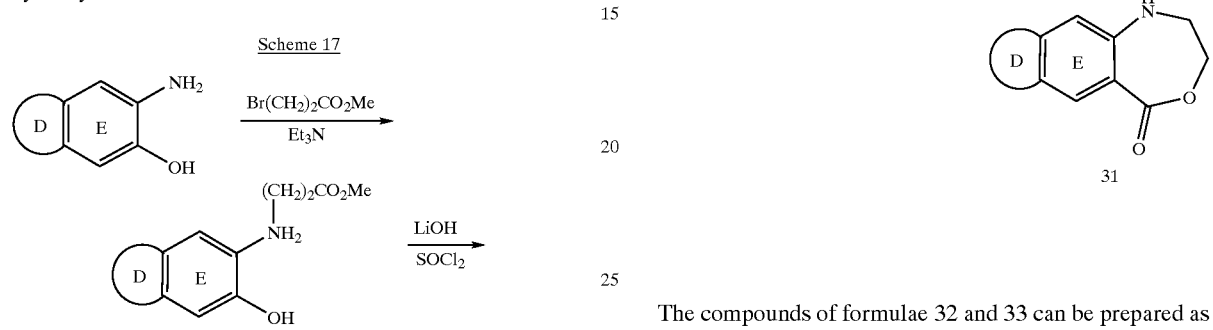
The compounds of formula 31 can be prepared from 2-amino-benzoic acids as shown in Scheme 18.
The compounds of formulae 32 and 33 can be prepared as shown in Scheme 19.
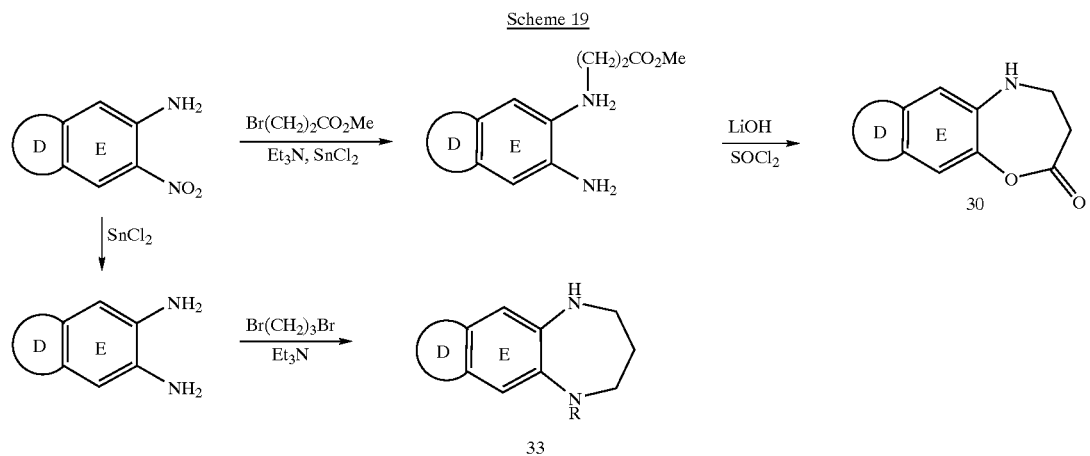
The compounds of formula 34 can be prepared as shown in Scheme 20.
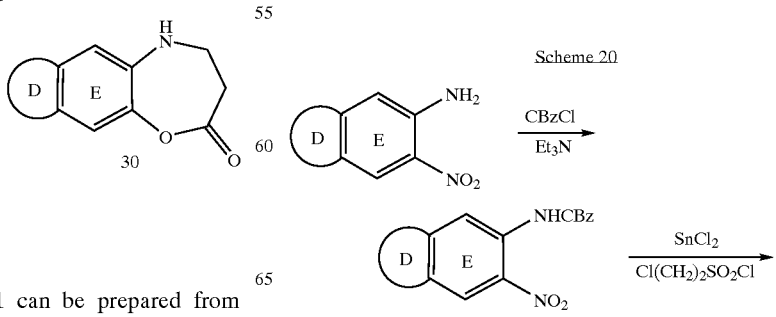

-continued

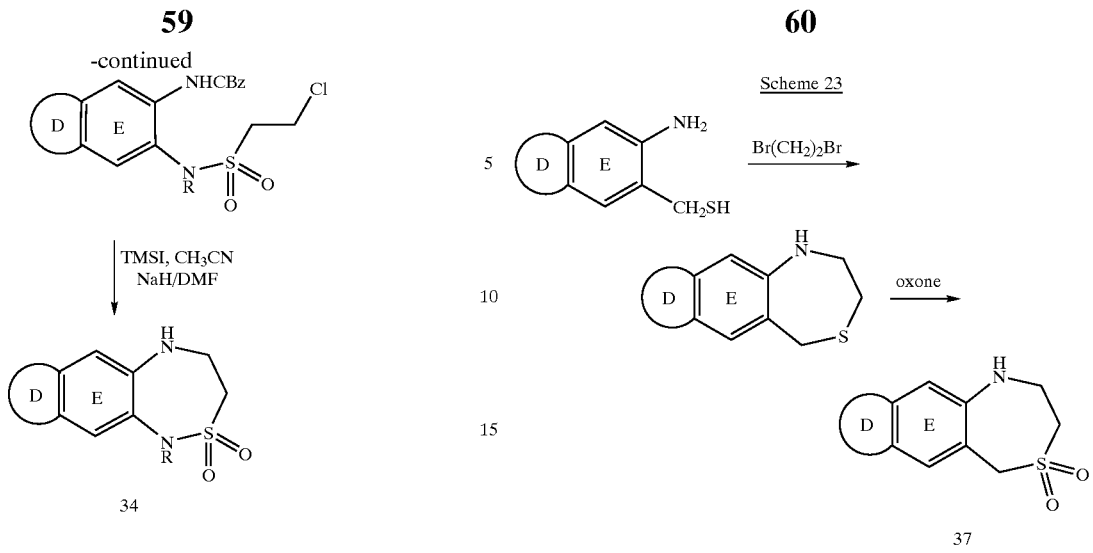

The compounds of formula 35 can be prepared as shown in Scheme 21.

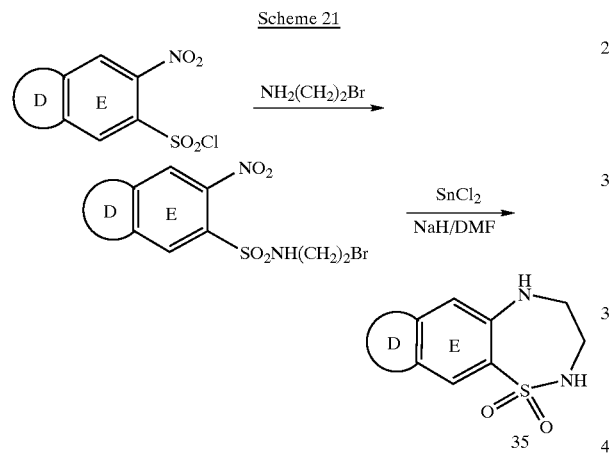

The compounds of formula 36 can be prepared as shown in Scheme 22.

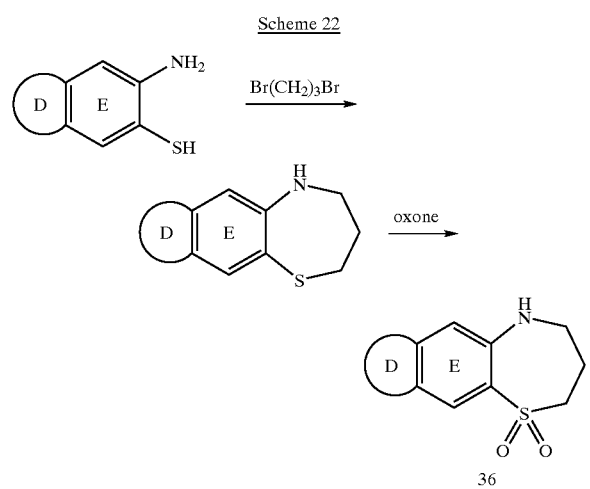

The compounds of formula 37 can be prepared as shown in Scheme 23.

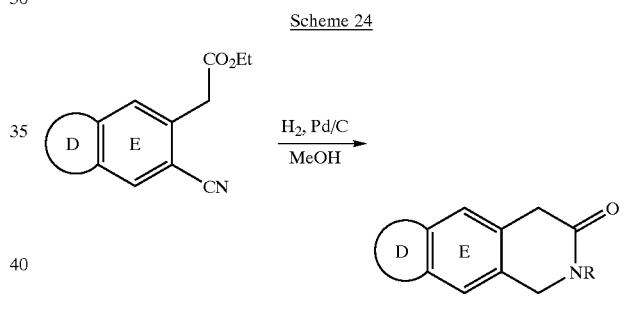

The compounds described in Scheme 24 can be easily prepared by the reduction and subsequent cyclization of an appropriately substituted benzonitrile, followed by the treatment with ethyl chloroformate in a presence of a strong base such as LDA. The intermediate ester can be hydrolyzed to the acid with NaOH in THF and water and converted to the acid chloride upon refluxing with thionyl chloride in a solvent such as methylene chloride or tetrahydrofuran.

UTILITY

The compounds of this invention are useful as anticoagulants for the treatment or prevention of thromboembolic disorders in mammals. In general, a thromboembolic disorder is a circulatory disease caused by blood clots (i.e., diseases involving platelet activation and/or platelet aggregation). The term "thromboembolic disorders" as used herein includes arterial cardiovascular thromboembolic disorders, venous cardiovascular thromboembolic disorders, arterial cerebrovascular thromboembolic disorders, and venous cerebrovascular thromboembolic disorders. The term "thromboembolic disorders" as used herein includes specific disorders selected from, but not limited to, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous translumianl coronary angioplasty). The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of $\leq 10\ \mu M$. Preferred compounds of the present invention have $K_i$'s of $\leq 1\ \mu M$. More preferred compounds of the present invention have $K_i$'s of $\leq 0.1\ \mu M$. Even more preferred compounds of the present invention have $K_i$'s of $\leq 0.01\ \mu M$. Still more preferred compounds of the present invention have $K_i$'s of $\leq 0.001\ \mu M$. Using the methodology described above, a number of compounds of the present invention were found to exhibit a Ki of $\leq 10\ \mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of the present invention may also be useful as inhibitors of serine proteases, notably human thrombin, Factor VIIa, Factor IXa, plasma kallikrein and plasmin Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 1990, 265, 18289–18297, herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than $10\ \mu m$, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine and clopidogrel, including pharmaceutically acceptable salts or prodrugs thereof. Ticlopidine and clopidogrel are also preferred compounds since they are known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, heparins, hirudin and argatroban, including pharmaceutically acceptable salts and prodrugs thereof. The term hirudin, as used herein, includes suitable derivatives or analogs of hirudin, referred to herein as hirulogs, such as disulfatohirudin.

The term thrombolytics (or fibrinolytic) agents (or thrombolytics or fibrinolytics), as used herein, denotes agents that lyse blood clots (thrombi). Such agents include tissue plasminogen activator and modified forms thereof, anistreplase, urokinase or streptokinase, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or in separate forms but at the same time by the same manner, will be readily apparent to those skilled in the art, once armed with the present disclosure.

Other features of the invention will become apparent in the course of the following descriptions of exemplary embodiments that are given for illustration of the invention and are not intended to be limiting thereof.

EXAMPLES

Example 1

1-{1-[3-Fluoro-2'-(methylsulfonyl)[1,1'-biphenyl]-4-yl]-2-oxo-3-piperidinyl}-1H-indole-6-carboximidamide Part A. 3-bromo-1-(4-bromo-2-fluorophenyl)-2-piperidinone:

A solution of 1-(4-bromo-2-fluorophenyl)-3-hydroxy-2-piperidinone (1 g, 3.5 mmol) in acetonitrile (20 ml) was treated with carbon tetrabromide (2.3 g, 7 mmol) and triphenylphosphine (1.8 g, 7 mmol. The reaction was stirred at ambient temperature over a period of 3 h, taken up in water and extracted with ethyl acetate (3×). Ethyl acetate extracts were dried over sodium sulfate and concentrated. The crude residue was purified by flash chromatography (hexane/ethyl acetate, 1:3) to afford the bromo compound (0.8 g, 67%). LRMS (ES+): 352.1 (M+H)$^+$.

Part B. 1-[1(4-bromo-2-fluorophenyl)-2-oxo-3-piperidinyl]-1H-indole-6-carbonitrile:

A solution of 6-cyanoindole (0.32 g, 2.3 mmol) in tetrahydrofuran (15 ml) was cooled down and treated with sodium hydride (0.18 g, 4.5 mmol) and the compound of Ex. 1, Part A (0.79 g, 2.3 mmol). The reaction was stirred at ambient temperature over a period of 4 h, taken up in water and extracted with ethyl acetate (3×). Ethyl acetate extracts were dried over sodium sulfate and concentrated. The crude residue was purified by flash chromatography (hexane/ethyl acetate, 1:3) to afford the product (0.7 g, 75%). LRMS (ES+): 413.1 (M+H)$^+$.

Part C. 1-{1-[3-fluoro-2'-(methylsulfonyl)[1,1'-biphenyl]-4-yl]-2-oxo-3-piperidinyl}-1H-indole-6-carbonitrile:

A solution of the compound of Ex. 1, Part B (0.2 g, 0.5 mmol) and 2-methylthiophenylboronic acid (82 mg, 0.5 mmol) in a mixture of tetrahydrofuran (10 ml) and aqueous sodium carbonate (5 ml) was deoxygenated by a rapid stream of nitrogen applied to the system over a period of 20 min, then treated with Pd(0). The reaction was refluxed over a period of 18 h., cooled down, filtered through Celite and washed with THF (20 ml). The filtrate evaporated to dryness, taken up in water and extracted with ethyl acetate (3×). Ethyl acetate extracts were dried over sodium sulfate and concentrated. The crude residue was purified by flash chromatography (hexane/ethyl acetate, 1:3) to afford the coupled product(0.2 g, 90%). This product was dissolved in methylene chloride and treated with MCPBA (0.2 g, 1 mmol). The reaction mixture was stirred for 18 h, concentrated and purified through a plug of silica gel(hexane/ethyl acetate, 1:1) to afford the desired compound (0.2 g, 93%). LRMS (ES+): 488.5 (M+H)$^+$.

Part D. 1-{1-[3-fluoro-2'-(methylsulfonyl)[1,1'-biphenyl]-4-yl]-2-oxo-3-piperidinyl}-1H-indole-6-carboximidamide:

A solution of the compound of Ex. 1, Part C (0.1 g, 0.2 mmol) in anhydrous EtOH (20 mL) was bubbled with HCl gas at 0° C. for 15 min The resulting solution was stirred overnight at room temperature and concentrated in vacuo. The solid was redissolved in anhydrous EtOH (20 mL) and ammonium carbonate (2 g, 2.5 mmol) was added followed by 1 mL pyridine. The resulting solution was stirred overnight at room temperature. The volatiles were removed in vacuo, and the residue purified by HPLC to give the title compound. LRMS (ES+): 505.3 (M+H)$^+$.

Example 2

1-(1-{2'-[(Dimethylamino)methyl]-3-fluoro[1,1'-biphenyl]-4-yl}-2-oxo-3-piperidinyl)-6-indoline carboximidamide Part A. 1-(1-{2'-[(dimethylamino)methyl]-3-fluoro[1,1'-biphenyl]-4-yl}-2-oxo-3-piperidinyl)-6-indoline carbonitrile:

A mixture of the compound of Ex. 1, Part B (0.5 g, 1.3 mmol) and 2-formylbenzene boronic acid (0.2 g, 1.3 mmol) was diluted with THF (20 ml) and 2M sodium carbonate (10 ml), then deoxygenated by a rapid stream of nitrogen applied to the system over a period of 20 min, followed by treatment with Pd(0). The reaction was refluxed over a period of 18 h., cooled down, filtered through Celite and washed with THF (20 ml). The filtrate evaporated to dryness, taken up in water and extracted with ethyl acetate (3×). Ethyl acetate extracts were dried over sodium sulfate and concentrated. The crude residue (0.6 g) was treated with sodium borohydride (0.6 g, 2.8 mmol) and dimethyl amine (1.5 ml, 2M solution in THF). The reaction mixture was stirred for 18 h., diluted with ice water and extracted with ethyl acetate. Ethyl acetate extracts were dried over sodium sulfate and concentrated. The crude residue was purified by flash chromatography (hexane/ethyl acetate, 1:3) to afford the desired product (0.6 g, 75% over last 2 steps). LRMS (ES+): 469.2 (M+H)$^+$.
Part B. 1-(1-{2'-[(dimethylamino)methyl]-3-fluoro[1,1'-biphenyl]-4-yl}-2-oxo-3-piperidinyl)-6-indoline carboximidamide:

The compound of Ex. 2, Part A was converted to the corresponding amidine according to the procedure described in Ex. 1, Part D. LRMS (ES+): 484.2 (M+H)$^+$.

Example 3

Ethyl-1-{1-[3-fluoro-2'-(methylsulfonyl)[1,1'-biphenyl]-4-yl]-2-oxo-3-piperidinyl}-5-methoxy-1H-indole-2-carboxylate Part A. 1-[3-fluoro-2'-(methylsulfanyl)[1,1'-biphenyl]-4-yl]-3-hydroxy-2-piperidinone:

A solution of 1-(4-bromo-2-fluorophenyl)-3-hydroxy-2-piperidinone (5.0 g, 16.3 mmol) and 2-methylthiophenylboronic acid (2.7 g, 16.3 mmol) in a mixture of tetrahydrofuran (50 ml) and aqueous sodium carbonate (15 ml) was deoxygenated by a rapid stream of nitrogen applied to the system over a period of 20 min, then treated with Pd(0) at once. The reaction was refluxed over a period of 18 h, cooled down, filtered through Celite and washed with THF (20 ml). The filtrate evaporated to dryness, taken up in water and extracted with ethyl acetate (3×). Ethyl acetate extracts were dried over sodium sulfate and concentrated. The crude residue was purified by flash chromatography (hexane/ethyl acetate, 1:3) to afford the desired product (5 g, 88%). LRMS (ES+): 350.5 (M+H)$^+$.
Part B. 3-bromo-1[3-fluoro-2'-(methylsulfonyl)[1,1'-biphenyl]-4-yl]-2-piperidinone:

A solution of the compound of Ex. 3, Part A (1 g, 3.5 mmol) in methylene chloride (20 ml), was treated with PBr$_3$ (0.8 g, 3.5 mmol). The reaction was stirred at ambient temperature over a period of 3 h, taken up in water and extracted with ethyl acetate (3×). Ethyl acetate extracts were dried over sodium sulfate and concentrated. The crude residue was purified by flash chromatography (hexane/ethyl acetate, 1:3) to afford 3-bromo-1-[3-fluoro-2'-(methylsulfanyl)[1,1'-biphenyl]-4-yl]-2-piperidinone (1 g, 50%). LRMS (ES+): 414.1 (M+H)$^+$. This product was dissolved in methylene chloride and treated with MCPBA (1.3 g, 10.5 mmol). The reaction mixture was stirred for 18 h, concentrated and purified through a plug of silica gel (hexane/ethyl acetate, 1:1) to afford the sulfone (1 g, 93%). LRMS (ES+): 445.5 (M+H)$^+$.
Part C. ethyl-1-{1-[3-fluoro-2'-(methylsulfonyl)[1,1'-biphenyl]-4-yl]-2-oxo-3-piperidinyl}-5-methoxy-1H-indole-2-carboxylate:

A solution of 2-ethylcarboxylate-5-methoxy-indole (50 mg, 0.23 mmol) in THF (3 ml), was treated with sodium hydride (10 mg, 60% in oil). The reaction was stirred at ambient temperature over a period of 10 min and then treated with the compound of Ex. 3, Part B (0.1 g, 0.23 mmol). The reaction mixture was stirred for 1 hr, taken up in water and extracted with ethyl acetate (3×). Ethyl acetate extracts were dried over sodium sulfate and concentrated. The crude residue was purified by flash chromatography (hexane/ethyl acetate, 1:3) to give the title compound (65 mg, 50%). LRMS (ES+): 565.5 (M+H)$^+$.

Example 4

1-[3-Fluoro-2'-(methylsulfonyl)[1,1'-biphenyl]-4-yl]-3-(5-methoxy-1H-indol-1-yl)-2-piperidinone This compound was prepared from the compound of Ex. 3, Part B and 5-methoxyindole according to the procedure described in Ex. 3, Part C. LRMS (ES+): 494.2 (M+H)$^+$.

Example 5

3-{1-[3-Fluoro-2'-(methanesulfonyl)-[1,1'-biphenyl]-4-yl]-2-oxo-piperidin-3-yl}-6-methoxy-3H-benzoxazol-2-one This compound was prepared from the compound of Ex. 3, Part B and 6-methoxy-3H-benzoxazol-2-one according to the procedure described in Ex. 3, Part C. LRMS (ES+): 511.54 (M+H)$^+$.

Example 6

1-{1-[3-Fluoro-2'-(methylsulfonyl)[1,1'-biphenyl]-4-yl]-2-oxo-3-piperidinyl}-1H-indazole-6-carboximidamide Part A. 1-[1-(3-fluoro-2'-methylsulfanyl)[1,1'-biphenyl]-4-yl)-2-oxopiperidin-3-yl]-1H-indazole-6-carbonitrile:

A stirred solution of 3-bromo-1-(3-fluoro-2'-methylsulfanylbiphenyl-4-yl)-piperidin-2-one, prepared as described in Ex. 3, Part B above, (1.2 g, 3 mmol) and 1H-indazole-6-carbonitrile (9, 230 mg, 1.5 mmol) in DMF (0.5 mL) was treated with anhydrous K$_2$CO$_3$ (828 mg, 6 mmol) and stirred at room temperature for 12 h. The reaction mixture was diluted with EtOAc (100 mL) and washed with NH$_4$Cl, NaHCO$_3$, and brine. The organic phase was dried over Na$_2$SO$_4$, filtered, and concentrated. The residue was purified by column chromatography to provide the desired product (293 mg, 42%): $^1$H NMR (300 MHz, CDCl$_3$) δ 8.15 (s, 11H), 7.9 (s, 1H), 7.8 (d, 1H, J=8.5 Hz), 7.4–7.1 (m, 8H), 5.4 (dd, 1H, J=9, 11 Hz), 4.0 (m, 1H), 3.8 (m, 1H), 2.9 (m, 1H), 2.6 (m, 1H), 2.5–2.2 (m, 4H); ESI MS m/z 457 (M+H)$^+$.
Part B. 1-[1-(3-fluoro-2'-methanesulfonyl)[1,1'-biphenyl]-4-yl)-2-oxopiperidin-3-yl]-1H-indazole-6-carbonitrile:

A stirred solution of the compound of Ex. 6, Part A (293 mg, 0.64 mmol) in CH$_2$Cl$_2$ (50 mL) was treated with anhydrous K$_2$CO$_3$ (180 mg, 1.3 mmol) and cooled to 0° C. The reaction was treated with m-CPBA (50%, 224 mg, 1.3 mmol), warmed to RT, and stirred overnight. The reaction was diluted with CH$_2$CO$_2$ (200 mL) and washed with Na$_2$S$_2$O$_3$ (100 mL), NaHCO$_3$ (100 mL), and brine. The organic phase was dried over Na$_2$SO$_4$, filtered, and concentrated. The residue was purified by column chromatography to provide the corresponding sulfone (260 mg, 83%): $^1$H NMR (300 MHz, CDCl$_3$) δ 8.2 (m, 1H), 8.15 (s, 1H), 7.9 (s, 1H), 7.8 (d, 1H, J=9 Hz), 7.7–7.5 (m, 2H), 7.3 (m, 8H), 5.4 (dd, 1H, J=9, 11 Hz), 4.0 (m, 1H), 3.8 (m, 1H), 2.9 (m, 1H), 2.7 (s, 3H), 2.6 (m, 1H), 2.5–2.2 (m, 2H); ESI MS m/z 489 (M+H)$^+$.
Part C. 1-{1-[3-fluoro-2'-(methylsulfonyl)[1,1'-biphenyl]-4-yl]-2-oxo-3-piperidinyl}-1H-indazole-6-carboximidamide:

A stirred solution of the compound of Ex. 6, Part B (250 mg, 0.51 mmol) in anhydrous ethanol was cooled to 0° C. and treated with HCl gas until saturated. The reaction vessel was sealed and maintained at −20° C. for 24 h. The reaction was monitored by HPLC analysis until the starting material was consumed then the reaction mixture was concentrated. The residue was dissolved in anhydrous ethanol and treated with an excess of (NH$_4$)$_2$CO$_3$ (~1 g). The reaction vessel was sealed, stirred at room temperature for 12 h, and concentrated. The reaction was dissolved in CH$_2$Cl$_2$ (10 mL), cooled to 0° C., treated with TFA (0.2 mL), and concentrated. The residue was purified by preparative HPLC to provide the title compound as a white solid. $^1$H NMR (300 MHz, DMSO-d$_6$) δ 9.4 (s, 2H), 9.0 (s, 2H), 8.3 (d, 2H J=9 Hz), 8.1 (d, 1H, J=9 Hz), 8.0 (d, 1H, J=9 Hz), 7.8–7.1 (m, 2H), 7.6–7.3 (m, 5H), 5.8 (dd, 1H, J=11, 9 Hz), 4.0 (m, 1H), 3.8 (m, 1H), 2.9 (s, 3H), 2.8 (m, 1H), 2.5 (m, 1H), 2.3 (m, 2H); APCI MS m/z 506 (M+H)$^+$.

Example 7

1-{1-[3-Fluoro-2'-(methylsulfonyl)[1,1'-biphenyl]-4-yl]-2-oxo-3-piperidinyl}-3H-benzimidazole-5-carboximidamide Part A. 3-[1-(3-fluoro-2'-methylsulfanyl)[1,1'-biphenyl]-4-yl]-2-oxopiperidin-3-yl]-3H-benzimidazole-5-carbonitrile (3) and 1-[1-(3-fluoro-2'-methylsulfanyl)-[1,1'-biphenyl]-4-yl]-2-oxo-piperidin-3-yl]-1H-benzimidazole-5-carbonitrile:

A stirred solution of 3-bromo-1-(3-fluoro-2'-(methylsulfanyl)[1,1'-biphenyl]-4-yl)-piperidin-2-one, prepared as described in Ex. 3, Part B above, (310 mg, 0.79 mmol) and 3H-benzimidazole-5-carbonitrile (225 mg, 1.57 mmol, U.S. Pat. No. 5,886,191) in DMF (0.5 mL) was treated with anhydrous K$_2$CO$_3$ (414 mg, 2.9 mmol) and stirred at room temperature for 12 h. The reaction mixture was diluted with EtOAc (100 mL) and washed with NH$_4$Cl, NaHCO$_3$, and brine. The organic phase was dried over Na$_2$SO$_4$, filtered, and concentrated. The residue was purified by column chromatography to provide the product as a mixture of regioisomers (340 mg, 95%, mixture of two isomers). The regioisomers were separated by preparative HPLC and characterized by NOE difference spectroscopy. Isomer A: 3-[1-(3-fluoro-2'-methylsulfanylbiphenyl-4-yl)-2-oxopiperidin-3-yl]-3H-benzimidazole-5-carbonitrile: $^1$H NMR (300 MHz, CDCl$_3$) δ 8.2 (s, 1H), 7.85 (d, 1H, J=9 Hz) 7.75 (s, 1H), 7.55 (d, 1H, J=9 Hz), 7.4–7.1 (m, 10H), 5.2 (t, 1H, J=9 Hz), 4.1–3.7 (m, 2H), 2.6 (m, 2H), 2.4 (s, 3H), 2.35 (m, 2H); ESI MS m/z 457 (M+H)$^+$.
Isomer B: 1-[1-(3-fluoro-2'-methylsulfanylbiphenyl-4-yl)-2-oxo-piperidin-3-yl]-1H-benzimidazole-5-carbonitrile: $^1$H NMR (300 MHz, CDCl$_3$) δ 8.15 (d, 1H, J=9 Hz), 7.6 (d, 1H, J=9 Hz), 7.5 (d, 1H, J=9 Hz), 7.3–7.1 (m, 11H), 5.2 (t, 1H, J=9 Hz), 4.1–3.7 (m, 2H), 2.6 (m, 2H), 2.4 (s, 3H), 2.35 (m, 2H); ESI MS m/z 457 (M+H)$^+$.

Part B. 3-[1-(3-fluoro-2'-methylsulfonyl)[1,1'-biphenyl]-4-yl]-2-oxopiperidin-3-yl]-3H-benzimidazole-5-carbonitrile:

A stirred solution of the compound of Ex. 7, Part A, isomer A (310 mg, 0.68 mmol) in CH$_2$Cl$_2$ (50 mL) was treated with anhydrous K$_2$CO$_3$ (373 mg, 2.7 mmol) and cooled to 0° C. The reaction was treated with m-CPBA (50%, 467 mg, 1.36 mmol), warmed to RT, and stirred overnight. The reaction was diluted with CH$_2$Cl$_2$ (200 mL) and washed with 15% aqueous Na$_2$S$_2$O$_3$ (100 mL), NaHCO$_3$ (100 mL), and brine. The organic phase was dried over Na$_2$SO$_4$, filtered, and concentrated. The residue was purified by column chromatography to provide the desired product (303 mg, 91%): $^1$H NMR (300 MHz, CD$_3$OD) δ 8.5 (s, 1H), 8.2 (d, 1H, J=9 Hz), 8.1 (s, 1H), 7.8 (d, 1H, J=9 Hz), 7.8–7.4 (m, 5H), 7.4–7.2 (m, 3H), 5.7 (dd, 1H, J=12, 9 Hz), 4.1 (m, 1H), 3.9 (m, 1H), 2.8 (s, 3H), 2.7 (m, 1H), 2.6 (m, 1H), 2.3 (m, 1H); ESI MS m/z 489 (M+H)$^+$.

Part C. 1-{1-[3-fluoro-2'-methylsulfonyl)[1,1'-biphenyl]-4-yl]-2-oxo-3-piperidinyl}-3H-benzimidazole-5-carboximidamide:

The compound of Ex. 7, Part B (5, 250 mg, 0.51 mmol) was converted to the corresponding amidine using the procedure described for Ex. 6, Part C to give the title compound as a white solid: $^1$H NMR (300 MHz, DMSO-d$_6$) δ 9.4 (s, 2H), 9.0 (s, 2H), 8.6 (s, 1H), 8.1 (m, 2H), 7.9 (d, 1H J=9 Hz), 7.8–7.3 (m, 9H), 5.7 (dd, 1H, J=12, 9 Hz), 4.0 (m, 1H), 3.8 (m, 1H), 2.9 (s, 3H), 2.7 (m, 2H), 2.4 (m, 1H), 2.25 (m, 2H); APCI MS m/z 506 (M+H)$^+$.

Example 8

1-{1-[(3-Fluoro-2'-methylsulfonyl)[1,1'-biphenyl]-4-yl]-2-oxo-3-piperidinyl}-1H-benzimidazole-5-carboximidamide Part A: 1-{1-[(3-fluoro-2'-methylsulfonyl)[1,1'-biphenyl]-4-yl]-2-oxopiperidin-3-yl]-1H-benzimidazole-5-carbonitrile:

A stirred solution the compound of Ex. 7, Part A, Isomer B (305 mg, 0.68 mmol) in CH$_2$Cl$_2$ (50 mL) was treated with anhydrous K$_2$CO$_3$ (373 mg, 2.7 mmol) and cooled to 0° C. The reaction was treated with m-CPBA (50%, 467 mg, 1.36 mmol), warmed to RT, and stirred overnight. The reaction was diluted with CH$_2$Cl$_2$ (200 mL) and washed with 15% aqueous Na$_2$S$_2$O$_3$ (100 mL), NaHCO$_3$ (100 mL), and brine. The organic phase was dried over Na$_2$SO$_4$, filtered, and concentrated. The residue was purified by column chromatography to provide the desired product (6, 309 mg, 93%): $^1$H NMR (300 MHz, CD$_3$OD) δ 8.5 (s, 1H), 8.2 (d, 1H, J=9 Hz), 8.1 (s, 1H), 7.8 (d, 1H, J=9 Hz), 7.7–7.6 (m, 5H), 7.6 (t, 1H, J=9 Hz), 7.4–7.3 (m, 3H), 5.7 (dd, 1H, J=12, 9 Hz), 4.1 (m, 1H), 3.9 (m, 1H), 2.8 (s, 3H), 2.7 (m, 1H), 2.6 (m, 1H), 2.5–2.3 (m, 1H); ESI MS m/z 489 (M+H)$^+$.

Part B. 1-{1-[(3-fluoro-2'-methylsulfonyl)[1,1'-biphenyl]-4-yl]-2-oxopiperidin-3-yl]-1H-benzimidazole-5-carboximidamide:

The compound of Ex. 8, Part A (250 mg, 0.51 mmol) was converted to the corresponding amidine using the procedure described in Ex. 6, Part C to provide the title compound as a white solid: $^1$H NMR (300 MHz, DMSO-d$_6$) δ 9.25 (s, 2H), 8.9 (s, 2H), 8.6 (s, 1H), 8.25 (s, 1H), 8.1 (d, 1H, J=9 Hz), 7.85 (d, 1H, J=9 Hz), 7.8–7.3 (m, 8H), 5.7 (dd, 1H, J=12, 9 Hz), 4.1 (m, 1H), 3.8 (m, 1H), 2.9 (s, 3H), 2.7 (m, 2H), 2.5 (m, 1H), 2.25 (m, 2H); APCI MS m/z 506 (M+H)$^+$.

Example 9

1-(1-[3-Fluoro-2'-(methylsulfonyl)[1,1'-biphenyl]-4-yl]-2-oxo-piperidin-3-yl]-5-methoxy-1H-indole-2,3-dione A mixture of the compound of Ex. 3, Part B (30 mg, 0.071 mmol), 5-methoxyisatin (19 mg, 0.106 mmol) and cesium carbonate (35 mg. 0.106 mmol) in DMF (2 ml) was stirred at RT overnight. The reaction mixture was diluted with water and extracted 3× with ethyl acetate. The extracts were combined, washed with brine and dried over anhydrous magnesium sulfate, filtered and concentrated in vacuo to give a red residue which was purified by column chromatography on silica gel (50%–75% ethyl acetate in hexane) to provide the title compound as a red film (25 mg, 69%). $^1$H-NMR (CDCl$_3$, 300 MHz) δ 8.23 (d, J=7.6 Hz, 1H), 7.63 (m, 2H), 7.30 (m, 4H), 7.20 (m, 1H), 6.80 (d, J=8.1 Hz, 1H), 5.10 (m, 1H), 3.96 (m, 1H), 3.80 (s, 3H), 3.76 (m, 1H), 2.72 (s, 3H), 2.50 (m, 1H), 2.30 (m, 3H); mass spectrum, ESI (M+H)+523.4, (M+Na)$^+$ 545.4.

Example 10

1-[(3-Fluoro-2'-methylsulfanyl)[1,1'-biphenyl]-4-yl]-3-(6-methoxy-3,4-dihydro-2H-quinolin-1-yl)piperidin-2-one A stirred solution of 6-methoxy-1,2,3,4-tetrahydroquinoline (193 mg, 0.49 mmol) and anhydrous K$_2$CO$_3$ (165 mg, 1.2 mmol) in DMF (1.5 mL) was cooled to 0° C. and treated with 3-bromo-1-(3-fluoro-2'-methylsulfanylbiphenyl-4-yl)piperidin-2-one, prepared as in Ex. 3, Part B above, (160 mg, 0.98 mmol). The solution was warmed to room temperature and stirred for 36 h. The reaction mixture was diluted with EtOAc (100 mL) and washed with NH$_4$Cl, NaHCO$_3$, and brine. The organic phase was dried over Na$_2$SO$_4$, filtered, and concentrated. The residue was purified by column chromatography to provide the desired product (105 mg, 45%): $^1$H NMR (300 MHz, CDCl$_3$) δ 7.5–7.1 (m, 6H), 6.7–6.5 (m, 3H), 4.5 (t, 1H, J=9 Hz), 3.9 (m, 1H), 3.7 (s, 3H), 3.6 (m, 1H), 3.3 (m, 1H), 2.7 (t, 1H, J=6 Hz), 2.4 (s, 3H), 2.3–1.9 (m, 6H); APCI MS m/z 477 (M+H)$^+$.

Example 11

1-[(3-Fluoro-2'-methanesulfinyl)[1,1'-biphenyl]-4-yl]-3-(6-methoxy-3,4-dihydro-2H-quinolin-1-yl) piperidin-2-one A stirred solution of the compound of Ex. 10 (100 mg, 0.21 mmol) in acetone (0.75 mL) and 0.05 M phosphate buffer (pH =8, 0.25 mL) was treated with oxone (100 mg, 0.26 mmol) and stirred at room temperature for 10 h. The reaction mixture was diluted with H$_2$O and extracted with EtOAc (3×50 mL). The combined organic extracts were dried over Na$_2$SO$_4$, filtered, and concentrated. The residue was purified by column chromatography to provide the target compound (50 mg, 49%): $^1$H NMR (300 MHz, CDCl$_3$) δ 8.1 (d, 1H, J=8 Hz), 7.6 (t, 1H, J=6 Hz), 7.5 (t, 1H, J=6 Hz), 7.3–7.0 (m, 5H), 6.7–6.4 (m, 2H), 4.4 (t, 1H, J=9 Hz), 3.9 (m, 1H), 3.7 (s, 3H), 3.6 (m, 1H), 3.4–3.1 (m, 2H), 2.8 (t, 1H, J=6 Hz), 2.4 (s, 3H), 2.3–1.9 (m, 6H); APCI MS m/z 493 (M+H)$^+$.

Example 12

1-{1-[3-Fluoro-2'-(methylsulfonyl)[1,1'-biphenyl]-4-yl]-2-oxo-piperidin-3-yl]-5-methoxy-1,3-dihydrobenzimidazol-2-one This compound was prepared from the compound of Ex. 3, Part B and 5-methoxy-1,3-dihydrobenzimidazol-2-one according to the procedure described in example 3, Part C.

Example 13

1-1-[3-Fluoro-2'-methylsulfonyl-[1,1'-biphenyl]-4-yl]-2-oxo-piperidin-3-yl]-3-isopropyl-5-methoxy-1,3-dihydrobenzimidazol-2-one A mixture of the compound of Ex. 12 (25 mg, 0.049 mmol), isopropyl iodide (2 eq.) and cesium carbonate (2 eq.) in DMF (2 ml) was stirred at RT for 18 h. The mixture was diluted with water and extracted with ethyl acetate (3×). The combined extracts were washed with brine, dried over anhydrous magnesium sulfate, filtered and concentrated to dryness. The residue was purified by silica gel chromatography (ethyl acetate/hexane 3:1) to give the target compound (15 mg, 55%) $^1$H-NMR (CDCl$_3$, 300 MHz) δ 8.21 (d, J=7.6 Hz, 1H), 7.63 (m, 2H), 7.35 (m, 4H), 7.05 (d, J=7.6 Hz, 1H), 6.60 (m, 2H), 5.20 (m, 1H), 4.70 (m, 1H), 4.00 (m, 1H), 3.83 (s, 3H), 3.80 (m, 1H), 2.70 (s, 3H), 2.55 (m, 1H), 2.30 (m, 3H), 1.67 (m, 6H); mass spectrum, ESI (M+H)$^+$ 552.4, (M+Na)$^+$ 574.4.

Example 14

1-[1-[2'-tert-Butylsulfamoyl-3-fluoro-[1,1'-biphenyl]-4-yl]-2-oxo-pyrrolidin-3-yl]-1H-indole-6-carboximidamide Part A. 3-bromo-1-(4-bromo-2-fluorophenyl)pyrrolidin-2-one:

A stirred solution of 2,4-dibromobutyryl chloride (20 g, 76 mmol) and 4-bromo-2-fluoroaniline (14.4 g, 76 mmol) in CHCl$_3$ (80 mL) and H$_2$O (6 mL) was treated with 50% NaOH (15 mL) and stirred rapidly for 2 h. The reaction mixture was diluted with H$_2$O (50 mL) and extracted with CH$_2$Cl$_2$ (3×100 mL). The combined organic extracts were dried over Na$_2$SO$_4$, filtered, and concentrated. The residue was dissolved in THF (100 mL), cooled to 0° C., and treated with NaH (2 g, 87 mmol). The reaction mixture was warmed to room temperature and stirred for 2 h. The reaction mixture was then cooled to 0° C. and quenched with NH$_4$Cl. The organic phase was washed with NaHCO$_3$ and brine, dried over Na$_2$SO$_4$, filtered, and concentrated. The residue was purified by recrystallization from hexanes to the desired product (17.6 g, 69%): $^1$H NMR (300 MHz, CDCl$_3$) δ 7.4 (m, 6H), 4.5 (dd, 1H, J=3, 6.5 Hz), 4.0 (m, 1H), 3.8 (m, 1H), 2.8 (m, 1H), 2.5 (m, 1H); ESI MS m/z 336 (M+H)$^+$.

Part B. 1-[1-(4-bromo-2-fluorophenyl)-2-oxopyrrolidin-3-yl]-1H-indole-6-carbonitrile (20):

A stirred solution of 1H-indole-6-carbonitrile (250 mg, 1.8 mmol, U.S. Pat. No. 3,976,639) in THF (20 mL) was cooled to 0° C. and treated with NaH (50% w/w, 93 mg, 1.9 mmol) followed by the compound of Ex. 14, Part A (647 mg, 1.9 mmol) in THF (5 mL). The reaction was warmed to room temperature and stirred for 12 h. The reaction mixture was cooled to 0° C. and quenched with NH$_4$Cl. The organic phase was washed with NaHCO$_3$ and brine, dried over Na$_2$SO$_4$, filtered, and concentrated. The residue was purified by column chromatography to provide the product (422 mg, 60%): $^1$H NMR (300 MHz, CDCl$_3$) δ 7.7 (m, 2H), 7.5–7.1 (m, 7H), 6.7 (d, 1H, J=7 Hz), 5.3 (m, 2H), 4.1–3.8 (m, 2H), 3.0–2.8 (m, 1H), 2.6–2.4 (m, 1H); ESI MS m/z 398 (M+H)$^+$.

Part C. 4-[3-(6-cyanoindol-1-yl)-2-oxopyrrolidin-1-yl]-3'-fluorobiphenyl-2-sulfonic acid tert-butylamide:

A stirred mixture of the compound of Ex. 14, Part B (258 mg, 0.65 mmol), 2-tert-butylaminosulfonylphenylboronic acid (256 mg, 1.0 mmol), 2 M sodium carbonate (1.6 mmol, 0.8 mL), and benzene (5 mL) was degassed with argon for 30 minutes then Pd(PPh$_3$)$_4$ (37 mg, 0.03 mmol) was added. The reaction mixture was heated at 80° C. for 2 d and then diluted with EtOAc (20 mL), washed with water (20 mL) and brine (20 mL), dried over Na$_2$SO$_4$, and concentrated. Purification of the residue by column chromatography provided the coupled product (322 mg, 93%): $^1$H NMR (300 MHz, CDCl$_3$) δ 8.19 (d, 1H), 7.73 (m, 2H), 7.56 (m, 3H), 7.38 (m, 5H), 6.68 (d, 1H), 5.36 (dd, 1H), 4.13 (m, 2H), 2.90 (m, 1H), 2.53 (m, 1H), 1.07 (s, 9H).

Part D. 1-[1-(3-fluoro-2'-sulfamoyl-biphenyl-4-yl)-2-oxopyrrolidin-3-yl]-1H-indole-6-carboximidamide:

A stirred solution the compound of Ex. 14, Part C (316 mg, 0.596 mmol) in freshly distilled, dry EtOH (25 mL) was cooled to 0° C. and saturated with hydrogen chloride under a nitrogen atmosphere for 30 minutes. The reaction vessel was sealed and maintained at −20° C. for 24 h. The reaction was monitored by HPLC until the starting material was consumed, and then the reaction mixture was concentrated. The residue was dissolved in anhydrous ethanol and treated with an excess of (NH$_4$)$_2$CO$_3$ (573 mg, 6 mmol). The reaction vessel was sealed, stirred at room temperature for 12 h, and concentrated. Purification by column chromatography provided the title compound(102 mg, 31%) as a white solid: 1H NMR (300 MHz, DMSO-d$_6$) δ 8.07 (m, 2H), 7.77 (m, 2H), 7.66 (m, 3H), 7.51 (d, 1H), 7.37 (m, 2H), 7.31 (d, 1H), 6.69 (d, 1H), 5.78 (t, 1H), 4.05 (m, 2H), 2.82 (m, 1H), 2.65 (m, 1H), 1.05 (s, 9H); ESI MS m/z 548 (M+H)$^+$.

Example 15

1-[1-[3-Fluoro-2'-sulfamoyl-[1,1'-biphenyl]-4-yl]-2-oxopyrrolidin-3-yl]-1H-indole-6-carboximidamide This compound was also obtained as a white solid as a second component from Ex. 14, Part D (149 mg, 50%) after column chromatography: $^1$H NMR (300 MHz, DMSO-d$_6$) δ

8.13 (s, 1H), 8.06 (dd, 1H), 7.79 (m, 2H), 7.63 (m, 3H), 7.52 (d, 1H), 7.38 (m, 3H), 6.70 (d, 1H), 5.80 (t, 1H), 4.01 (m, 2H), 2.82 (m, 1H), 2.72 (m, 1H); ESI MS m/z 492 (M+H)+.
The following nomenclature is intended for group A in the following tables.
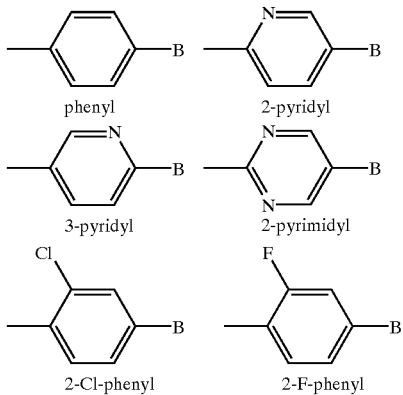
Table 1 demonstrates representative examples of G ring in Formula (Ia).
TABLE 1
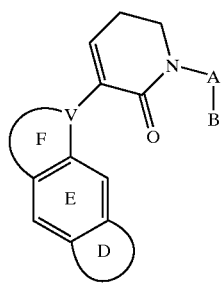
I-1
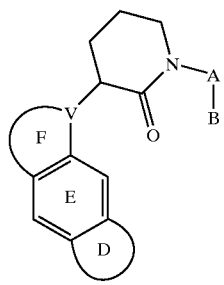
I-2
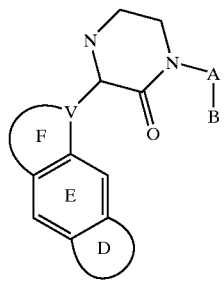
I-3
TABLE 1-continued
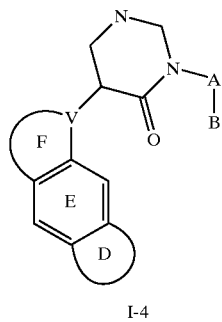
I-4
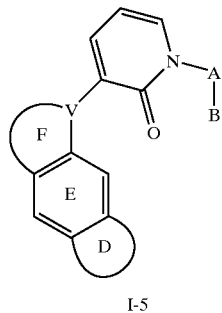
I-5
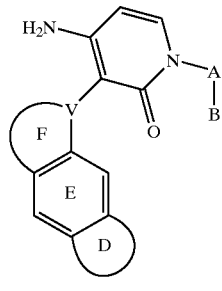
I-6
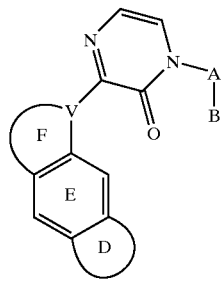
I-7

TABLE 1-continued
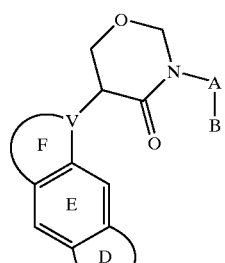
I-8
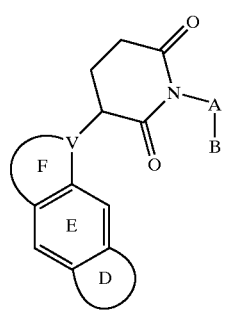
I-9
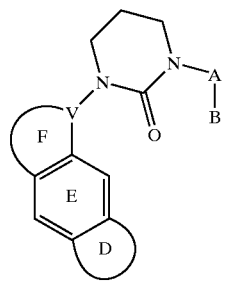
I-10
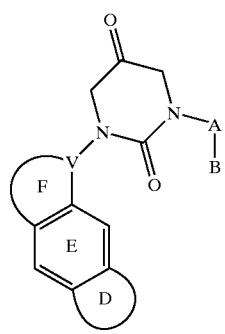
I-11
TABLE 1-continued
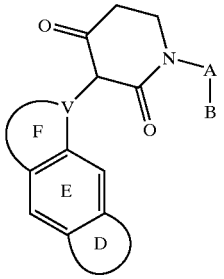
I-12
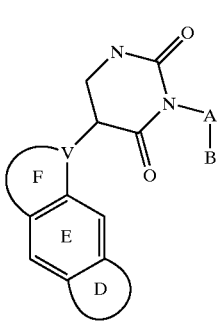
I-13
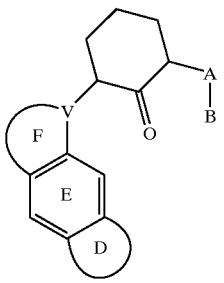
I-14
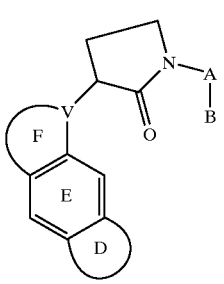
I-15

TABLE 1-continued
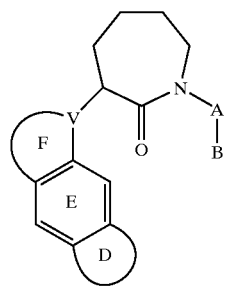
I-16
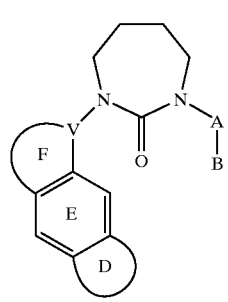
I-17
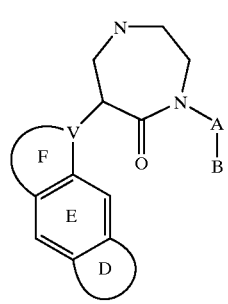
I-18
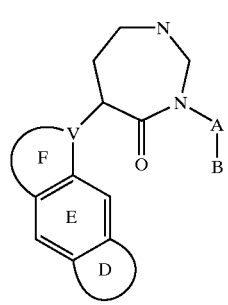
I-19
TABLE 2
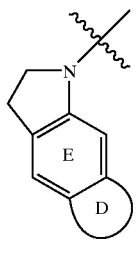
F-1
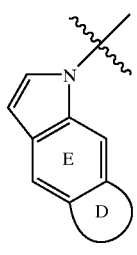
F-2
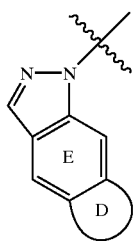
F-3
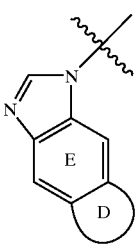
F-4
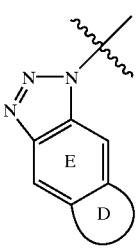
F-5
Table 2 demonstrates representative examples of ring F in Formula (Ia).

TABLE 2-continued
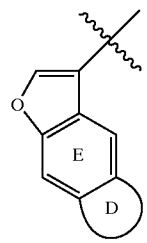
F-6
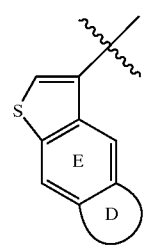
F-7
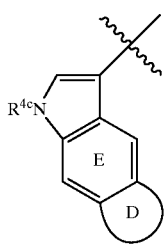
F-8
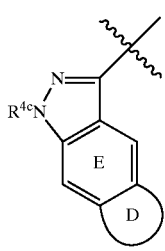
F-9
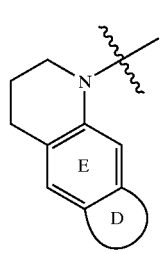
F-10
TABLE 2-continued
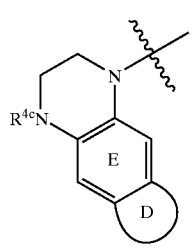
F-11
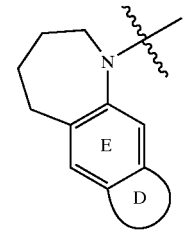
F-12
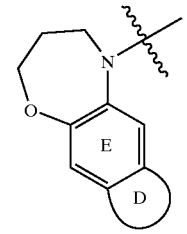
F-13
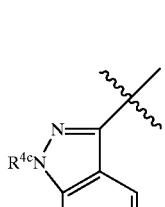
F-14
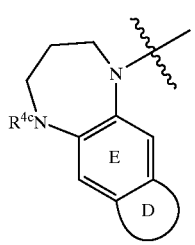
F-15

TABLE 2-continued
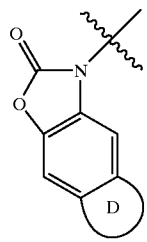
F-16
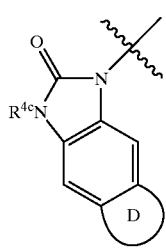
F-17
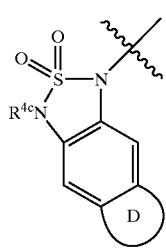
F-18
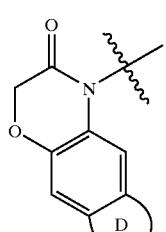
F-19
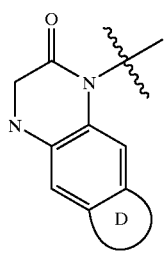
F-20
TABLE 2-continued
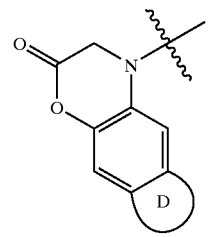
F-21
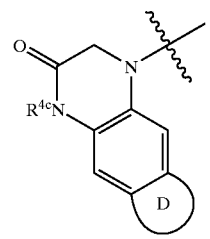
F-22
Table 3 demonstrates representative examples of rings D-E in Formula (Ia).
TABLE 3
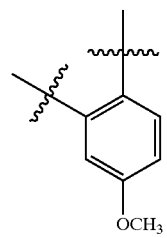
D-E-1
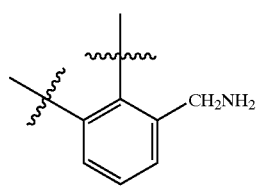
D-E-2
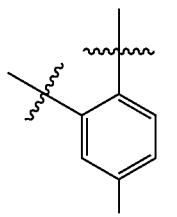
D-E-3

TABLE 3-continued
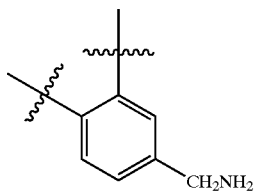
D-E-4
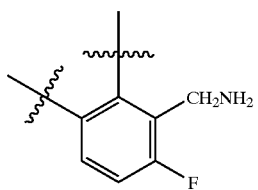
D-E-5
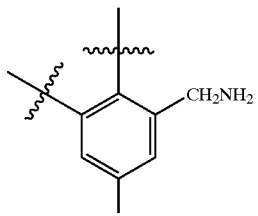
D-E-6
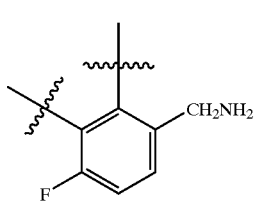
D-E-7
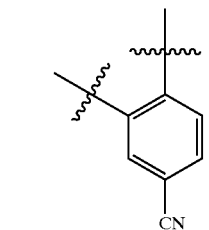
D-E-8
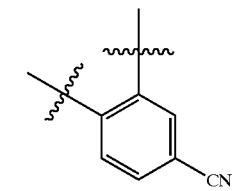
D-E-9
TABLE 3-continued
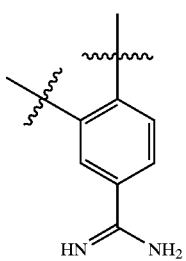
D-E-10
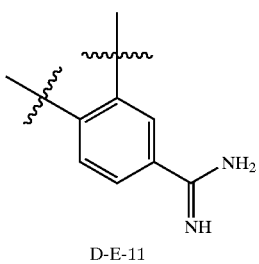
D-E-11
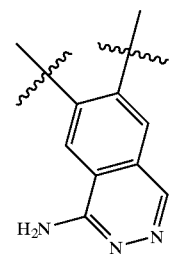
D-E-12
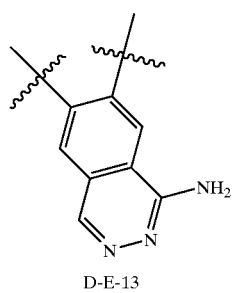
D-E-13
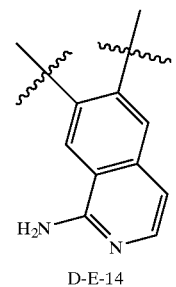
D-E-14

TABLE 3-continued

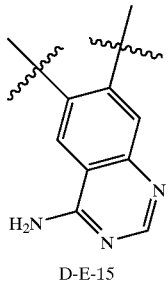

D-E-15

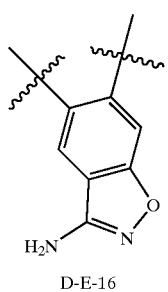

D-E-16

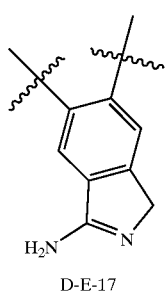

D-E-17

The following tables contain representative examples of the present invention. Each entry in Table 1 is intended to be combined with each formula at the start through to the end of the tables 2–3.

TABLE 4-1

Examples 1–104 use Structures I-1 in Table 1 and F-1 in Table 2 and D-E-1 in Table 3.

| EX # | A | B |
|---|---|---|
| 1 | phenyl | 2-($NH_2SO_2$)phenyl |
| 2 | phenyl | 2-($CH_3SO_2$)phenyl |
| 3 | phenyl | 3-$NH_2SO_2$-4-pyridyl |
| 4 | phenyl | 3-$CH_3SO_2$-4-pyridyl |
| 5 | phenyl | 2-($CH_3NH$)phenyl |
| 6 | phenyl | 2-(($CH_3)_2NCH_2$)phenyl |
| 7 | phenyl | 3-(($CH_3)_2NCH_2$)-4-pyridyl |
| 8 | phenyl | 2-(($CH_3SO_2$)N($CH_3$)$CH_2$)phenyl |
| 9 | phenyl | 2-(($CH_3C(O)$)N($CH_3$)$CH_2$)phenyl |
| 10 | phenyl | 2-(N-(3-R-HO-pyrrolidinyl)$CH_2$)phenyl |
| 11 | phenyl | 2-(N-(4-HO-piperidinyl)$CH_2$)phenyl |
| 12 | phenyl | 2-($CH_3NHC(O)N(CH_3)CH_2$)phenyl |
| 13 | phenyl | 1-$CH_3$-2-imidazolyl |
| 14 | 2-pyridyl | 2-($NH_2SO_2$)phenyl |
| 15 | 2-pyridyl | 2-($CH_3SO_2$)phenyl |
| 16 | 2-pyridyl | 3-$NH_2SO_2$-4-pyridyl |
| 17 | 2-pyridyl | 3-$CH_3SO_2$-4-pyridyl |
| 18 | 2-pyridyl | 2-($CH_3NH$)phenyl |
| 19 | 2-pyridyl | 2-(($CH_3)_2NCH_2$)phenyl |
| 20 | 2-pyridyl | 3-(($CH_3)_2NCH_2$)-4-pyridyl |
| 21 | 2-pyridyl | 2-(($CH_3SO_2$)N($CH_3$)$CH_2$)phenyl |
| 22 | 2-pyridyl | 2-(($CH_3C(O)$)N($CH_3$)$CH_2$)phenyl |
| 23 | 2-pyridyl | 2-(N-(3-R-HO-pyrrolidinyl)$CH_2$)phenyl |
| 24 | 2-pyridyl | 2-(N-(4-HO-piperidinyl)$CH_2$)phenyl |
| 25 | 2-pyridyl | 2-($CH_3NHC(O)N(CH_3)CH_2$)phenyl |
| 26 | 2-pyridyl | 1-$CH_3$-2-imidazolyl |
| 27 | 3-pyridyl | 2-($NH_2SO_2$)phenyl |
| 28 | 3-pyridyl | 2-($CH_3SO_2$)phenyl |
| 29 | 3-pyridyl | 3-$NH_2SO_2$-4-pyridyl |
| 30 | 3-pyridyl | 3-$CH_3SO_2$-4-pyridyl |
| 31 | 3-pyridyl | 2-($CH_3NH$)phenyl |
| 32 | 3-pyridyl | 2-(($CH_3)_2NCH_2$)phenyl |
| 33 | 3-pyridyl | 3-(($CH_3)_2NCH_2$)-4-pyridyl |
| 34 | 3-pyridyl | 2-(($CH_3SO_2$)N($CH_3$)$CH_2$)phenyl |
| 35 | 3-pyridyl | 2-(($CH_3C(O)$)N($CH_3$)$CH_2$)phenyl |
| 36 | 3-pyridyl | 2-(N-(3-R-HO-pyrrolidinyl)$CH_2$)phenyl |
| 37 | 3-pyridyl | 2-(N-(4-HO-piperidinyl)$CH_2$)phenyl |
| 38 | 3-pyridyl | 2-($CH_3NHC(O)N(CH_3)CH_2$)phenyl |
| 39 | 3-pyridyl | 1-$CH_3$-2-imidazolyl |
| 40 | 2-pyrimidyl | 2-($NH_2SO_2$)phenyl |
| 41 | 2-pyrimidyl | 2-($CH_3SO_2$)phenyl |
| 42 | 2-pyrimidyl | 3-$NH_2SO_2$-4-pyridyl |
| 43 | 2-pyrimidyl | 3-$CH_3SO_2$-4-pyridyl |
| 44 | 2-pyrimidyl | 2-($CH_3NH$)phenyl |
| 45 | 2-pyrimidyl | 2-(($CH_3)_2NCH_2$)phenyl |
| 46 | 2-pyrimidyl | 3-(($CH_3)_2NCH_2$)-4-pyridyl |
| 47 | 2-pyrimidyl | 2-(($CH_3SO_2$)N($CH_3$)$CH_2$)phenyl |
| 48 | 2-pyrimidyl | 2-(($CH_3C(O)$)N($CH_3$)$CH_2$)phenyl |
| 49 | 2-pyrimidyl | 2-(N-(3-R-HO-pyrrolidinyl)$CH_2$)phenyl |
| 50 | 2-pyrimidyl | 2-(N-(4-HO-piperidinyl)$CH_2$)phenyl |
| 51 | 2-pyrimidyl | 2-($CH_3NHC(O)N(CH_3)CH_2$)phenyl |
| 52 | 2-pyrimidyl | 1-$CH_3$-2-imidazolyl |
| 53 | 5-pyrimidyl | 2-($NH_2SO_2$)phenyl |
| 54 | 5-pyrimidyl | 2-($CH_3SO_2$)phenyl |
| 55 | 5-pyrimidyl | 3-$NH_2SO_2$-4-pyridyl |
| 56 | 5-pyrimidyl | 3-$CH_3SO_2$-4-pyridyl |
| 57 | 5-pyrimidyl | 2-($CH_3NH$)phenyl |
| 58 | 5-pyrimidyl | 2-(($CH_3)_2NCH_2$)phenyl |
| 59 | 5-pyrimidyl | 3-(($CH_3)_2NCH_2$)-4-pyridyl |
| 60 | 5-pyrimidyl | 2-(($CH_3SO_2$)N($CH_3$)$CH_2$)phenyl |
| 61 | 5-pyrimidyl | 2-(($CH_3C(O)$)N($CH_3$)$CH_2$)phenyl |
| 62 | 5-pyrimidyl | 2-(N-(3-R-HO-pyrrolidinyl)$CH_2$)phenyl |
| 63 | 5-pyrimidyl | 2-(N-(4-HO-piperidinyl)$CH_2$)phenyl |
| 64 | 5-pyrimidyl | 2-($CH_3NHC(O)N(CH_3)CH_2$)phenyl |
| 65 | 5-pyrimidyl | 1-$CH_3$-2-imidazolyl |
| 66 | 2-Cl-phenyl | 2-($NH_2SO_2$)phenyl |
| 67 | 2-Cl-phenyl | 2-($CH_3SO_2$)phenyl |
| 68 | 2-Cl-phenyl | 3-$NH_2SO_2$-4-pyridyl |
| 69 | 2-Cl-phenyl | 3-$CH_3SO_2$-4-pyridyl |
| 70 | 2-Cl-phenyl | 2-($CH_3NH$)phenyl |
| 71 | 2-Cl-phenyl | 2-(($CH_3)_2NCH_2$)phenyl |
| 72 | 2-Cl-phenyl | 3-(($CH_3)_2NCH_2$)-4-pyridyl |
| 73 | 2-Cl-phenyl | 2-(($CH_3SO_2$)N($CH_3$)$CH_2$)phenyl |
| 74 | 2-Cl-phenyl | 2-(($CH_3C(O)$)N($CH_3$)$CH_2$)phenyl |
| 75 | 2-Cl-phenyl | 2-(N-(3-R-HO-pyrrolidinyl)$CH_2$)phenyl |
| 76 | 2-Cl-phenyl | 2-(N-(4-HO-piperidinyl)$CH_2$)phenyl |
| 77 | 2-Cl-phenyl | 2-($CH_3NHC(O)N(CH_3)CH_2$)phenyl |
| 78 | 2-Cl-phenyl | 1-$CH_3$-2-imidazolyl |
| 79 | 2-F-phenyl | 2-($NH_2SO_2$)phenyl |
| 80 | 2-F-phenyl | 2-($CH_3SO_2$)phenyl |
| 81 | 2-F-phenyl | 3-$NH_2SO_2$-4-pyridyl |
| 82 | 2-F-phenyl | 3-$CH_3SO_2$-4-pyridyl |
| 83 | 2-F-phenyl | 2-($CH_3NH$)phenyl |
| 84 | 2-F-phenyl | 2-(($CH_3)_2NCH_2$)phenyl |
| 85 | 2-F-phenyl | 3-(($CH_3)_2NCH_2$)-4-pyridyl |
| 86 | 2-F-phenyl | 2-(($CH_3SO_2$)N($CH_3$)$CH_2$)phenyl |
| 87 | 2-F-phenyl | 2-(($CH_3C(O)$)N($CH_3$)$CH_2$)phenyl |
| 88 | 2-F-phenyl | 2-(N-(3-R-HO- |

TABLE 4-1-continued

Examples 1–104 use Structures I-1 in Table 1 and F-1 in Table 2 and D-E-1 in Table 3.

| EX # | A | B |
|---|---|---|
| 89 | 2-F-phenyl | 2-(N-(4-HO-piperidinyl)CH$_2$)phenyl |
| 90 | 2-F-phenyl | 2-(CH$_3$NHC(O)N(CH$_3$)CH$_2$)phenyl |
| 91 | 2-F-phenyl | 1-CH$_3$-2-imidazolyl |
| 92 | 2,6-diF-phenyl | 2-(NH$_2$SO$_2$)phenyl |
| 93 | 2,6-diF-phenyl | 2-(CH$_3$SO$_2$)phenyl |
| 94 | 2,6-diF-phenyl | 3-NH$_2$SO$_2$-4-pyridyl |
| 95 | 2,6-diF-phenyl | 3-CH$_3$SO$_2$-4-pyridyl |
| 96 | 2,6-diF-phenyl | 2-(CH$_3$NH)phenyl |
| 97 | 2,6-diF-phenyl | 2-((CH$_3$)$_2$NCH$_2$)phenyl |
| 98 | 2,6-diF-phenyl | 3-((CH$_3$)$_2$NCH$_2$)-4-pyridyl |
| 99 | 2,6-diF-phenyl | 2-((CH$_3$SO$_2$)N(CH$_3$)CH$_2$)phenyl |
| 100 | 2,6-diF-phenyl | 2-((CH$_3$C(O))N(CH$_3$)CH$_2$)phenyl |
| 101 | 2,6-diF-phenyl | 2-(N-(3-R-HO-pyrrolidinyl)CH$_2$)phenyl |
| 102 | 2,6-diF-phenyl | 2-(N-(4-HO-piperidinyl)CH$_2$)phenyl |
| 103 | 2,6-diF-phenyl | 2-(CH$_3$NHC(O)N(CH$_3$)CH$_2$)phenyl |
| 104 | 2,6-diF-phenyl | 1-CH$_3$-2-imidazolyl |

Examples 105–1768 use the corresponding A and B groups from Examples 1–104 and the recited D-E groups in Table 3 as follows:

Examples 105–208, D-E is D-E-2;

Examples 209–312, D-E is D-E-3;

Examples 313–416, D-E is D-E-4;

Examples 417–520, D-E is D-E-5;

Examples 521–624, D-E is D-E-6;

Examples 625–728, D-E is D-E-7;

Examples 729–832, D-E is D-E-8;

Examples 833–936, D-E is D-E-9;

Examples 937–1040, D-E is D-E-10;

Examples 1041–1144, D-E is D-E-11;

Examples 1145–1248, D-E is D-E-12;

Examples 1249–1352, D-E is D-E-13;

Examples 1353–1456, D-E is D-E-14;

Examples 1457–1560, D-E is D-E-15;

Examples 1561–1664, D-E is D-E-16;

Examples 1665–1768, D-E is D-E-17.

TABLE 4-2

Examples 1-1768 use Structures I-1 in Table 1 and F-2 in Table 2, and corresponding A and B groups in Table 4 and recited D–E groups in Table 3 in the same order as Table 4.

TABLE 4-3

Examples 1-1768 use Structures I-1 in Table 1 and F-3 in Table 2, and corresponding A and B groups in Table 4 and recited D–E groups in Table 3 in the same order as Table 4.

TABLE 4-4

Examples 1-1768 use Structures I-1 in Table 1 and F-4 in Table 2, and corresponding A and B groups in Table 4 and recited D–E groups in Table 3 in the same order as Table 4.

TABLE 4-5

Examples 1-1768 use Structures I-1 in Table 1 and F-5 in Table 2, and corresponding A and B groups in Table 4 and recited D–E groups in Table 3 in the same order as Table 4.

TABLE 4-6

Examples 1-1768 use Structures I-1 in Table 1 and F-6 in Table 2, and corresponding A and B groups in Table 4 and recited D–E groups in Table 3 in the same order as Table 4.

TABLE 4-7

Examples 1-1768 use Structures I-1 in Table 1 and F-7 in Table 2, and corresponding A and B groups in Table 4 and recited D–E groups in Table 3 in the same order as Table 4.

TABLE 4-8

Examples 1-1768 use Structures I-1 in Table 1 and F-8 in Table 2, and corresponding A and B groups in Table 4 and recited D–E groups in Table 3 in the same order as Table 4.

TABLE 4-9

Examples 1-1768 use Structures I-1 in Table 1 and F-9 in Table 2, and corresponding A and B groups in Table 4 and recited D–E groups in Table 3 in the same order as Table 4.

TABLE 4-10

Examples 1-1768 use Structures I-1 in Table 1 and F-10 in Table 2, and corresponding A and B groups in Table 4 and recited D–E groups in Table 3 in the same order as Table 4.

TABLE 4-11

Examples 1-1768 use Structures I-1 in Table 1 and F-11 in Table 2, and corresponding A and B groups in Table 4 and recited D–E groups in Table 3 in the same order as Table 4.

TABLE 4-12

Examples 1-1768 use Structures I-1 in Table 1 and F-12 in Table 2, and corresponding A and B groups in Table 4 and recited D–E groups in Table 3 in the same order as Table 4.

TABLE 4-13

Examples 1-1768 use Structures I-1 in Table 1 and F-13 in Table 2, and corresponding A and B groups in Table 4 and recited D–E groups in Table 3 in the same order as in Table 4.

TABLE 4-14

Examples 1-1768 use Structures I-1 in Table 1 and F-14 in Table 2, and corresponding A and B groups in Table 4 and recited D–E groups in Table 3 in the same order as in Table 4.

TABLE 4-15

Examples 1-1768 use Structures I-1 in Table 1 and F-15 in Table 2, and corresponding A and B groups in Table 4 and recited D–E groups in Table 3 in the same order as in Table 4.

TABLE 4-16

Examples 1-1768 use Structures I-1 in Table 1 and F-16 in Table 2, and corresponding A and B groups in Table 4 and recited D–E groups in Table 3 in the same order as in Table 4.

TABLE 4-17

Examples 1-1768 use Structures I-1 in Table 1 and F-17 in Table 2, and corresponding A and B groups in Table 4 and recited D–E groups in Table 3 in the same order as in Table 4.

TABLE 4-18

Examples 1-1768 use Structures I-1 in Table 1 and F-18 in Table 2, and corresponding A and B groups in Table 4 and recited D–E groups in Table 3 in the same order as in Table 4.

TABLE 4-19

Examples 1-1768 use Structures I-1 in Table 1 and F-19 in Table 2, and corresponding A and B groups in Table 4 and recited D–E groups in Table 3 in the same order as in Table 4.

TABLE 4-20

Examples 1-1768 use Structures I-1 in Table 1 and F-20 in Table 2, and corresponding A and B groups in Table 4 and recited D–E groups in Table 3 in the same order as in Table 4.

TABLE 4-21

Examples 1-1768 use Structures I-1 in Table 1 and F-21 in Table 2, and corresponding A and B groups in Table 4 and recited D–E groups in Table 3 in the same order as in Table 4.

TABLE 4-22

Examples 1-1768 use Structures I-1 in Table 1 and F-22 in Table 2, and corresponding A and B groups in Table 4 and recited D–E groups in Table 3 in the same order as in Table 4.

Structures I-2 to I-19 can be combined with Structures F-1 to F-22, D-E-1 to D-E-17 and corresponding A and B groups in Table 4-1 in the same fashion as Tables 4-1 to Table 4-22.

Other representative examples of ring F in Formula (Ia) are demonstrated in Table 5.

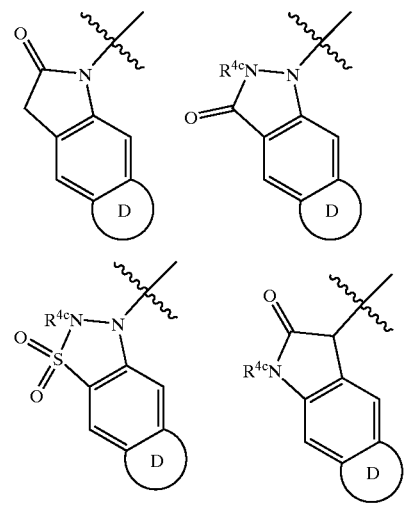

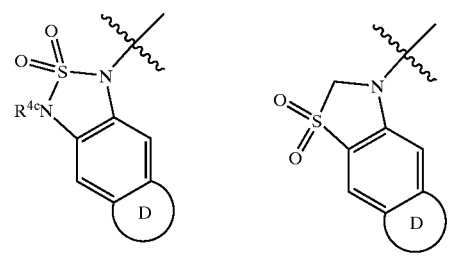

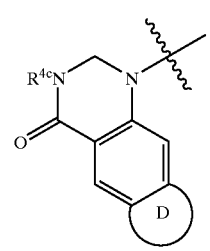

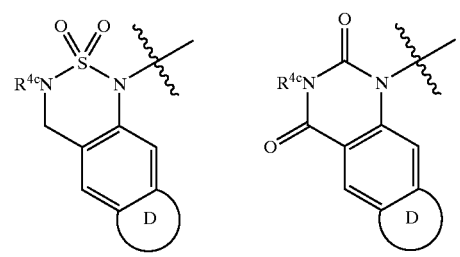

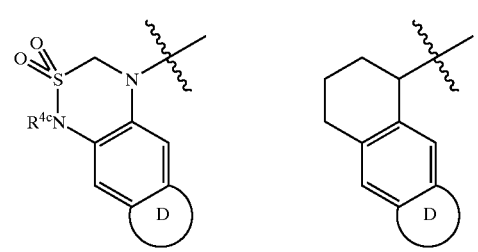

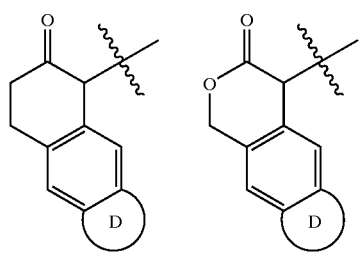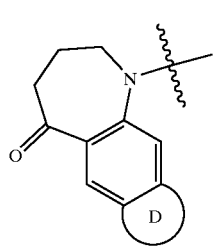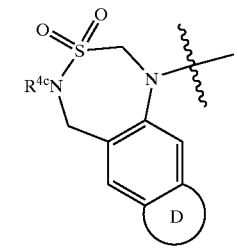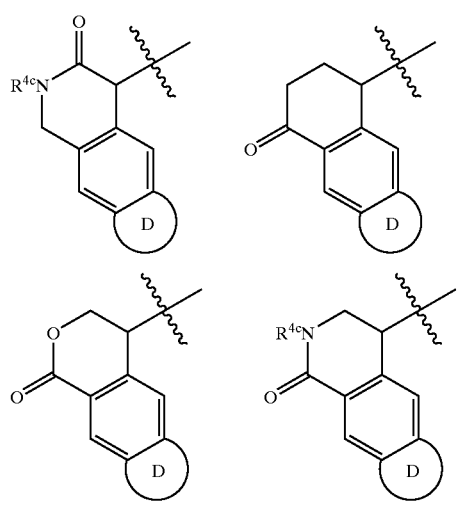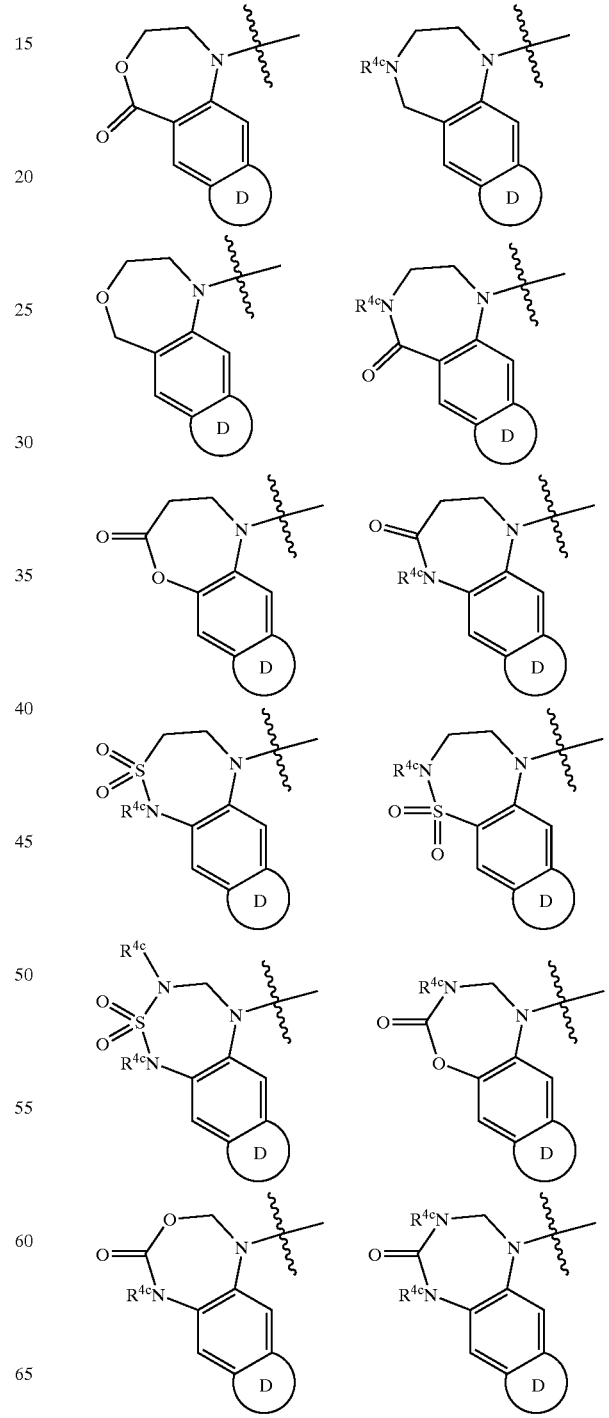

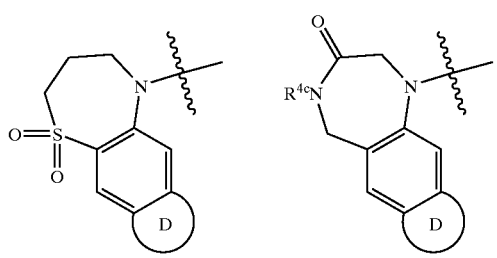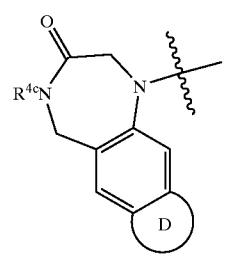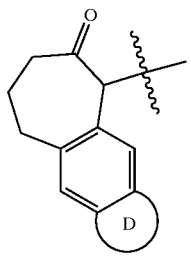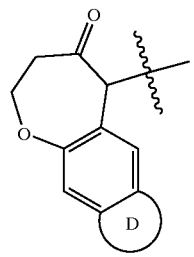
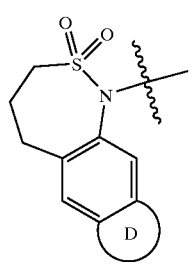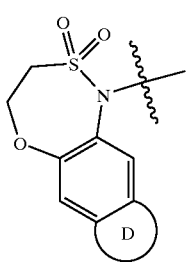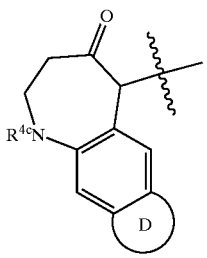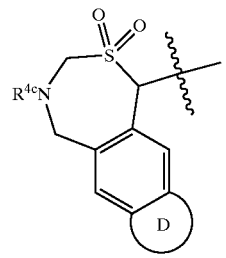
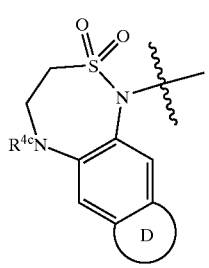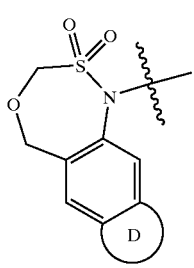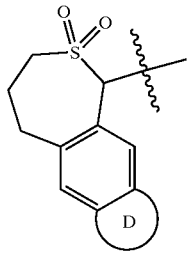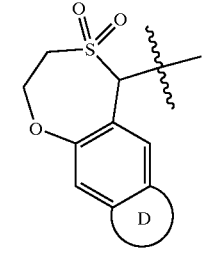
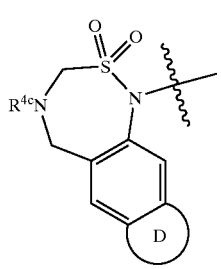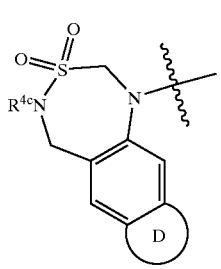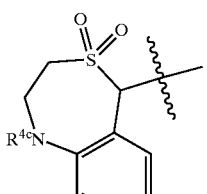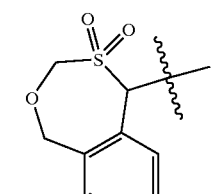
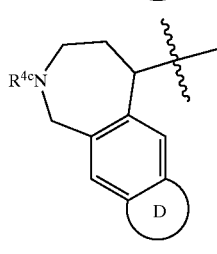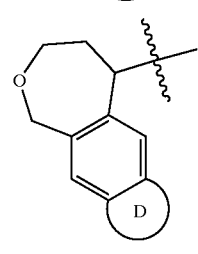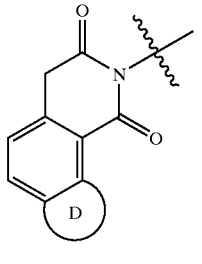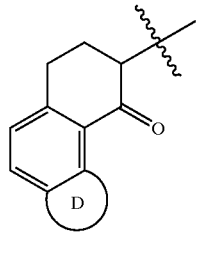
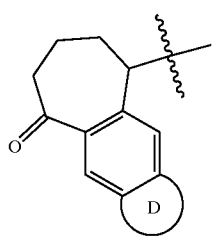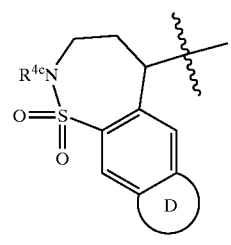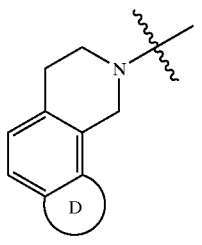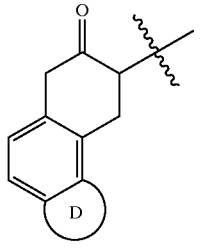

-continued

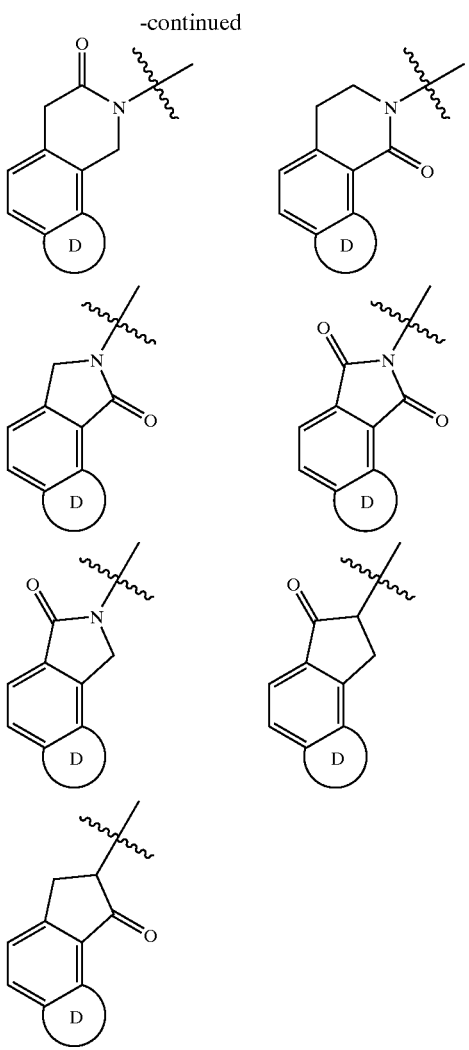

Numerous modifications and variations of the present invention are possible in light of the above teachings. It is therefore to be understood that within the scope of the appended claims, the invention may be practiced otherwise that as specifically described herein.

What is claimed is:

1. A compound of Formula (I):

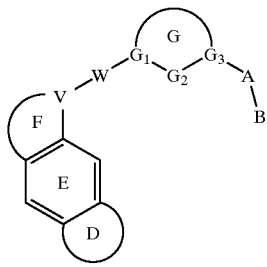

or a stereoisomer or pharmaceutically acceptable salt form thereof, wherein:

ring D is absent;

ring E is selected from phenyl, pyridyl, pyrimidyl, pyrazinyl, pyridazinyl, pyrrolyl, pyrazolyl, imidazolyl, isoxazolyl, oxazolyl, thiazolyl, thienyl and trizaolyl, and ring E is substituted with 0–2 $R^a$;

$R^a$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $C(O)NR^7R^8$, $(CR^8R^9)_rNR^7R^8$, SH, $SCH_3$, $SCH_2CH_3$, $SCH(CH_3)_2$, $SCH_2CH_2CH_3$, $S(O)R^{3b}$, $S(O)_2R^{3a}$, $S(O)_2NR^2R^{2a}$, and $OCF_3$;

alternatively, two $R^a$s combine to form methylenedioxy or ethylenedioxy;

alternatively, ring E is selected from phenyl, pyridyl, pyrimidyl, pyrazinyl, pyridazinyl, and thienyl, and ring E is substituted with 1 R and with a 5–6 membered aromatic heterocycle consisting of: carbon atoms and 1–4 heteroatoms selected from the group consisting of N, O, and $S(O)_p$ substituted with 0–1 carbonyl groups and 0–2 $R^1$;

ring F completes a 5–7 membered heterocycle consisting of carbon atoms, 1–3 heteroatoms selected from the group consisting of N, NH, O, and $—S(O)_p—$, 0–2 additional double bonds, and 0–2 carbonyl groups, provided that other than a O—O, O—S, or S—S bond is present in the ring and ring F is substituted with 0–1 $R^{4c}$;

ring G is substituted with 0–2 $R^{1a}$ and is selected from:

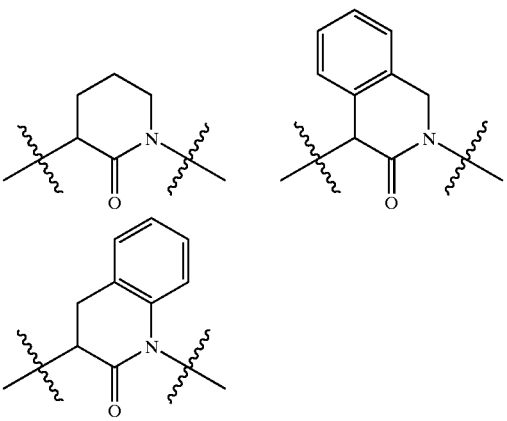

Z is selected from H, $S(O)_2NHR^3$, $C(O)R^3$, $C(O)NHR^3$, $C(O)OR^{3f}$, $S(O)R^{3f}$, $S(O)_2R^{3f}$, $C_{1-6}$ alkyl substituted with 0–2 $R^{1a}$;
$C_{2-6}$ alkenyl substituted with 0–2 $R^{1a}$;
$C_{2-6}$ alkynyl substituted with 0–2 $R^{1a}$;
—$(C_{0-4}$ alkyl)-$C_{3-10}$-carbocycle substituted with 0–3 $R^{1a}$; and
—$(C_{0-4}$ alkyl)-5–12 membered-heterocycle substituted with 0–3 $R^{1a}$;

A is selected from:
$C_{3-10}$ carbocycle substituted with 0–2 $R^4$, and
5–12 membered heterocycle consisting of carbon atoms and from 1–4 heteroatoms selected from the group consisting of N, O, and S and substituted with 0–2 $R^4$;

B is selected from: Y, X—Y, $(CH_2)_{0-2}C(O)NR^2R^{2a}$, $(CH_2)_{0-2}NR^2R^{2a}$, $C(=NR^2)NR^2R^{2a}$, and $NR^2C(=NR^2)NR^2R^{2a}$, provided that $G_3$ and B are attached to different atoms on A;

X is selected from —$(CR^2R^{2a})_{1-4}$—, —$CR^2(CR^2R^{2b})$ $(CH_2)_t$—, —C(O)—, —C(=$NR^{1c}$)—, —$CR^2$ $(NR^2R^{2a})$—, —$CR^2(OR^2)$—, —$CR^2(SR^2)$—, —$C(O)$ $CR^2R^{2a}$—, —$CR^2R^{2a}C(O)$, —S—, —S(O)—, —S(O)$_2$—, —$SCR^2R^{2a}$—, —$S(O)CR^2R^{2a}$—, —$S(O)_2CR^2R^{2a}$—, —$CR^2R^{2a}S$—, —$CR^2R^{2a}S(O)$—, —$CR^2R^{2a}S(O)_2$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
 —$(CH_2)_rNR^2R^{2a}$;
 $C_{3-10}$ carbocycle substituted with 0–2 $R^{4a}$; and
 5–10 membered heterocycle consisting of carbon atoms and from 1–4 heteroatoms selected from the group consisting of N, O, and S and substituted with 0–2 $R^{4a}$;

provided that X—Y do not form a N—N, O—N, or S—N bond;

V is selected from C, CH, and N;

W is a bond;

$R^1$ is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $NR^8CH(=NR^7)$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_tOR^{3a}$, $(CR^8R^9)_rNR^7C(O)R^7$, $(CR^8R^9)_tS(O)_pNR^7R^8$, $(CR^8R^9)_rNR^7S(O)_pR^7$, $(CR^8R^9)_rSR^3$, $(CR^8R^9)_rS(O)R^{3c}$, $(CR^8R^9)_rS(O)_2R^{3c}$, and $OCF_3$;

$R^{1a}$ is selected from H, —$(CH_2)_r$—$R^{1b}$, —CH=CH—$R^{1b}$, $NCH_2R^{1c}$, $NR^2R^{2a}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, $S(O)_p(CH_2)_rR^{1d}$, $O(CH_2)_rR^{1d}$, $NR^3(CH_2)_rR^{1d}$, $OC(O)NR^3(CH_2)_rR^{1d}$, $NR^3C(O)NR^3(CH_2)_rR^{1d}$, $NR^3C(O)O(CH_2)_rR^{1d}$, and $NR^3C(O)(CH_2)_rR^{1d}$, provided that $R^{1a}$ forms other than an N-halo, N—N, N—S, N—O, or N—CN bond;

alternatively, when two $R^{1a}$s are attached to adjacent atoms, together with the atoms to which they are attached they form a 5–7 membered ring consisting of: carbon atoms and 0–2 heteroatoms selected from the group consisting of N, O, and $S(O)_p$, 0–1 Z, and 0–3 ring double bonds; this ring being substituted with 0–2 $R^{4b}$;

$R^{1b}$ is selected from H, $C_{1-3}$ alkyl, F, Cl, Br, I, —ON, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-10}$ carbocycle substituted with 0–2 $R^{4a}$, and 5–10 membered heterocycle consisting of carbon atoms and from 1–4 heteroatoms selected from the group consisting of N, O, and $S(O)_p$, substituted with 0–2 $R^{4a}$, provided that $R^{1b}$ forms other than an N-halo, N—N, N—S, N—O, or N—CN bond with the group to which it is attached;

$R^{1c}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^{1d}$ is selected from $C_{3-6}$ carbocycle substituted with 0–2 $R^{4a}$, and 5–10 membered heterocycle consisting of carbon atoms and from 1–4 heteroatoms selected from the group consisting of N, O, and $S(O)_p$, and substituted with 0–2 $R^{4a}$, provided that $R^{1d}$ forms other than an N–N, N–S, or N–O bond;

$R^2$ and $R^{2a}$, at each occurrence, are independently selected from H, $CF_3$, $C_{1-6}$ alkyl, benzyl;
 —$(CH_2)_r$—$C_{3-10}$ carbocycle substituted with 0–2 $R^{4b}$; and
 —$(CH_2)_r$-5–6 membered heterocycle consisting of carbon atoms and from 1–4 heteroatoms selected from the group consisting of N, O, and $S(O)_p$, and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and consisting of: 0–1 additional heteroatoms selected from the group consisting of N, O, and $S(O)_p$;

$R^{2b}$ and $R^{2c}$, at each occurrence, are independent selected from $CF_3$, OH, $C_{1-4}$ alkoxy, $C_{1-6}$ alkyl, benzyl;
 —$(CH_2)_r$—$C_{3-10}$ carbocycle substituted with 0–2 $R^{4b}$; and
 —$(CH_2)_r$-5–6 membered heterocycle consisting of carbon atoms and from 1–4 heteroatoms selected from the group consisting of N, O, and $S(O)_p$, and substituted with 0–2 $R^{4b}$;

$R^3$ and $R^{3a}$, at each occurrence, is independently selected from H, $C_{1-4}$ alkyl, benzyl and phenyl;

$R^{3b}$, at each occurrence, is selected from H, $C_{1-6}$ alkyl substituted with 0–2 $R^{1a}$, $C_{2-6}$ alkenyl substituted with 0–2 $R^{1a}$, $C_{2-6}$ alkynyl substituted with 0–2 $R^{1a}$, —$(C_{0-4}$ alkyl)-cycloalkyl substituted with 0–3 $R^{1a}$, —$(C_{0-4}$ alkyl)-heterocycle substituted with 0–3 $R^{1a}$, —$(C_{0-4}$ alkyl)-aryl substituted with 0–3 $R^{1a}$, and —$(C_{0-4}$ alkyl)-heteroaryl substituted with 0–3 $R^{1a}$;

$R^{3c}$, at each occurrence, is selected from $C_{1-4}$ alkyl, benzyl, and phenyl;

$R^{3d}$, at each occurrence, is selected from H, $C_{1-4}$ alkyl, $C_{1-4}$ alkyl-phenyl, and $C(=O)R^{3c}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $NR^2C(O)R^{2b}$, $C(O)NR^2R^{2a}$, $NR^2C(O)NR^2R^{2a}$, $C(=NR^2)NR^2R^{2a}$, $C(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1c}$, $OCH_2R^{1c}$, $SCH_2R^{1c}$, $N(CH_2)_2(CH_2)_rR^{1b}$, $O(CH_2)_2(CH_2)_rR^{1b}$, and $S(CH_2)_2(CH_2)_rR^{1b}$;

alternatively, one $R^4$ is a $(CR^3R^{3a})$-5–6 membered aromatic heterocycle consisting of:
 carbon atoms and 1–4 heteroatoms selected from the group consisting of N, O, and $S(O)_p$;

$R^{4a}$, at each occurrence, is selected from H, =O, $(CR^3R^{3a})_rOR^2$, $(CR^3R^{3a})_rF$, $(CR^3R^{3a})_rBr$, $(CR^3R^{3a})_rCl$, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_rC(O)NH(CH_2)_2NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rNHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rC(O)NHSO_2$—$C_{1-4}$ alkyl, $(CR^3R^{3a})NR^2SO_2R^5$, $(CR^3R^{3a})_rS(O)_pR^5$, $(CR^3R^{3a})_r(CF^2)_rCF_3$, $(CR^3R^{3a})_r$-5–6 membered carbocycle substituted with 0–1 $R^5$, and a $(CR^3R^{3a})_r$-5–6 membered heterocycle consisting of: carbon atoms and 1–4 heteroatoms selected from the group consisting of N, O, and $S(O)_p$, and substituted with 0–1 $R^5$;

$R^{4b}$, at each occurrence, is selected from H, =O, $(CH_2)_rOR^3$, $(CH_2)_rF$, $(CH_2)_rCl$, $(CH_2)_rBr$, $(CH_2)_rI$, $C_{1-4}$ alkyl, $(CH_2)_rCN$, $(CH_2)_rNO_2$, $(CH_2)_rNR^3R^{3a}$, $(CH_2)_rC(O)R^3$, $(CH_2)_rC(O)OR^{3c}$, $(CH_2)_rNR^3C(O)R^{3a}$, $(CH_2)_rC(O)NR^3R^{3a}$, $(CH_2)_rNR^3C(O)NR^3R^{3a}$, $(CH_2)_r$—$C(=NR^3)NR^3R^{3a}$, $(CH_2)_rNR^3C(=NR^3)NR^3R^{3a}$, $(CH_2)_rSO_2NR^3R^{3a}$, $(CH_2)_rNR^3SO_2NR^3R^{3a}$, $(CH_2)_rNR^3SO_2$—$C_{1-4}$ alkyl, $(CH_2)_rNR^3SO_2CF_3$, $(CH_2)_rNR^3SO_2$-phenyl, $(CH_2)_rS(O)_pCF_3$, $(CH_2)_rS(O)_p$—$C_{1-4}$ alkyl, $(CH_2)_rS(O)_p$-phenyl, and $(CH_2)_r(CF_2)_tCF_3$;

$R^{4c}$ is selected from H, $C_{1-4}$ alkyl, —$(CH_2)_uOR^{3b}$, —$(CH_2)_uNR^{3b}R^{3b}$, —$CH_2)_uC(O)R^{3b}$, —$(CH_2)_uCO_2R^{3b}$, —$(CH_2)_uC(O)NR^{3b}R^{3b}$, —$(CH_2)_uSO_2NR^{3b}R^{3b}$, —$(CH_2)_uNHSO_2R^{3b}$, and $(CR^3R^{3a})_r$-5–6 membered carbocycle substituted with 0–1 $R^5$;

$R^5$, at each occurrence, is selected from H, $C_{1-6}$ alkyl, =O, $(CH_2)_rOR^3$, F, Cl, Br, I, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2CF_3$, $NR^3SO_2$-phenyl, $S(O)_pCF_3$, $S(O)_p$—$C_{1-4}$ alkyl, $S(O)_p$-phenyl, $(CF2)_rCF_3$, phenyl substituted with 0–2 $R^6$, naphthyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylainınocarbonyl, phenylaminocarbonyl, and phenyl $C_{1-4}$ alkoxycarbonyl;

$R^8$, at each occurrence, is selected from H, $C_{1-6}$ alkyl, and —$(CH_2)_n$-phenyl;

alternatively, $R^7$ and $R^8$, when attached to the same nitrogen, combine to form a 5 or 6 membered saturated ring consisting of carbon atoms and 0–2 additional heteroatoms selected from the group consisting of N, O, and $S(O)_p$;

$R^9$, at each occurrence, is selected from H, $C_{1-6}$ alkyl, and —$(CH_2)_n$-phenyl;

n, at each occurrence, is selected from 0, 1, 2, and 3;
p, at each occurrence, is selected from 0, 1, and 2;
r, at each occurrence, is selected from 0, 1, 2, and 3;
t, at each occurrence, is selected from 0, 1, 2, and 3; and,
u, at each occurrence, is selected from 1, 2, and 3.

2. A compound of claim 1, wherein:
the bridging portion of ring F completes a 5–7 membered heterocycle consisting of carbon atoms, 1–3 heteroatoms selected from the group consisting of N, NH, O, and S, 0–2 additional double bonds, and 0–2 carbonyl groups, provided that other than a O—O, O—S, or S—S bond is present in the ring and the bridging portion of ring F is substituted with 0–1 $R^{4c}$;

A is selected from one of the following carbocyclic and heterocyclic systems which are substituted with 0–2 $R^4$;

phenyl, piperidinyl, piperazinyl, pyridyl, pyriniidyl, furanyl, morpholinyl, thiophenyl, pyrrolyl, pyrrolidinyl, oxazolyl, isoxazolyl, thiazolyl, isotbiazolyl, pyrazolyl, imidazolyl, oxadiazolyl, thiadiazolyl, triazolyl, 1,2,3-oxadiazolyl, 1,2,4-oxadiazolyl, 1,2,S-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is X—Y or is selected from one of the following carbocyclic and heterocyclic systems which are substituted with 1–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=NR$^{1c}$)—, —CR$^2$(NR$^2$R$^{2a}$)—, —C(O)CR$^2$R$^{2a}$—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$—, and —OCR$^2$R$^{2a}$—;

Y is NR$^2$R$^{2a}$, provided that X—Y do not form a N—N or O—N bond;

alternatively, Y is selected from one of the following carbocyclic and heterocycles which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isotbiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

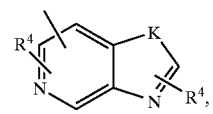 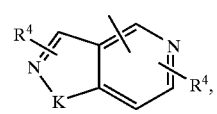

-continued
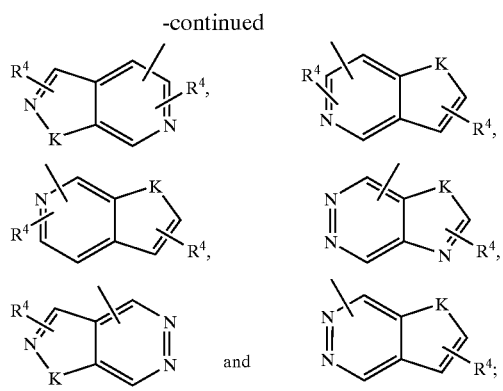
K is selected from O, S, NH, and N; and
V is selected from C, CH, and N.
3. A compound according to claim 1, wherein:
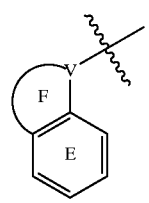
is selected from:
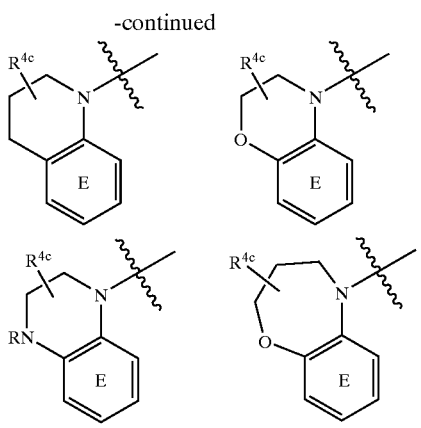
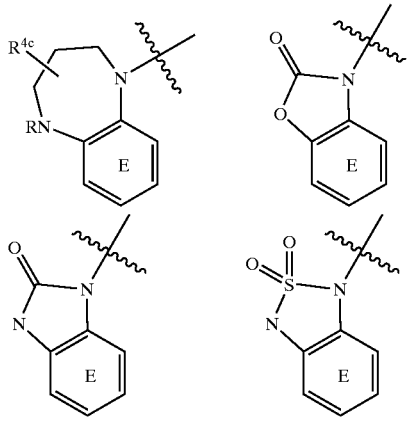
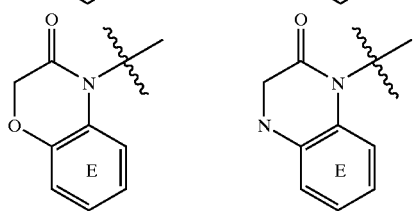
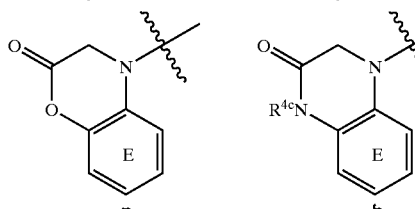
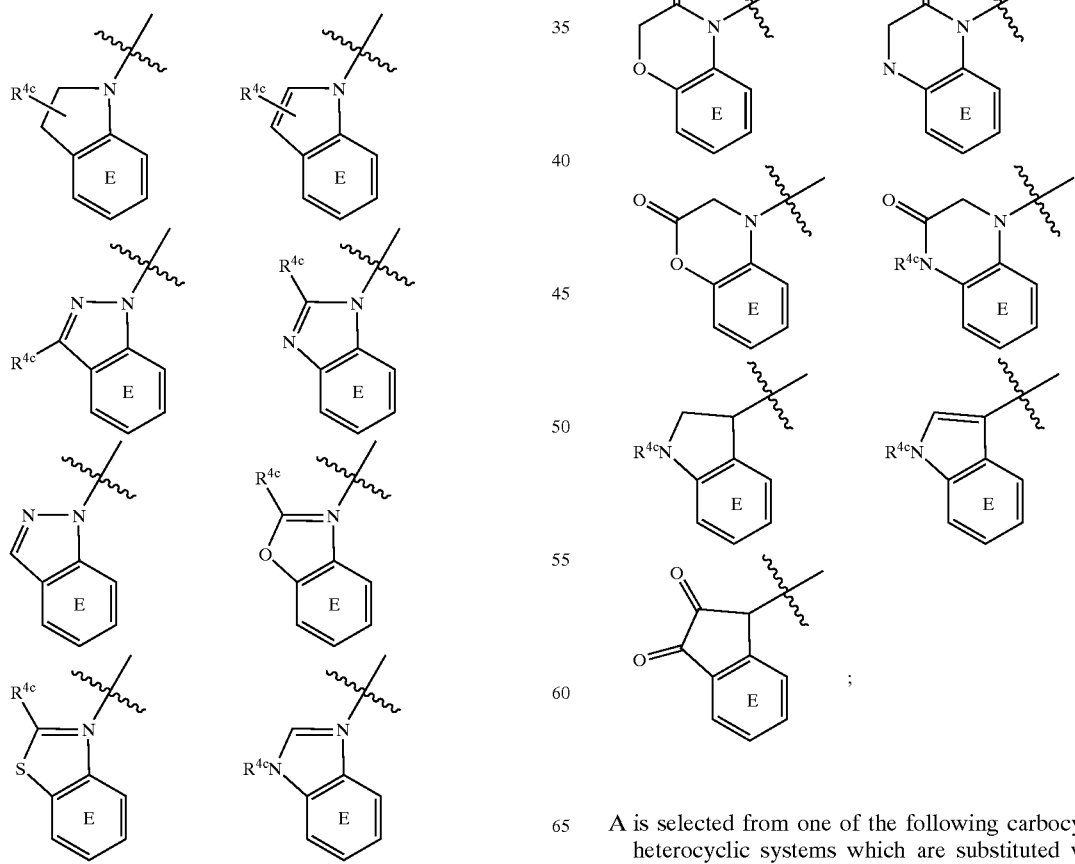
A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is X—Y or is selected from one of the following carbocyclic and heterocycles which are substituted with 1–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=$NR^{1c}$)—, —$CR^2(NR^2R^{2a})$—, —C(O)$CR^2R^{2a}$—, —$CR^2R^{2a}$C(O), —C(O)$NR^2$—, —$NR^2$C(O)—, —C(O)$NR^2CR^2R^{2a}$—, —$NR^2$C(O)$CR^2R^{2a}$—, —$CR^2R^{2a}$C(O)$NR^2$—, —$CR^2R^{2a}NR^2$C(O)—, —$NR^2$C(O)$NR^2$—, —$NR^2$—, —$NR^2CR^2R^{2a}$—, —$CR^2R^{2a}NR^2$—, O, —$CR^2R^{2a}$O—, and —$OCR^2R^{2a}$—;

Y is $(CH^2)_rNR^2R^{2a}$, provided that X—Y do not form a N—N or O—N bond;

alternatively, Y is selected from one of the following carbocyclic and heterocycles which are substituted with 0–2 $R^{4a}$;

cylcopropyl, cyclopentyl, cyclohexyl, phenyl, piperidinyl, piperazinyl, pyridyl, pyrimidyl, furanyl, morpholmyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

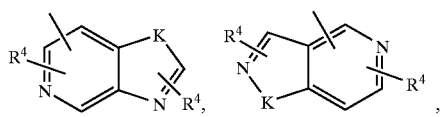

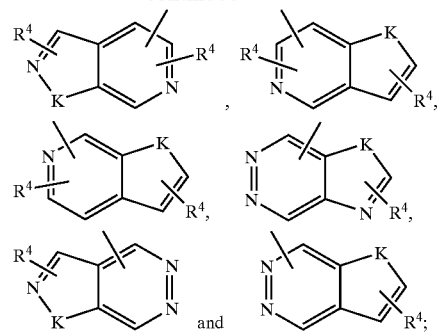

K is selected from O, S, NH, and N; and
V is selected from C, CH, and N.

4. A compound of claim 3, wherein:
ring G is substituted with 0–1 $R^{1a}$ and is:
A is selected from one of the following carbocyclic and heterocycles which are substituted with 0–2 $R^4$;
phenyl, piperidinyl, piperazinyl, pyridyl, pyrimidyl, furanyl, morpholinyl, thiophenyl, pyrrolyl, pyrrolidinyl, axazolyl, isoxazolyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is X—Y or is selected from one of the following carbocyclic and heterocycles which are substituted with 1–2 $R^{4a}$;
cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=$NR^{1c}$)—, —$CR^2(NR^2R^{2a})$—, —C(O)$CR^2R^{2a}$—, —$CR^2R^{2a}$C(O), —C(O)$NR^213$, —$NR^2$C(O)—, —C(O)$NR^2CR^2R^{2a}$—, —$NR^2$C(O)$CR^2R^{2a}$—, —$CR^2R^{2a}$C(O)$NR^2$—, —$CR^2R^{2a}NR^2$C(O)—, —$NR^2$C(O)$NR^2$—, —$NR^2$—, —$NR^2CR^2R^{2a}$—, —$CR^2R^{2a}NR^2$—, O, —$CR^2R^{2a}$—, and —$OCR^2R^{2a}$—;

Y is $(CH_2)_rNR^2R^{2a}$, provided that X—Y do not form a N—N or O—N bond;

alternatively, Y is selected from one of the following carbocyclic and heterocycles which are substituted with 0–2 $R^{4a}$;
cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzotbiofuranyl, indolyl, benzimidazolyl, benzoxazolyl, benzthiazolyl, indazolyl, benzisoxazolyl, benzisothiazolyl, and isoindazolyl; and alternatively, Y is selected from the following bicyclic heteroaryl ring systems:

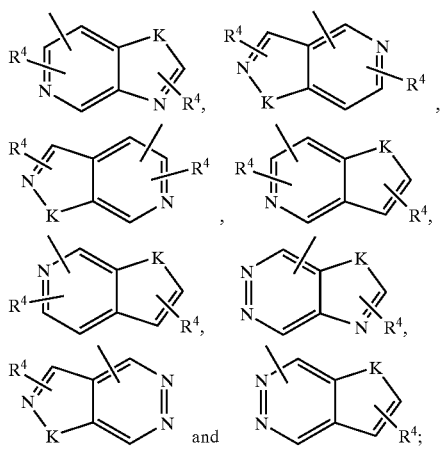

K is selected from O, S, NH, and N.

5. A compound of claim 4, wherein:

A is selected from phenyl, pyridyl, and pyrimidyl, and is substituted with 0–2 $R^4$;

B is selected from X—Y, phenyl, pyrrolidino, morpholino, 1,2,3-triazolyl, imidazolyl, and benzimidazolyl, and is substituted with 0–1 $R^{4a}$;

X is $CH_2$ or $C(O)$;

Y is selected from pyrrolidino and morpholino;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$;

alternatively, $R^2$ and $R^{2a}$, together with the atom to which they are attached, combine to form pyrrolidine substituted with 0–2 $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $(CH_2)_rOR^2$, $(CH_2)_rNR^2R^{2a}$, $S(O)_pR^5$, $SO_2NR^2R^{2a}$, and 1-$CF_3$-tetrazol-2-yl;

$R^{4b}$, at each occurrence, is selected from H, $CH_3$, and OH;

$R^{4c}$ is selected from $CO_2CH_3$ and $C(O)NH_2$;

$R^5$, at each occurrence, is selected from $CF_3$, $C_{1-6}$ alkyl, phenyl, and benzyl;

p, at each occurrence, is selected from 0, 1, and 2; and r, at each occurrence, is selected from 0, 1, and 2.

6. A compound of claim 5, wherein:

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methyiphenyl, 2-aminophenyl, and 2-methoxyphenyl; and B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N,N-diethylaminomethyl)phenyl, 2-(N-methylaminomethyl)phenyl, 2-(N-ethyl-N-methylaminomethyl)phenyl, 2-(N-pyrrolidinylmethyl)phenyl, 1-methyl-2-imidazolyl, 2-methyl-1-imidazolyl, 2-(N,N-dimethylaminomethyl)-1-imidazolyl, 2-(N-methylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, 2-(N-(4-hydroxypiperidinyl)methyl)phenyl, 2-(N-(3-hydroxypyrrolidiflyl)methyl)phenyl, and 2-(N-(2-hydroxyethyl)methylamino)-methyl)phenyl.

7. A compound of claim 1, or a pharmaceutically acceptable salt form thereof, wherein the compound is selected from:

1-{1-[3-fluoro-2'-(methylsulfonyl)[1,1'-biphenyl]-4yl]-2-oxo-3-piperidinyl}-1H-indole-6-carbonitrile;

1-(1-{2'-[(dimethylamino)methyl]-3-floro[1,1'-biphenyl]-4-yl}-2-oxo-3-piperidinyl)-6-indoline carbonitrile;

1-{1-[3-fluoro-2'-(methylsulfonyl)[1,1'-biphenyl]-4-yl]-2-oxo-3-piperidiflyl}-1H-indole-6-carboximidamide;

1-(1-{2'-[(dimethylamino)methyl]-3-fluoro[1,1'-biphenyl]-4-yl}-2-oxo-3-piperidinyl)-6-indoline carboximidamide;

ethyl-1-{1-[3-fluoro-2'-(methylsulfonyl)[1,1'-biphenyl]-4-yl]-2-oxo-3-piperidiflyl}-5-methoxy-1H-indole-2-carboxylate;

1-[3-fluoro-2'-(methylsulfonyl)[1,1'-biphenyl]-4-yl]-3-(5-methoxy-1H-indol-1-yl)-2-piperidinone;

3-{1-[3-fluoro-2'-(methanesulfofyl)-[1,1'-biphenyl]-4-yl]-2-oxo-piperidin-3-yl}-6-methoxy-3H-benzoxazol-2-one;

1-{1-[3-fluoro-2'-(methylsulfonyl)[1,1'-biphenyl]-4-yl]-2-oxo-3-piperidinyl}-1H-indazole-6-carboximidamide;

1-{1-[3-fluoro-2'-(methylsulfonyl)[1,1'-biphenyl]-4-yl]-2-oxo-3-piperidifyl}-3H-benzimidazole-5-carboximidamide;

1-{1-[(3-fluoro-2'-methylsulfonyl)[1,1'-biphenyl]-4-yl]-2-oxo-3-piperidinyl}-1H-benzimidazole-5-carboximidamide;

1-{1-[3-fluoro-2'-(methylsulfonyl)[1,1'-biphenyl]-4-yl]-2-oxo-piperdin-3-yl}-5-methoxy-1H-indole-2,3-dione;

1-[(3-fluoro-2'-methylsulfanyl)[1,1'-biphenyl]-4-yl]-3-(6-methoxy-3,4-dihydro-2H-quinolin-1-yl)piperidin-2-one;

1-[(3-fluoro-2'-methanesulfinyl)[1,1'-biphenyl]-4-yl]-3-(6-methoxy-3,4-dihydro-2H-quinolin-1-yl)piperidin-2-one;

1-{1-[3-fluoro-2'-(methylsulfonyl)[1,1'-biphenyl]-4-yl]-2-oxo-piperidin-3yl}-5-methoxy-1,3-dihydrobenzimidazol-2-one; and 1-[1-[3-fluoro-2'-methylsulfonyl-[1,1'-biphenyl]-4-yl]-2-oxo-piperdin-3-yl]-3-isopropyl-5-methoxy-1,3-dihydro-benzimidazol-2-one.

8. A pharmaceutical composition, comprising: a pharmaceutically acceptable carrier and a therapeutically effective amount of a compound of claim 1 or a pharmaceutically acceptable salt form thereof.

9. A method for treating a thromboembolic disorder, comprising: administering to a patient in need thereof a therapeutically effective amount of a compound of claim 1 or a pharmaceutically acceptable salt form thereof.

10. A method according to claim 9, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

11. A method according to claim 10, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

12. A method of treating a patient in need of thromboembolic disorder treatment, comprising: administering a compound of claim 1 or a pharmaceutically acceptable salt form thereof in an amount effective to treat a thromboembolic disorder.

13. A method, comprising: administering a compound of claim 1 or a pharmaceutically acceptable salt form thereof in an amount effective to treat a thromboembolic disorder.

14. A pharmaceutical composition, comprising: a pharmaceutically acceptable carrier and a therapeutically effective amount of a compound of claim 2 or a pharmaceutically acceptable salt form thereof.

15. A pharmaceutical composition, comprising: a pharmaceutically acceptable carrier and a therapeutically effective amount of a compound of claim 3 or a pharmaceutically acceptable salt form thereof.

16. A pharmaceutical composition, comprising: a pharmaceutically acceptable carrier and a therapeutically effective amount of a compound of claim 4 or a pharmaceutically acceptable salt form thereof.

17. A pharmaceutical composition, comprising: a pharmaceutically acceptable carrier and a therapeutically effective amount of a compound of claim 5 or a pharmaceutically acceptable salt form thereof.

18. A pharmaceutical composition, comprising: a pharmaceutically acceptable carrier and a therapeutically effective amount of a compound of claim 6 or a pharmaceutically acceptable salt form thereof.

19. A pharmaceutical composition, comprising: a pharmaceutically acceptable carrier and a therapeutically effective amount of a compound of claim 7 or a pharmaceutically acceptable salt form thereof.

20. A method for treating a thromboembolic disorder, comprising: administering to a patient in need thereof a therapeutically effective amount of a compound of claim 2 or a pharmaceutically acceptable salt form thereof.

21. A method according to claim 20, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

22. A method according to claim 21, wherein the thromboembolic disorder is selected unstable angina, first rnyocardial infarction, recurrent myocardial infarction, ischemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

23. A method for treating a thromboembolic disorder, comprising: administering to a patient in need thereof a therapeutically effective amount of a compound of claim 3 or a pharmaceutically acceptable salt form thereof.

24. A method according to claim 23, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

25. A method according to claim 24, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

26. A method for treating a thromboembolic disorder, comprising: administering to a patient in need thereof a therapeutically effective amount of a compound of claim 4 or a pharmaceutically acceptable salt form thereof.

27. A method according to claim 26, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

28. A method according to claim 27, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

29. A method for treating a thromboembolic disorder, comprising: administering to a patient in need thereof a therapeutically effective amount of a compound of claim 5 or a pharmaceutically acceptable salt form thereof.

30. A method according to claim 29, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

31. A method according to claim 30, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophiebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

32. A method for treating a thromboembolic disorder, comprising: administering to a patient in need thereof a therapeutically effective amount of a compound of claim or a pharmaceutically acceptable salt form thereof.

33. A method according to claim 32, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

34. A method according to claim 33, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

35. A method for treating a thromboembolic disorder, comprising: administering to a patient in need thereof a therapeutically effective amount of a compound of claim 7 or a pharmaceutically acceptable salt form thereof.

36. A method according to claim 35, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

37. A method according to claim 36, wherein the thromboembolic disorder is selected unstable angina, first myocardial infarction, recurrent myocardial infarction, ischemic sudden death, transient isehemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

* * * * *